US012270053B2

(12) United States Patent
Gallego-Perez et al.

(10) Patent No.: US 12,270,053 B2
(45) Date of Patent: Apr. 8, 2025

(54) NANO-ENGINEERED THERAPEUTIC STEALTH CELLS

(71) Applicant: Ohio State Innovation Foundation, Columbus, OH (US)

(72) Inventors: Daniel Gallego-Perez, Columbus, OH (US); William Carson, Hilliard, OH (US); Silvia M. Duarte Sanmiguel, Columbus, OH (US); Natalia Higuita-Castro, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 305 days.

(21) Appl. No.: 17/283,745

(22) PCT Filed: Oct. 18, 2019

(86) PCT No.: PCT/US2019/056988
§ 371 (c)(1),
(2) Date: Apr. 8, 2021

(87) PCT Pub. No.: WO2020/081966
PCT Pub. Date: Apr. 23, 2020

(65) Prior Publication Data
US 2021/0380949 A1    Dec. 9, 2021

Related U.S. Application Data

(60) Provisional application No. 62/747,980, filed on Oct. 19, 2018.

(51) Int. Cl.
| | |
|---|---|
| *C12N 5/09* | (2010.01) |
| *A61K 35/13* | (2015.01) |
| *A61K 35/15* | (2015.01) |
| *A61K 39/00* | (2006.01) |
| *C07K 14/81* | (2006.01) |

(52) U.S. Cl.
CPC .......... *C12N 5/0693* (2013.01); *A61K 35/13* (2013.01); *A61K 35/15* (2013.01); *A61K 39/461* (2023.05); *A61K 39/4621* (2023.05); *A61K 39/464499* (2023.05); *C07K 14/8146* (2013.01); *A61K 2239/31* (2023.05); *A61K 2239/38* (2023.05); *A61K 2239/49* (2023.05); *C12N 2509/10* (2013.01); *C12N 2510/00* (2013.01); *C12Y 304/24017* (2013.01)

(58) Field of Classification Search
CPC .............. C12N 5/0693; C12N 2509/10; C12N 2510/00; C12N 5/0694; G01N 33/5029; G01N 33/5011; A61K 35/13; A61K 35/15; A61K 35/30; C07K 14/8146; C12Y 304/24017; A61P 35/00
USPC ........................................................ 435/366
See application file for complete search history.

(56) References Cited

U.S. PATENT DOCUMENTS

| | | | | |
|---|---|---|---|---|
| 8,790,891 B2 * | 7/2014 | Irimia | ............... | B01L 3/502746 |
| | | | | 435/29 |
| 10,435,734 B2 * | 10/2019 | Kim | ............... | G01N 33/5002 |
| 2014/0348904 A1 | 11/2014 | Wood et al. | | |
| 2017/0247464 A1 | 8/2017 | Poirier et al. | | |
| 2018/0164313 A1 | 6/2018 | Gabrilovich et al. | | |
| 2018/0059115 A1 | 8/2018 | Gabrilovich et al. | | |

FOREIGN PATENT DOCUMENTS

| | | |
|---|---|---|
| CN | 103260650 A | 8/2013 |
| WO | 2012/054747 A3 | 4/2012 |
| WO | 2015/002956 A1 | 1/2015 |
| WO | 2018/015535 A1 | 1/2018 |
| WO | 2018/039119 A1 | 3/2018 |
| WO | WO-2018231951 A1 * | 12/2018 ............. A61K 35/15 |

OTHER PUBLICATIONS

Youn et al., "Subsets of Myeloid-Derived Suppressor Cells in Tumor Bearing Mice". J Immunol. Oct. 15, 2008; 181(8): 1-24 (Year: 2008).*
Gu et al., "TIMP-3 Expression Associates with Malignant Behaviors and Predicts Favorable Survival in HCC". PLoS ONE. Aug. 29, 2014; 9(8): 1-8. (Year: 2014).*
Baskar et al., "Gene-modified tumor cells as cellular vaccine". Cancer Immunol Immunother (1996) 43: 165-173 (Year: 1996).*
"Oncolytic Virus Therapy: Using Tumor-Targeting Viruses to Treat Cancer". NCI. Feb. 9, 2018. 1-11. (Year: 2018).*
Lohela et al., "Intravital imaging reveals distinct responses of depleting dynamic tumor-associated macrophage and dendritic cell subpopulations". PNAS PLUS. Nov. 10, 2014. E5086-E5095. (Year: 2014).*
European Extended Search Report, EP Patent App. 19872723.2, mailed May 17, 2022 (14 pages).
Shi, Jungfeng, "Development of Nanoelectroporation-based Biochips for Living Cell Interrogation and Extracellular Vesicle Engineering—Dissertation" Graduate Program in Mechanical Engineering, The Ohio State University (2017) (209 pages).
Ma, Yu-Heng Vivian, et al., "A review of microfluidic approaches for investigating cancer extravasation during metastasis," Microsystems and Nanoengineering, vol. 4 (2018) (13 pages).
García-Castro, Javier, et al., "Tumor cells as cellular vehicles to deliver gene therapies to metastatic tumors," Cancer Gene Therapy, vol. 12 (2005), pp. 341-349.
Bronte, Vincenzo, et al., "Recommendations for myeloid-derived suppressor cell nomenclature and characterization standards," Nature Communications, vol. 7 (2016) (10 pages).

(Continued)

*Primary Examiner* — Allison M Fox
*Assistant Examiner* — Hanan Isam Abuzeineh
(74) *Attorney, Agent, or Firm* — Thomas | Horstemeyer, LLP

(57) ABSTRACT

Disclosed herein is a method of "reprogramming" highly motile cells found in tumors, such as these highly motile GSC and/or MDSC clones, into "auto-destructive" cell "missiles" (referred to herein as therapeutic stealth cells) that can seek and destroy new foci of recurrence within the body, such as the brain. Cells with enhanced motility can be sorted out from heterogeneous populations and then be rendered "auto-destructive" by deterministic delivery of an anti-cancer agent, such as an oncolytic virus plasmid cocktail.

10 Claims, 45 Drawing Sheets

(56) References Cited

OTHER PUBLICATIONS

Xiang, Xiaoyu, et al., "Induction of myeloid-derived suppressor cells by tumor exosomes," Int. J. Cancer, vol. 124, No. 11 (2009), pp. 2621-2633.
Singapore Written Opinion, Singapore App. 11202103756X, mailed Dec. 23, 2022.
International Search Report issued for PCT/US2019/056988, mailed Jan. 6, 2020.
Gallego-Perez et al., On-Chip Clonal Analysis of Glioma-Stem-Cell Motility and Therapy Resistance, Nanoletters, vol. 16, No. 9; pp. 1-13, 2016.
Green et al., Chemoattractant Signaling between Tumor Cells and Macrophages Regulates Cancer Cell Migration, Metastasis and Neovascularization. PLoS One, vol. 4, No. 8; pp. 1-15, 2009.
IVICS, Self-Destruct Genetic Switch to Safeguard iPS Cells. Molecular Therapy, vol. 23, No. 9; pp. 1417-1420, 2015.
China Office Action and Search Report, Issued by China Patent Office on Jun. 27, 2023, CN Patent Application No. 201980073560.0.

* cited by examiner

Assembled device for automated migrational chromatography

NANO-ENGINEERED THERAPEUTIC STEALTH CELLS

CROSS-REFERENCE TO RELATED APPLICATIONS

This application is a National Stage of International Application No. PCT/US2019/056988, filed Oct. 18, 2019, which claims benefit of U.S. Provisional Application No. 62/747,980, filed Oct. 19, 2018, which is hereby incorporated herein by reference in its entirety.

BACKGROUND

Tumor cell dissemination is a major driver of cancer-related deaths (>90%) (Gallego-Perez, D. et al. Lab Chip 12:4424-4432 (2012); Fidler, I. J. Nat Rev Cancer 3:453-458 (2003); Gupta, G. P. & Massague, J. Cell 127:679-695 (2006)). Glioblastoma multiforme (GBM), in particular, is a lethal form of brain cancer with a highly invasive nature (Bellail, A. C., et al. Int J Biochem Cell Biol 36:1046-1069 (2004)). This aggressive tumor exhibits distinct intracranial spreading patterns, effectively disseminating as single cells along pre-aligned white matter tracts (Gallego-Perez, D. et al. Lab Chip 12: 4424-4432 (2012); Bellail, A. C., et al. Int J Biochem Cell Biol 36:1046-1069 (2004)). A growing amount of evidence suggests that the invasive phenotype of GBMs is modulated by cell motility (Giese, A., et al. J Clin Oncol 21:1624-1636 (2003)). Moreover, recurrence seems to be primarily driven by a subset of highly motile tumor initiating cells, known as glioma stem cells (GSCs), which are resistant to conventional therapies (Calabrese, C. et al. Cancer Cell 11:69-82 (2007); Ghotra, V. P., et al. Int J Radiat Biol 85, 955-962 (2009)). As GSCs continue to draw significant interest from the scientific and medical communities, new analytical and engineering tools are needed in order to better understand and counteract the mechanisms by which GSCs spread to develop new foci of tumor growth in the brain. Research on GSC motility and therapy resistance, however, has been limited compared to ongoing efforts on oncogenic transformation. This is due, in part, to the lack of effective tools to identify, study, and manipulate specific subsets of GSCs, or other cells of interest from the GBM niche, for research, diagnosis and/or therapeutic purposes. Characterizing tumors at the single-clone level via in vivo imaging is extremely challenging (Irimia, D. & Toner, M. Integr Biol (Camb) 1:506-512 (2009); Condeelis, J. & Segall, J. E. Nat Rev Cancer 3:921-930 (2003)). Moreover, current technologies for ex vivo analysis of tissue explants tend to be laborious and limited (Johnson, J. et al. Tissue Eng Part C Methods 15:531-540 (2009)). Conventional in vitro assays (Boyden, S. J Exp Med 115, 453-466 (1962); Albini, A. & Benelli, R. Nat Protoc 2, 504-511 (2007); Rao, J. S. Nat Rev Cancer 3, 489-501 (2003); Yamada, K. M. & Cukierman, E. Cell 130, 601-610 (2007); Liang, C. C., Park, A. Y. & Guan, J. L. Nat Protoc 2, 329-333 (2007)), on the other hand, are not physiologically-relevant, and/or are end-point tests that only focus on the bulk behavior of highly heterogeneous cellular populations.

SUMMARY

There is a subset of GSCs and MDSCs that exhibit high dissemination and therapy-resistance capacity. These findings suggest that GSCs and MDSCs are not monolithic populations, and that specific clonal subsets exhibit significantly more "aggressive" phenotypes, which could presumably be responsible for driving disease relapse.

Disclosed herein is a method of "reprogramming" highly motile cells found in tumors, such as these highly motile GSC and/or MDSC clones, into "auto-destructive" cell "missiles" (referred to herein as therapeutic stealth cells) that can seek and destroy new foci of recurrence within the body, such as the brain. Cells with enhanced motility can be sorted out from heterogeneous populations and then be rendered "auto-destructive" by deterministic delivery of an anti-cancer agent, such as an oncolytic virus plasmid cocktail.

The disclosed method can involve sorting cells from a subject to create the therapeutic stealth cells. In some embodiments, the cells are autologous, such as a blood cells or a tumor biopsy from the subject to be treated. However, in some cases, the cells are allogenic.

The disclosed method can involve sorting cells from a subject for a highly motile subpopulation and then reprogramming the subpopulation to deliver anti-cancer agents. In some embodiments, the subpopulation can be sorted in a migration assay using a chemoattractant gradient. In particular, the chemoattractant gradient can involve a chemokine produce by the tumor to be treated. For example, in some embodiments, the chemoattractant comprises Matrigel®. In some embodiments, the chemoattractant comprises tumor cell conditioned media.

In some embodiments, the subpopulation is sorted in a migration assay using a nanotextured and/or biomimetic surface. For example, MDSCs are responsive to, and can be guided along, pre-aligned structural cues in the absence of biochemical stimulation. Therefore, in some embodiments, the surface comprise ridges/grooves at the micro nor nanoscale. For example, the depth and width of the ridges/grooves can have dimensions from 100 nm to 10 µm, including, 100 nm to 1 µm, 1 µm to 10 µm, 500 nm to 5 µm. The ridges/grooves can have a variety of shapes and patterns, including straight grooves.

In some embodiments, the subpopulation is sorted in a transwell migration assay or cell invasion assay. A transwell migration assay measures the number of cells passing a porous membrane, whereas a cell invasion assay focuses on invasive cell migration via an extracellular matrix.

Once subpopulation is sorted and optionally expanded, the cells can then be reprogrammed to heterologously express a transgene encoding an anti-tumor protein, oligonucleotide, or combination thereof.

The introduction of an efficient "safety switch" can in some cases be used to reduce the risk of severe graft-vs-host disease. Therefore, in some embodiments, the subpopulation is also reprogrammed with a kill switch system. The most extensively studied safety-switch to date is the HSV I-derived thymidine kinase (HSV-TK) gene product. Non-immunogenic safety switch system have also been developed that involve fusion proteins composed of human proapoptotic molecules (e.g. caspase-9) linked to modified human FK506-binding proteins (i.e. iCasp9). These safety switches can be activated by injection of a chemical inducer of dimerization (CID), consisting of a dimer of two synthetic variants of FK506. Other inducible and self-destructive kill switches are in development and can be used in the disclosed therapeutic stealth cells.

Also disclosed is a composition comprising a plurality of therapeutic stealth cell produced by the disclosed methods. In particular embodiments, the composition further comprises a pharmaceutically acceptable excipient.

Also disclosed is a method for treating a tumor in a subject, comprising administering to the subject an effective amount of the disclosed pharmaceutical composition. The disclosed method can be used to treat any solid tumor. In particular embodiments, the tumor is matched to the source of cells used to develop the therapeutic stealth cells. For example, highly motile MDSCs obtained from a breast tumor biopsy can be reprogrammed to treat breast cancer. Likewise, highly motile GSCs/MDSCs obtained from a glioblastoma multiforme (GBM) biopsy can be reprogrammed to treat GBM.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows nanotextured surfaces induce guided motility. Clones of with high motility are lured into a collection chamber by chemoattraction. FIG. 1B shows studies with GSCs show that highly motile clones were resistant to anti-miR363 therapy. FIG. 1C shows migration-based sorting of MDSCs uncovered a clonal subset with superior motility compared to bulk MDSCs. FIG. 1D shows sorting exhibited a diverse phenotype with granulocytic (P4) and monocytic (P5) subtypes. Unclassified subtypes exhibiting either low (P6) or high (P3) Ly6-C/G were also present. FIG. 1E shows MDSC clones with high motility were either P4 or P3. *p<0.05.

FIG. 6A show single clone motility assays of patient-derived MDSCs show inhibition of a specific clonal subset (average velocity >40 μm/h) in response to ibrutinib. FIG. 6B shows single-clone motility on TCP did not reveal any effect of ibrutinib on MDSC dissemination.

FIG. 10A is a schematic diagram of the tumor microenvironment showing invasive cancer cells and infiltrative MDSCs using pre-aligned structural cues (e.g., remodeled ECM, blood vessel walls) to escape and invade the tumor stroma, respectively. FIG. 10B is a SEM micrograph (with superimposed MDSC mock-ups) of a PDMS-based biomimetic textured surface used to evaluate structurally guided MDSC migration at the single-clone level. FIG. 10C shows Actin—Nuclei staining of MDSCs cultured on textured vs. control/TCP surfaces. MDSCs assume an aligned/more migratory morphology on the textured surfaces compared to TCP. FIGS. 10D and 10E show single-clone dissemination tracks (FIG. 10D) and quantification of MDSCs (FIG. 10E) on textured vs. control/TCP surfaces confirming enhanced dissemination capabilities (i.e., average single-clone velocity and net track distance) for MDSCs when exposed to pre-aligned structural cues. The net track distance is a reflection of the geometrical distance traveled by a cell during the tracking period. *p<0.01 and ‡p<0.02 (t-test, n=4).

FIGS. 11A and 11B are schematic diagrams of an experimental design. Here MSC-2 cultures were sorted by flow cytometry into three distinct subpopulations, including granulocytic ($CD11b^+Ly6C^{lo}Ly6G^+$) and monocytic ($CD11b^+Ly6C^{hi}Ly6G^-$) MDSCs, as well as $CD11b^+Ly6C^+Ly6G^+$ cells. Each population was then subjected to single-clone motility assays on textured PDMS and qRT-PCR analyses of pro- and anti-inflammatory markers. FIG. 11C shows Actin-Nucleistaining of different MSC-2 subtypes cultured on textured surfaces. Granulocytic MDSCs had a tendency to exhibit a more aligned and migration-prone morphology compared to their counterparts. FIG. 11D shows singleclone dissemination (i.e., average velocities and net track distances) quantification for each subtype on textured surfaces. *p=0.006, **p<0.001, ψp=0.001, ‡p=0.09 (2-way ANOVA, n=4). FIG. 11E shows single-clone tracks for each population. FIG. 11F shows fluorescently labeled flow-sorted MDSCs vs. "fresh"/unsorted MDSCs injected (i.e., via the tail vein) into tumor-bearing mice (i.e., orthotopic breast tumor developed from human cells in nude mice). Photographs to the right depict tumor progression/growth from week 1 to week 4. FIG. 11G shows tumors and other target organs imaged to detect the degree to MDSC infiltration 24 hours post-injectio. FIGS. 11H and 11I show qRT-PCR analysis of pro-inflammatory (FIG. 11H) and anti-inflammatory (FIG. 11I) genes for each subtype. *p<0.001, **p<0.0001, ‡p=0.03 (2-way ANOVA, n=3-4).

FIG. 12A is a schematic diagram of the experimental design. FIG. 12B shows single-clone dissemination (i.e., average velocities and net track distances) studies did not show significant differences between all three populations by day 7. FIG. 12C to 12E show flow cytometry analyses indicate that while by day 1 post-sorting all subpopulations remained relatively pure, by day 7 the entire spectrum of phenotypes had been replenished regardless of the phenotype of the starting cell population. *p<0.0001, ‡p=0.01, #p=0.03, ψp=0.0001 (2-way ANOVA/Tukey's multiple comparisons, n=3-4). FIGS. 12F and 12G show qRT-PCR analyses of pro-inflammatory (FIG. 12F) and anti-inflammatory (FIG. 12G) genes at day 7 post-sorting. *p=0.006, **p=0.01 (2-way ANOVA/Tukey's multiple comparisons, n=3-6).

FIGS. 13A and 13B show average single clone velocities (FIG. 13A) and net track distances (FIG. 13B) had a tendency to be significantly higher for certain patients compared to the rest of the patient population, which could be a reflection of the patient's background.

FIGS. 14A to 14C show melanoma patient MDSCs were sorted into granulocytic ($CD11b^+CD15^+CD14^-$) and monocytic ($CD11b^+CD15^-CD14^+$) subpopulations via flow cytometry. FIGS. 14D to 14F show that similar to observations in mouse MDSCs, the granulocytic subpopulation of patient-derived MDSCs also shows increased dissemination (i.e., average single-clone velocities and net track distances) capabilities compared to the monocytic subtype. *p=0.0005, **p=0.002 (Mann-Whitney, n=3).

DETAILED DESCRIPTION

Figure 1A:
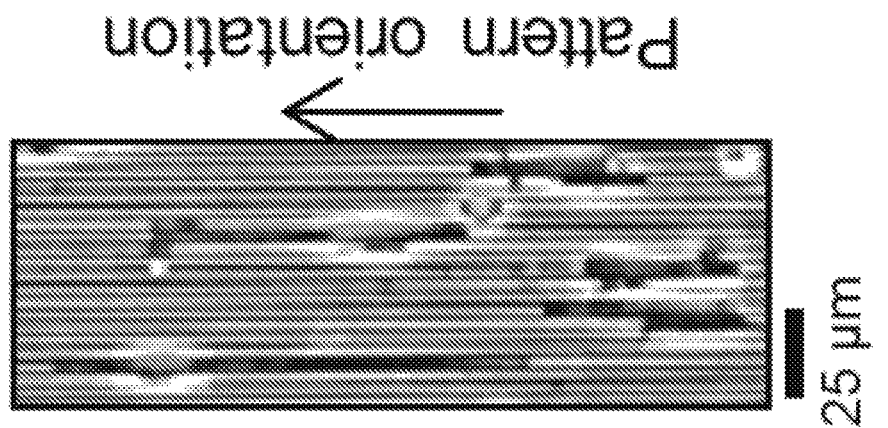
FIGS. 1A to 1E show results of a migration-based sorting/ "chromatography".
Figure 1A:
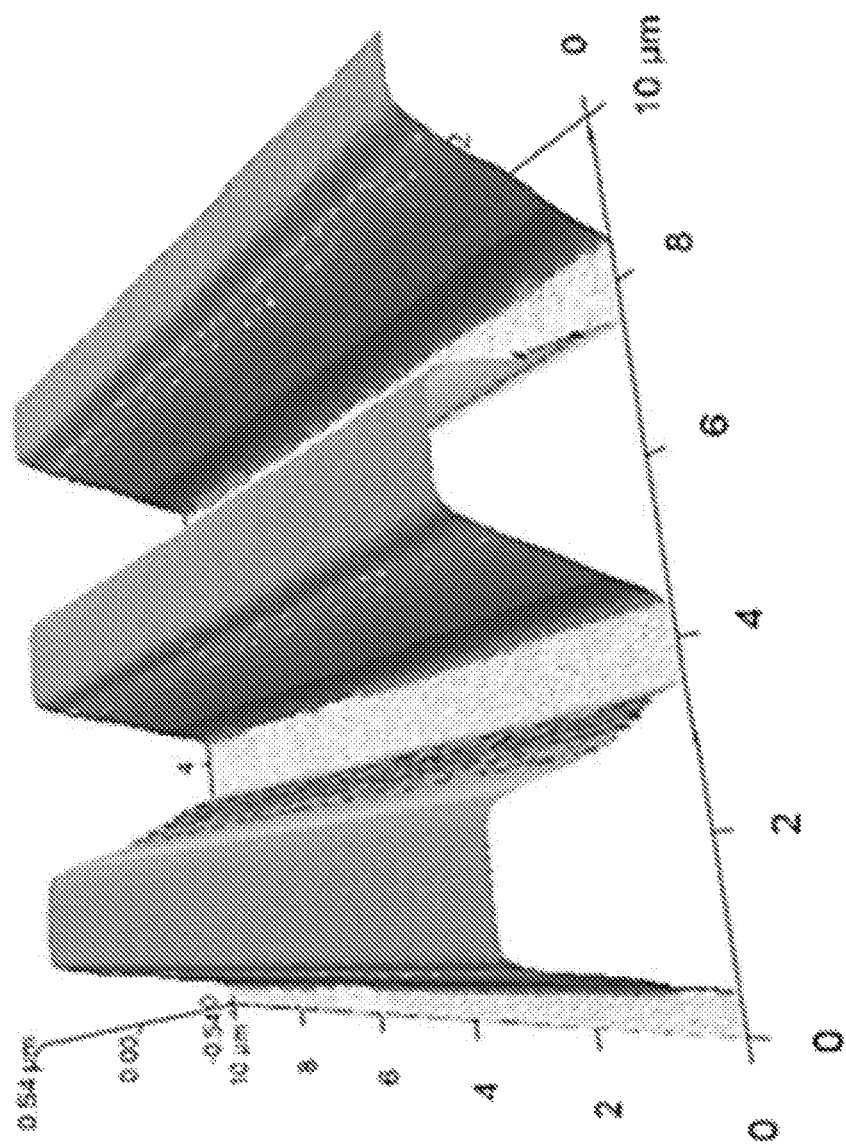
Figure 1C:
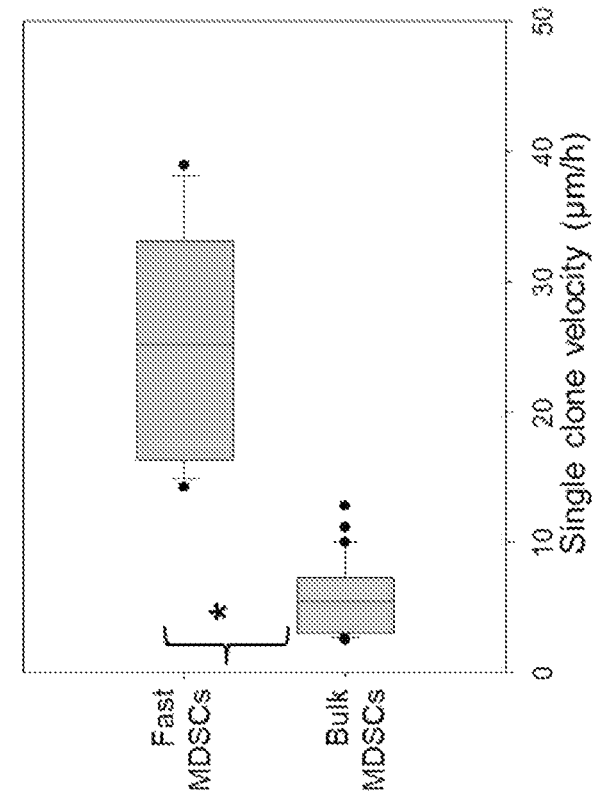
Figure 1B:
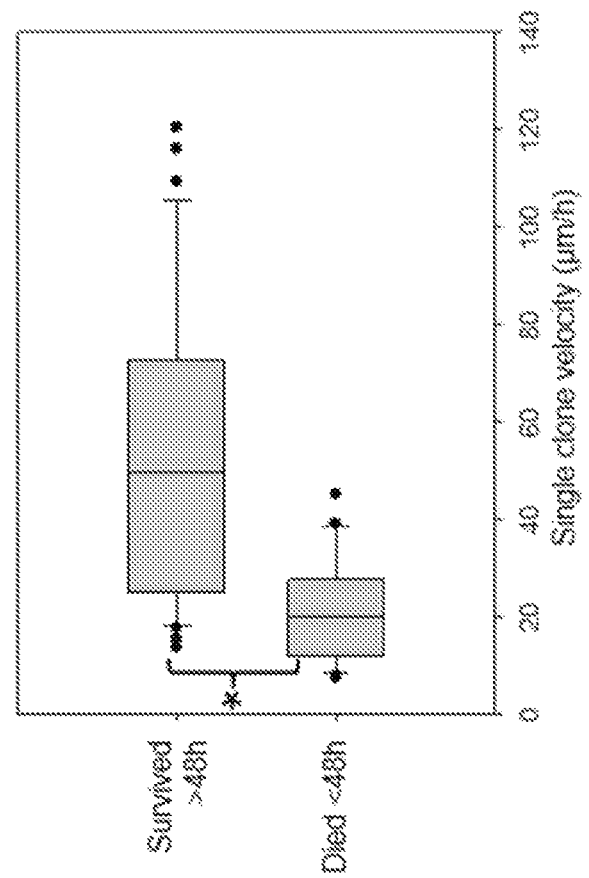
Figures 1D, 1E:
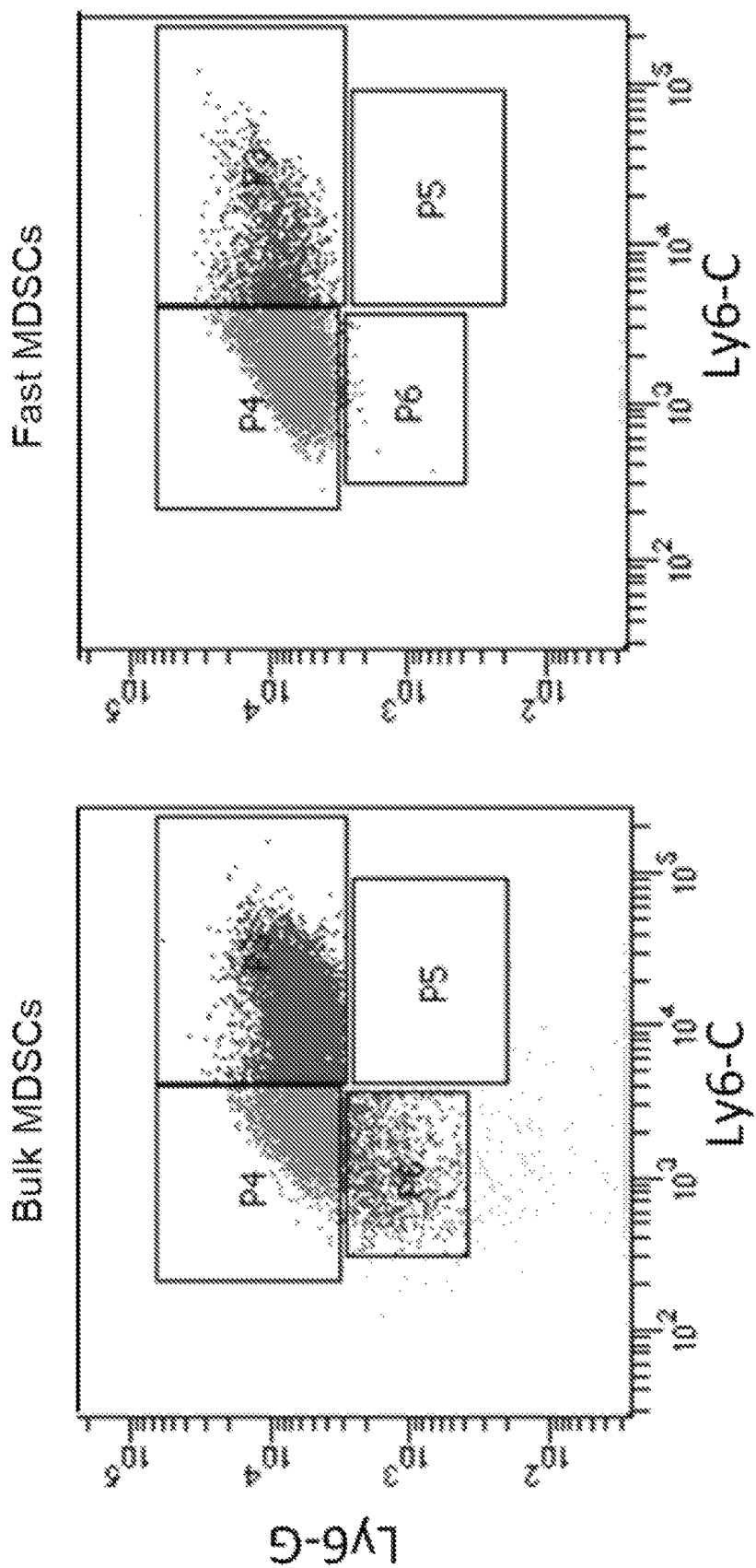

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

"Suicide gene" as used herein refers to a gene that will cause a cell to kill itself through apoptosis. Activation of these genes may be due to many processes, but the main cellular "switch" to induce apoptosis is the p53 protein. Stimulation or introduction (through gene therapy) of suicide genes may be used to treat cancer or other proliferative diseases by making cancer cells more vulnerable, more sensitive to chemotherapy. Parts of genes expressed in cancer cells are attached to other genes for enzymes not found in mammals that can convert a harmless substance into one that is toxic to the tumor. The suicide genes that mediate this sensitivity may encode for viral or bacterial enzymes that convert an inactive drug into toxic antimetabolites that inhibit the synthesis of nucleic acid.

Highly motile GSC and/or MDSC clones can be sorted from heterogenous populations by migration-based sorting, such as nano chip-supported single-clone motility chromatography. The method of migration-based cell sorting involves identifying clonal subsets and/or cell subpopulations that exhibit enhanced dissemination capabilities compared to the rest of the population. Such cells are inherently more prone to homing/infiltrating to primary tumors and/or metastatic outgrowths, and as such could serve as more efficient drug/gene delivery vehicles. Identifying highly disseminative clonal subsets could be achieved in many different ways.

One option is to seed cell mixtures on a micro- or nano-textured surface with lines, which would induce contact-guided directional migration of the cells. For example, MDSCs are responsive to, and can be guided along, pre-aligned structural cues in the absence of biochemical stimulation Cells could be exposed to a chemoattractant gradient, which would define a specific direction in which the cells would migrate, and "fast-moving" clones could be progressively collected in a reservoir as they migrate towards the chemoattractant. Running this sorting in the absence of a chemoattractant could also be used as a way to identify clonal subsets that may be more prone to showing single-direction motility (i.e., towards the collection reservoir), even in the absence of a chemoattractant. Even if these cells are not necessarily the fastest movers, their ability to exhibit persistent motility in a single direction could translate into enhanced ability to disseminate in vivo (e.g., cells with high migration velocity but with lack of directionality may not necessarily be the most effective "infiltrators"), which would also make these clones desirable for enhanced drug/gene delivery to the primary tumor and/or metastatic outgrowths.

Another way to select cells with enhanced dissemination capabilities could be through a translocation assay on a transwell system (e.g. 8 micron pores). For example, the cells can be seeded on one the top chamber of the transwell, and cells with enhanced dissemination capabilities will gradually translocate across the pores into the bottom chamber, where they could be collected for further modification (for gene/drug delivery applications).

As disclosed herein, the disclosed subpopulation of cells are CD11b$^+$Ly6C$^{lo}$Ly6G$^+$ myeloid-derived suppressor cells. Therefore, in some embodiments the highly motile cells are obtained by cell sorting of tumor-derived GSCs and/or MDSCs using a combination of antibodies that selectively bind CD11b, Ly6C, and Ly6G.

In some embodiments, the cells are derived from primary tumor cells (e.g., isolated from a routine biopsy). In some embodiments, the cells are derived from myeloid-derived suppressor cells (e.g., isolated from the circulation). However, the disclosed methods could be applied to any other cell type that is prone to infiltrating into cancerous tissue (e.g., other monocytes, T cells, etc.).

Once the pre-selection of highly disseminative clones is complete, these cells could be first expanded, and then genetically engineered through various routes, including viral or non-viral (e.g., bulk electroporation, tissue nanotransfection) delivery of transgenes, and/or CRISPR/CAS9-driven transgene insertion. The goal of this step is to induce the production of anti-tumor proteins, oligos, and/or other entities (e.g., glut1, mir146, oncolytic viruses, etc.) by these cells. Once genetic engineering of these highly motile subpopulations is complete, these cells could then be delivered back into the patient, either systemically (e.g., in blood, lymphatic system), or locally (into primary tumors or metastatic ones), with the intent to eradicate cancerous outgrowths. In some embodiments, the transgene encodes tissue inhibitor of metalloproteinase-3 (TIMP-3).

For cancer applications, these cells can be engineered (through transfection) to express pro-inflammatory molecules (ccl4, mir146, glut1 for example) to promote T cell infiltration into the tumor, or anti-metastasis components (e.g., timp3) to prevent cancer dissemination.

In some embodiments, MDSCs are used to deliver therapeutics in other conditions, such as Alzheimer's disease or diabetes, delivering anti-inflammatory molecules, or other forms of brain injury (e.g., ischemic stroke), where MDSCs home naturally, so that once can deliver therapeutic cargo such as pro-angiogenic and/or pro-neuronal, or anti-inflammatory agents.

These autologous cells could be further engineered (before injecting them back into the patient) with a drug-inducible (e.g., doxycycline) "kill switch" system, to eradicate the therapeutic cells when their action is no longer needed. Kill-switch system is known in the art, and therefore, it is within the purview of one skilled in the art to select and employ a suitable kill-switch system.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Nano-Engineering Therapeutic Stealth Cells

The dissemination capabilities of GSCs, as well as their ability to evade the immune system or standard therapies, continue to be major drivers of lethality. Nanoscale tools were used to isolate and study a specific subset of GSCs exhibiting high dissemination and therapy-resistance capacity (FIG. 1).

Pilot studies with MDSCs have also revealed a clonal subset with remarkable dissemination ability, akin to GSCs (FIG. 1). These findings suggest that GSCs and MDSCs are not monolithic populations, and that specific clonal subsets exhibit significantly more "aggressive" phenotypes, which could presumably be responsible for driving disease relapse. Disclosed in this Example is the development of a transformative, high-risk/high-reward approach, to minimize GBM recurrence by "reprogramming" highly motile GSC and/or MDSC clones into "auto-destructive" cell "missiles" that can seek and destroy new foci of recurrence within the brain. GSCs and MDSCs with enhanced motility are sorted out from heterogeneous populations via nano chip-supported single-clone motility "chromatography", as illustrated in FIG. 1. These cells then undergo a limited clonal expansion (2-5 passages), and subsequently are rendered "auto-destructive" by deterministic, nanochannel-based delivery (Gallego-Perez, D. et al. Nanomedicine 12:399-409 (2016)) of an oncolytic virus plasmid cocktail. These viruses can kill cancerous cells through different mechanisms compared to conventional therapies, and as such have been proposed as a potential therapeutic alternative to eradicate GSCs (Cripe, T. P., et al. Mol Ther 17:1677-1682 (2009)).

Figure 2:
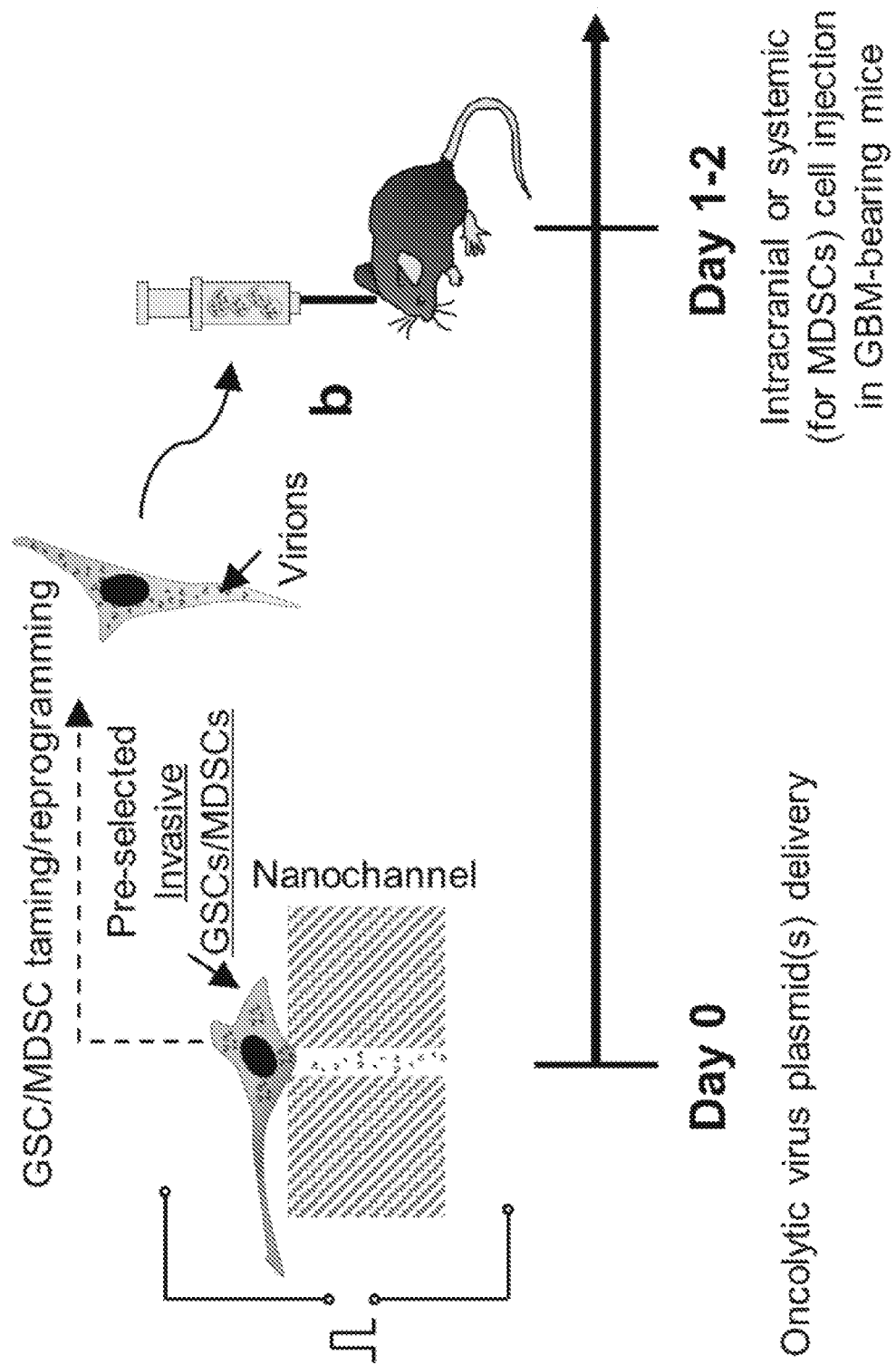
FIG. 2 depicts reprogrammed/tamed GSCs and/or MDSCs being intracranially injected in GBM-bearing mice and tumor progression being monitored.

A series of in vitro studies are conducted to determine the optimum plasmid dosage and ratios at which the select subgroup of GSCs or MDSCs are rendered "auto-destructive", while retaining superior motility for prolonged periods of time. These "tamed" but highly motile GSC/MDSC populations are then intracranially injected (together and separately) into GBM-bearing mice, with the intent to have them effectively disseminate, and strategically release therapeutic virions throughout the diseased brain (FIG. 2).

Comparative experiments of systemic delivery of reprogrammed/drugged MDSCs are also run in GBM-bearing mice in order to verify that these cells are able home to the diseased brain and hamper tumor progression. Advanced imaging technologies (e.g., IVIS, PET, MRI) are used to monitor the fate of therapeutic GSCs/MDSCs. Although cell-based oncolytic virus therapies have previously shown promising results compared to direct treatment with oncolytic virus particles (Power, A. T. & Bell, J. C. Mol Ther 15:660-665 (2007)), a major limitation is that most of the cells that have been studied so far have reduced dissemination capabilities, especially when compared to the pace of intracranial dissemination of GSCs. Tamed/reprogrammed GSCs or MDSCs, on the other hand, can have inherently high intracranial motility capabilities in addition to stealth ability toward the immune system, thus allowing them to colonize, surveil and treat the diseased brain more effectively.

Example 2: Structurally Guided Dissemination of Mouse MDSCs

Figure 3:
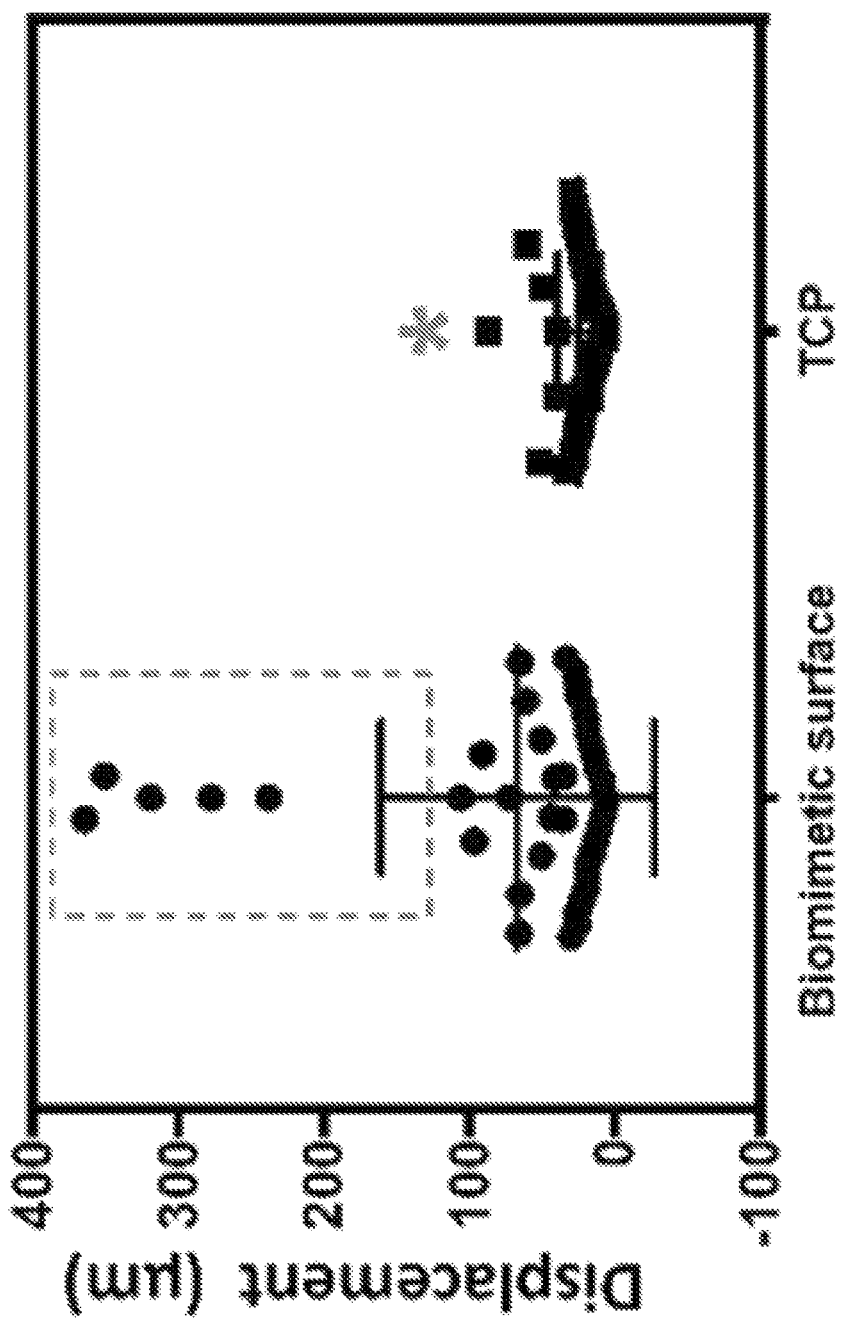
FIG. 3 shows MDSCs exhibit significant motility (i.e., guided) on textured/biomimetic surfaces. MDSCs cultured on TCP, on the other hand, exhibit limited motility. These results suggest that much like tumor cells, MDSCs may be responsive to the same structural cues that enhance tumor cell dissemination in vivo. *p<0.05.
Figures 4A, 4B:
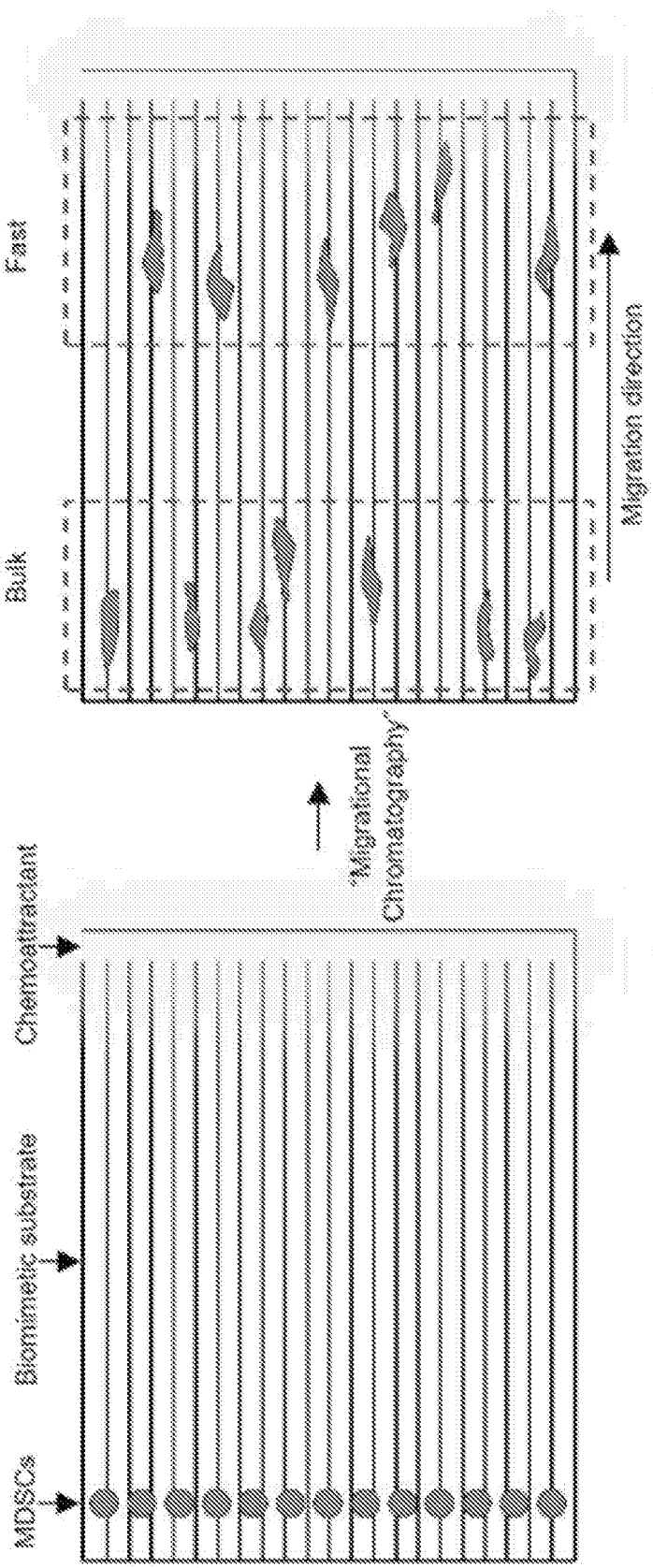
FIGS. 4A and 4B illustrate a migrational chromatography setup, where MDSCs are selectively seeded on one side of the platform, and induced to migrate in a single direction via chemotaxis. The surface nanotexture triggers clone separation based on guided motility.
Figure 4C:
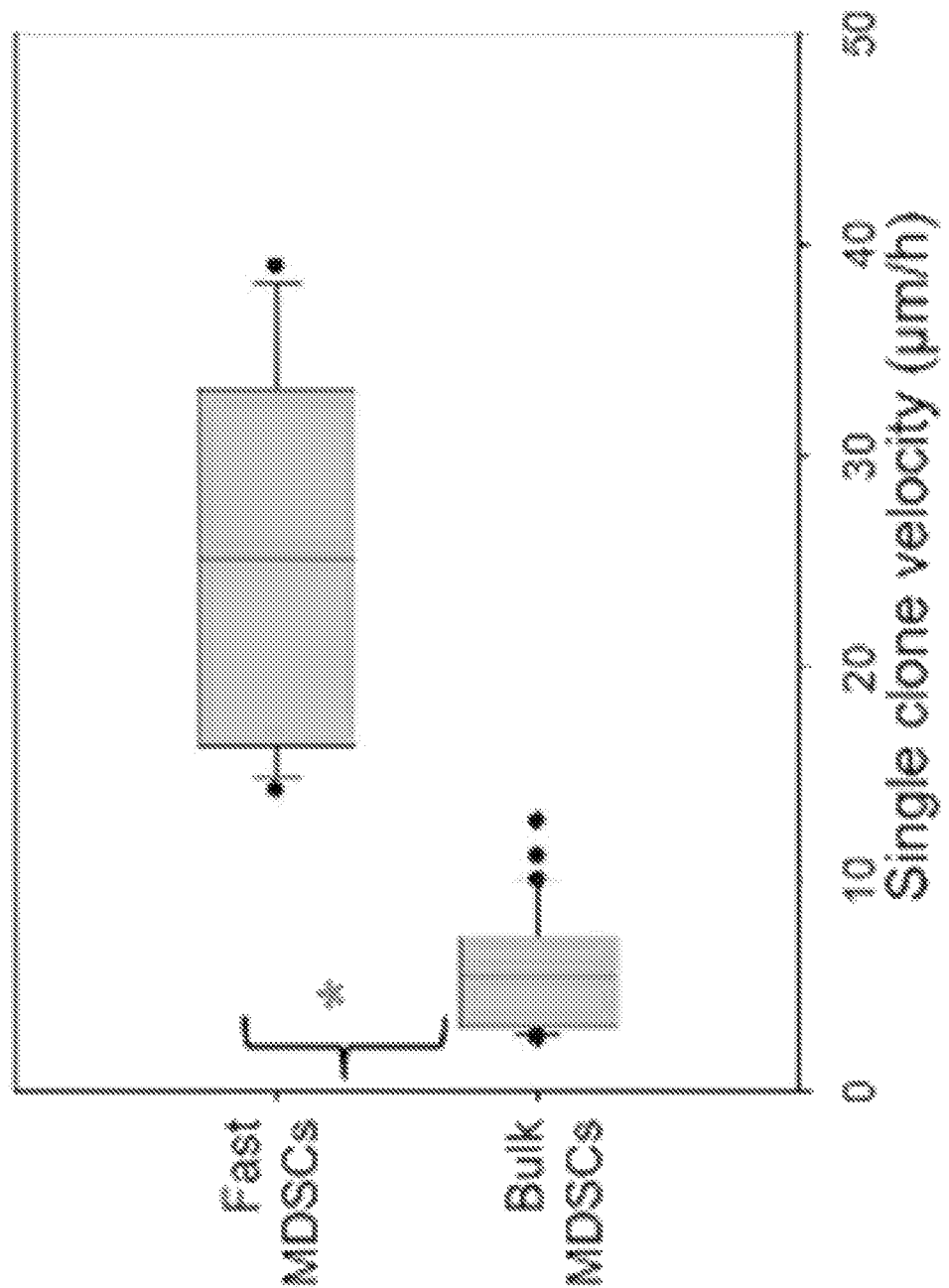
FIG. 4C shows velocity for fast- vs. slow-moving cells.
Figure 4E:
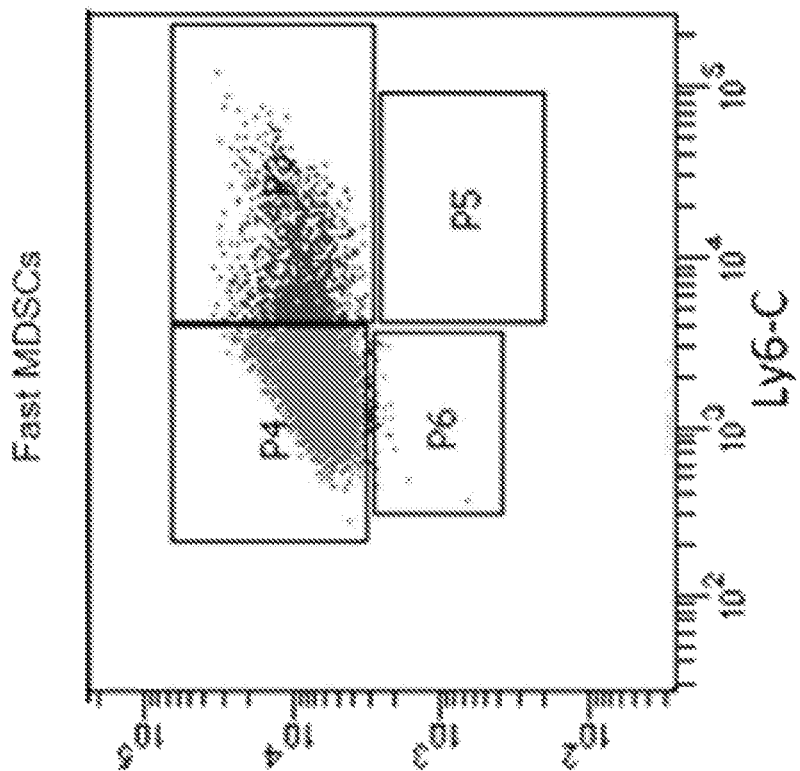
FIGS. 4D and 4E contains flow cytometry analysis showing that fast-moving clones have a distinct phenotype compared to slow-moving clones (e.g., bulk MDSCs). *p<0.05.
Figure 4D:
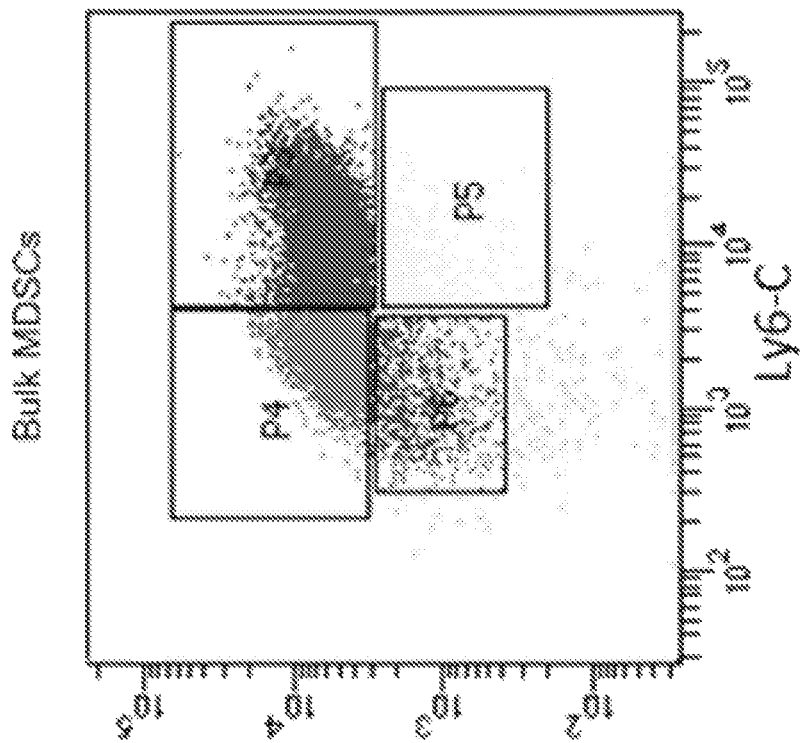

Recent studies indicate that MDSCs are responsive to, and can be guided along, pre-aligned structural cues (FIGS. 3-4), in the absence of biochemical stimulation. In contrast, single-clone motility assays on tissue culture polystyrene (TCP) revealed little dissemination capabilities (FIG. 3), suggesting that much like tumor cells, MDSC dissemination/infiltration is presumably favored by structurally guided migration. Chip-supported migrational chromatography studies revealed a clonal subset with enhanced dissemination capabilities compared to the rest of the population (FIG. 4A-4C), comparable to highly aggressive cancerous cells. Flow cytometry analyses of fast-moving clones revealed that such population was predominately Ly6-G$^{high}$/Ly6-C$^{low}$ (granulocytic) and Ly6-G$^{high}$/Ly6-C$^{high}$ (unidentified). The phenotype of slow-moving clones was more evenly distributed between monocytic (Ly6-G$^{low}$/Ly6-C$^{high}$) and granulocytic, as well as the unidentified variants Ly6-G$^{low}$/Ly6-C$^{low}$ and Ly6-G$^{high}$/Ly6-C$^{high}$. Therefore, MDSCs clearly have specialized clonal subsets with improved dissemination capabilities, which presumably would be more prone to colonizing tumors/ganglia to exert immunosuppression. Such clonal subsets could thus represent novel therapeutic targets in the fight against cancer.

Example 3: Structurally Guided Dissemination of Patient MDSCs

Next tested was whether patient-derived MDSCs also exhibit structurally guided migration in the absence of biochemical stimuli. MDSCs isolated from peripheral blood of different stage melanoma patients, under different treatment modalities, were tracked for ~24h. The MDSCs of each patient exhibited unique dissemination patterns/signatures, with some patients showing clonal subsets with enhanced mobility compared to the bulk population (FIG. 5), which remained clustered below 25 μm/h. Of note, some patients had MDSCs whose velocity clustered entirely below 25 μm/h, possibly indicative of an apparently "quiescent" population, presumably reflective of the type of malignancy, and/or the modality/stage of the therapy. While more studies are needed to establish a clear correlation between these factors and the single-clone dissemination capabilities/signatures of MDSCs, which could serve as a proxy for their level of in vivo activity and/or disease outcomes, these data further support the notion that MDSCs are not monolithic, and that exploring motility-related mechanisms could potentially pave the way for the development of not only improved therapies but also new diagnostics/prognosis tools.

Example 4: Structurally Guided Migration Uncovers Drug Susceptibilities

Figure 5A:
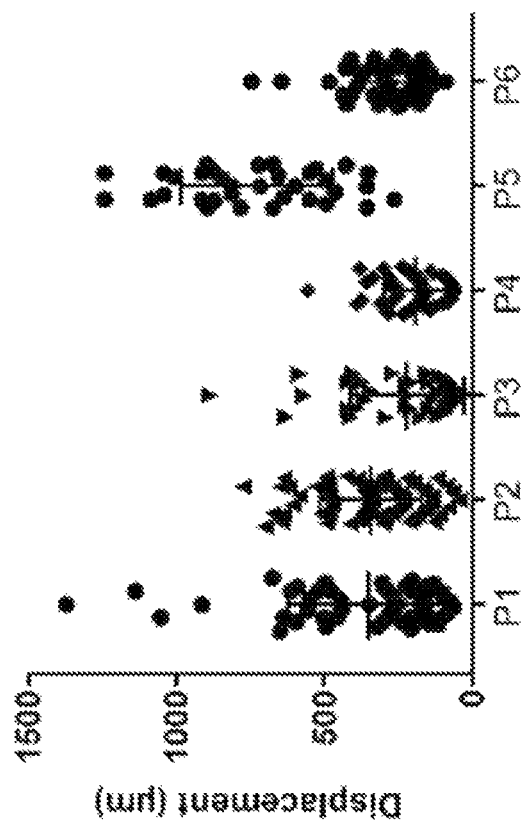
FIGS. 5A and 5B show single-clone motility assays of circulating MDSCs from melanoma patients. Differences in velocity (FIG. 5A) and effective displacement (FIG. 5B) for each patient. The results indicate that MDSCs from certain patients exhibit enhanced velocities. However, when effective displacement is considered (i.e., geometrical distance from starting to ending location), certain MDSC batches with low velocity showed significant displacement, which may be reflective of more directional/persistent motility (without chemotaxis). P1: stage IIIC, tx nivolumab+surgery; P2: stage IV, tx nivolumab; P3: stage IV V600E/BRAF, tx radiation+pembrolizumab; P4: stage IV, tx nivolumab+ipilumamab; P5: stage IV, tx pembrolizumab/ipilumamab/nivolumab; P6: stage IV V600E/BRAF, treated with INF-α).
Figure 5B:
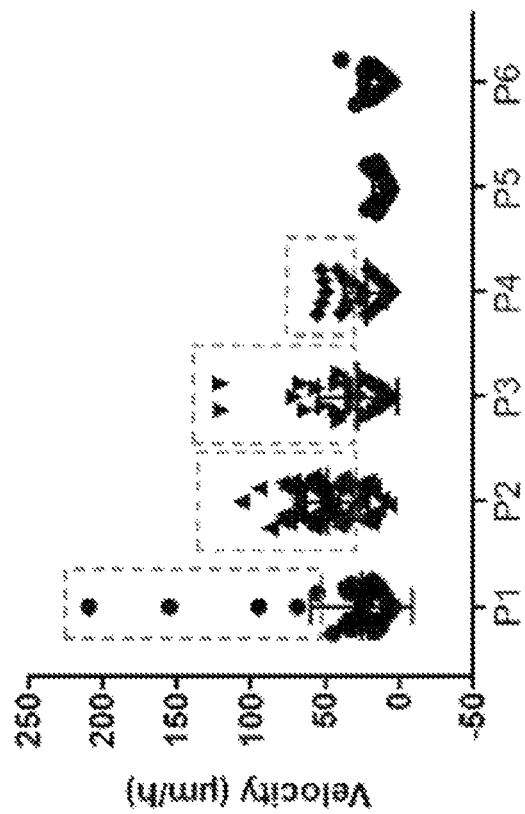
Figure 6A:
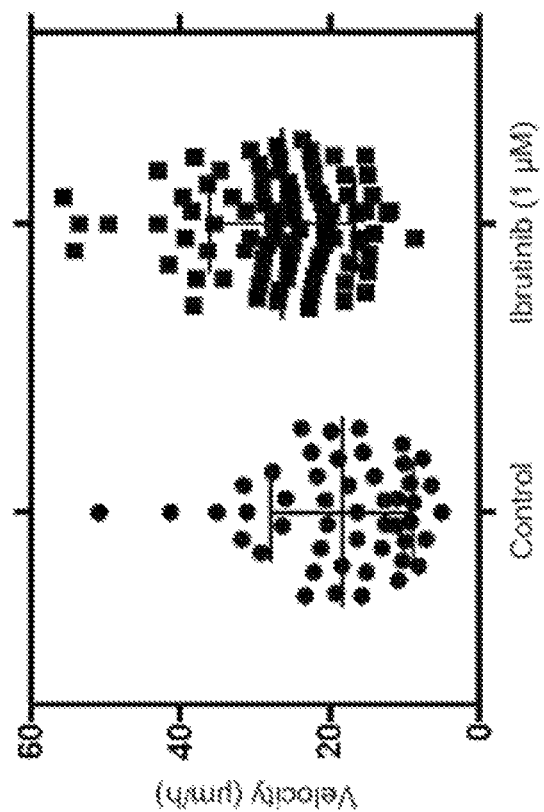
FIGS. 6A and 6B shows nanotextured surfaces can be used to unmask drug sensitivities not observed on standard TCP.
Figure 6B:
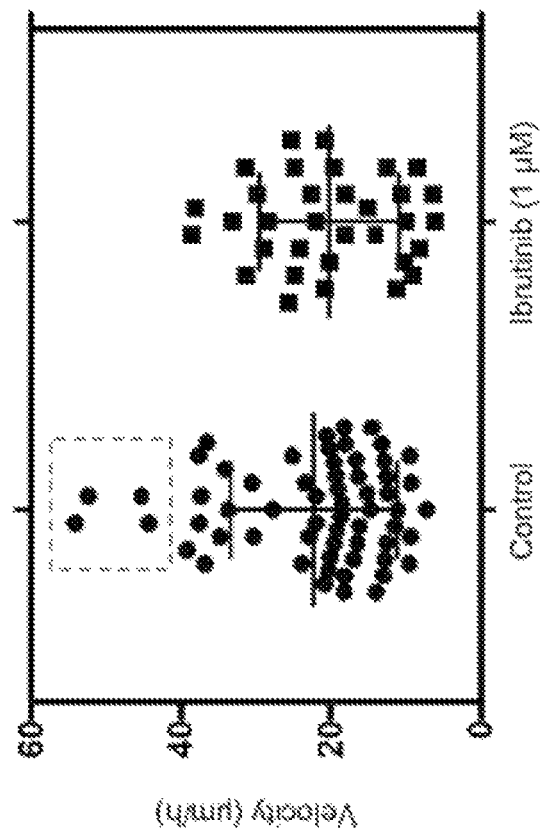
Figure 7A:
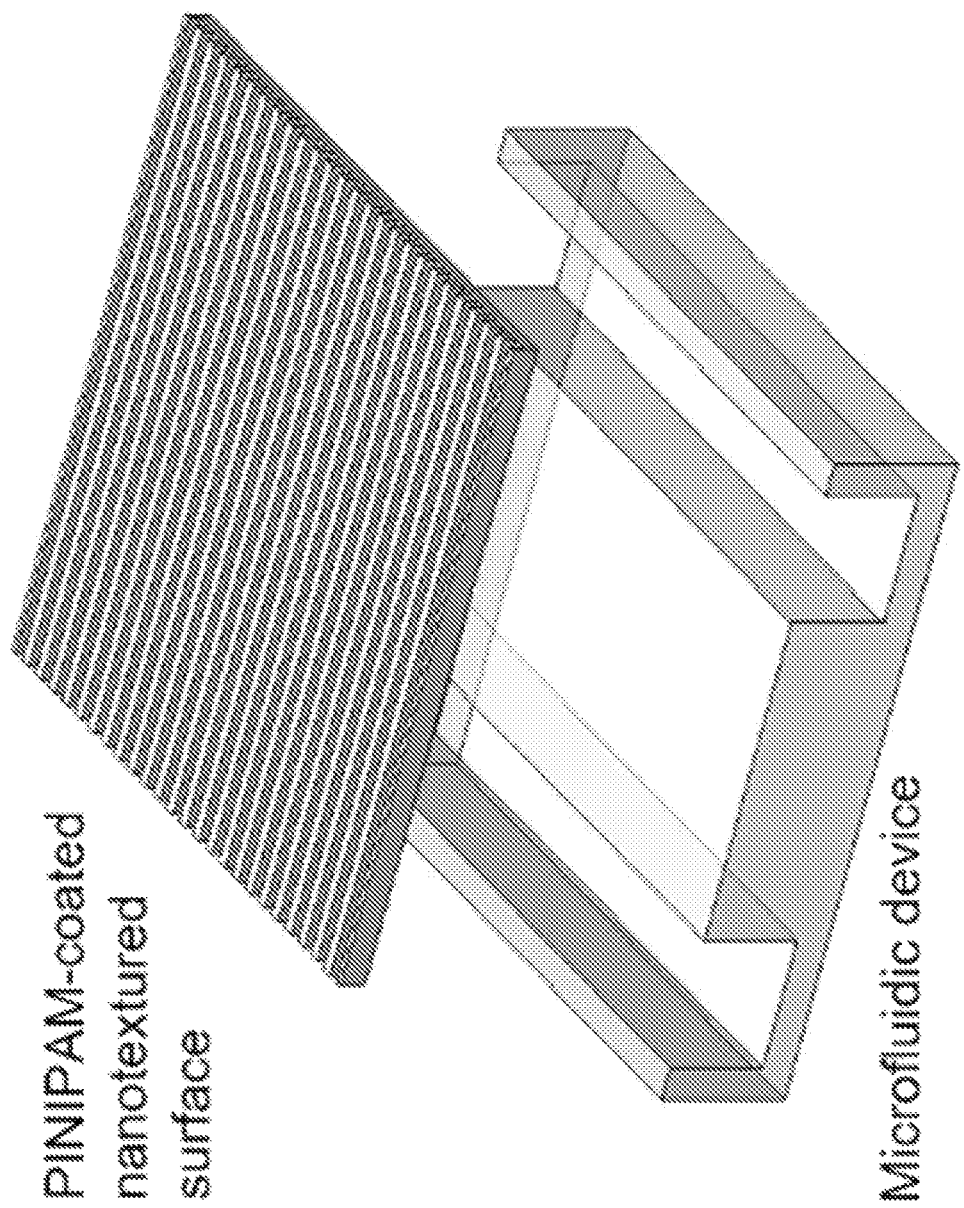
FIGS. 7A and 7B illustrates a device for migrational chromatography with integrated microfluidics to enable automated detachment of clones of interest.
Figure 7B:
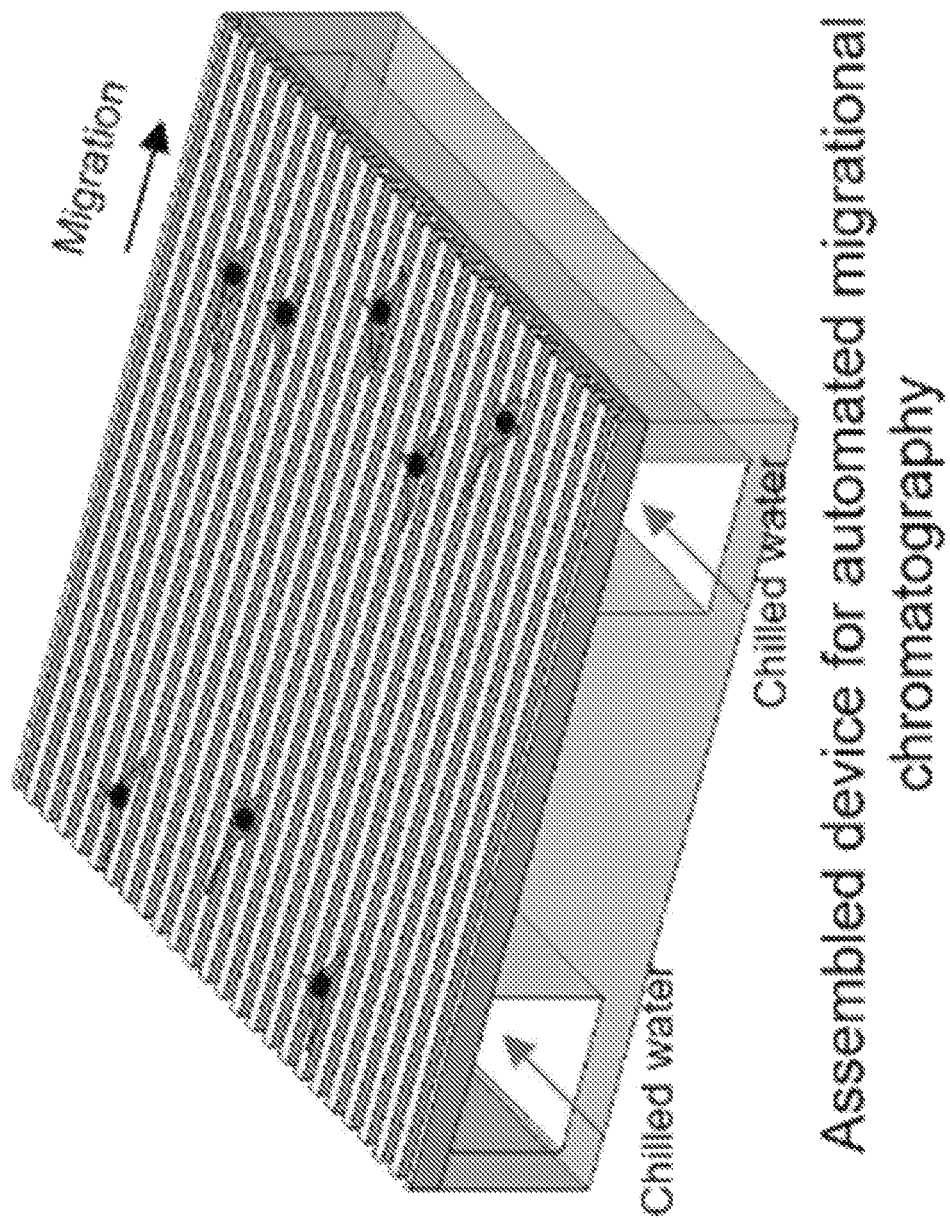
Figure 7C:
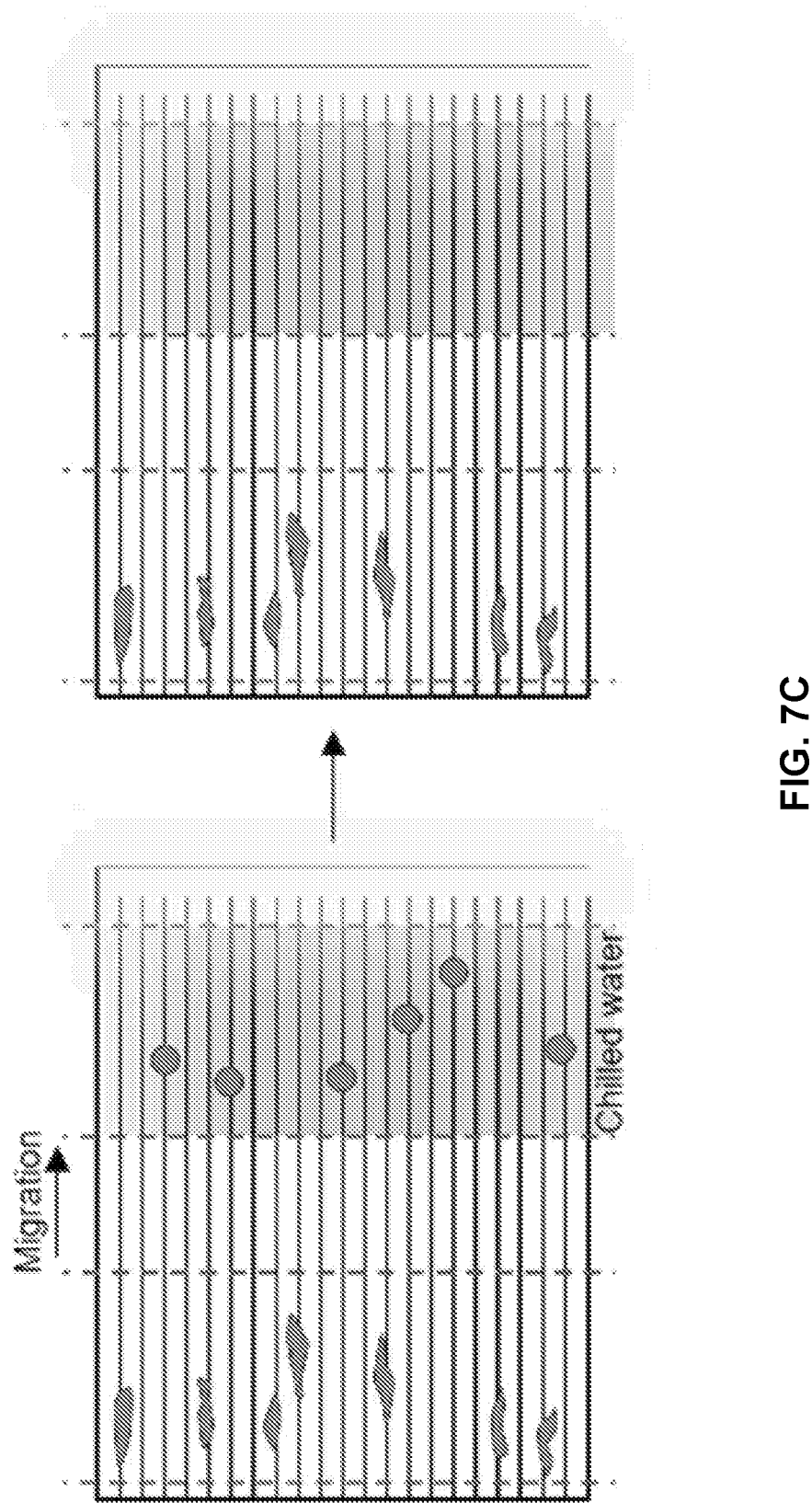
FIGS. 7C and 7D show that once migration-based separation occurs, the underlying microfluidic system can be used to sequentially flow chilled water at given locations, which facilitates selective detachment of MDSC clones of interest due to thermal actuation of the PINIPAM layer.
Figure 7D:
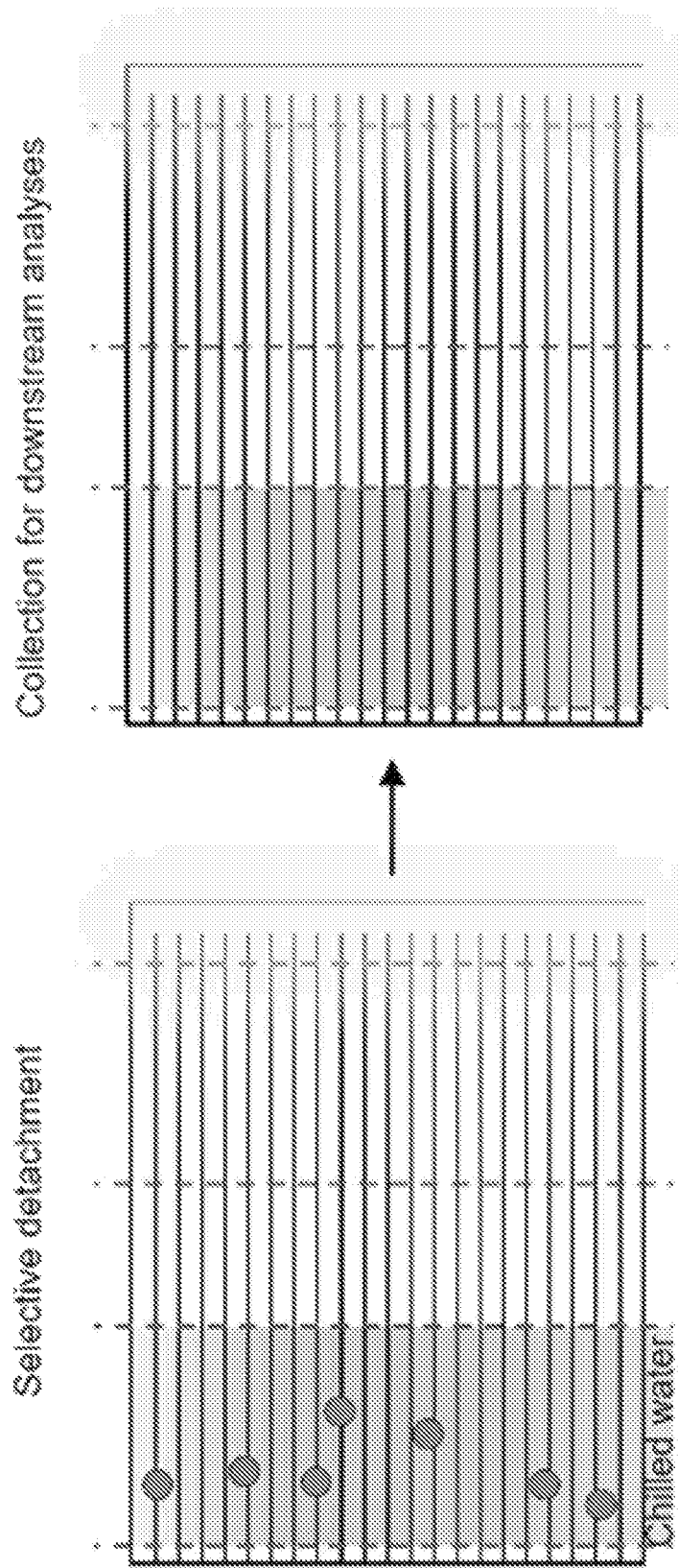

Impairing MDSC migration/infiltration into the tumor/ganglia could be a viable strategy to reduce the immunosuppressive burden. Inhibitors of Bruton's tyrosine kinase (BTK) have been commonly used in the treatment of hematologic cancers. BTK plays a role in numerous biological processes, including cell migration. While MDSCs express BTK, single-clone motility assays on TCP in the presence of ibrutinib (BTK-inhibitor) did not show a significant effect on the migration (FIG. 6). In contrast, motility assays on biomimetic surfaces appear to show selective targeting of a highly motile subset of MDSCs (FIG. 5). Such results indicate that migrationdriven changes (e.g., cytoskeletal alignment) may partly modulate drug sensitivity in MDSCs.

Example 5: Biomimetic Platforms for Migrational Chromatography

In-house nanofabrication expertise (i.e., contact/projection-based lithography, and soft-lithography) is leveraged to fabricate pre-aligned structural cues (~300 nm wide) from polydimethylsiloxane (PDMS). Textured surfaces will then be functionalized with thermoresponsive Poly(N-isopropylacrylamide) (PNIPAM) under argon plasma (30 Watts, ~1000 microTorr). The PINIPAM-coated substrates (~100 μm thick) will then be interfaced with a microfluidic system with arrayed microchannels (50 μm wide, 500 μm pitch, independently operated, FIG. 7). These channels are used to selectively flow chilled water underneath the textured PDMS and facilitate selective cell detachment via thermal activation of the PINIPAM (i.e., switch from mildly hydrophobic to highly hydrophilic). Nanotextured surfaces are characterized by scanning electron (SEM) and atomic force (AFM) microscopy. PNIPAM coating will be verified via contact angle measurements at different temperatures, X-ray photoelectron spectroscopy (XPS) and Fourier transform infrared spectroscopy (FTIR).

Example 6: MDSC Motility

MDSCs are isolated from freshly procured tissue (i.e., peripheral blood, tumor and lymphoid tissue) of breast cancer tumor patients under protocol OSU-09142 using standard procedures. Tumor cells/tissue will also be collected using standard procedures36. Migrational chromatography will be conducted on the biomimetic surfaces (FIGS. 4, 7) using GM-CSF (200 ng/mL) as chemoattractant. Singleclone migration for different source MDSCs (i.e., circulating vs. tumor- vs. lymphoid tissue-resident) are recorded via time lapse microscopy in a confocal microscope fitted with a culture chamber. Images will be collected every 10 min for 24-72h, and postprocessed/analyzed using the manual tracker plugin in Fiji. MDSC clones that exhibit different degrees of motility will be isolated by selectively "operating" the microchannels of the platform. The cells are partitioned as high- vs. medium-vs. low motility depending on the traveled distance from the starting location (FIG. 7). The biomechanics (i.e., stiffness and contractility) of these clonal subsets are then analyzed by oscillatory AFM, which is a technique developed by co-I Ghadiali to analyze viscoelastic properties of single cells, and Traction Force Microscopy (TFM), as described elsewhere. Moreover, flow cytometry is run for monocytic ($CD15^+/CD14^+$) and granulocytic ($CD15^+/CD14^-$) markers, and combinations thereof. To evaluate immunosuppressive activity in each clonal subset, they are cultured (at different concentrations) with CFSE-labeled T cells, and T cell proliferation are evaluated by flow cytometry. RMPI media alone, and SIINFEKL peptide will be used as negative and positive controls, respectively. Finally, clonal subsets with the strongest suppressive activity are further analyzed by single-cell sequencing, as described elsewhere.

Example 7: BTK Inhibition

Once highly mobile and/or immunosuppressive clones are identified from different source MDSCs, the extent to which BTK inhibitors (i.e., ibrutinib) hamper guided dissemination is evaluated. First, immunoblotting is used to evaluate the level of BTK and phosphorylated BTK (p-BTK) in each clonal subset exposed to 0-10 µM ibrutinib. Each clonal subset is then plated on the nanotextured surfaces (~$10^3$-$10^4$ cells/$cm^2$), and guided migration is monitored via time lapse microscopy while being exposed to 0-10 µM ibrutinib. Images are processed/analyzed via Fiji. Experiments with ACP-196 (selective and irreversible BTK inhibitor) and GDC-0853 (selective and reversible BTK inhibitor) are run for comparison purposes. AFM and TFM are used again to evaluate single-cell stiffness and contractility, respectively, after exposure to ibrutinib. The effects of BTK inhibition on MDSC motility and biomechanics are further evaluated in breast cancer patients receiving ibrutinib under the auspices of an OSU CCC-sponsored clinical study that is open and accruing at OSU (OSU-18015). Following the acquisition of informed consent, 30 cc of peripheral blood is drawn pre-treatment and at 2 and 4 weeks after the initiation of therapy. MDSCs are isolated and single-clone motility and biomechanics (i.e., AFM and TFM) are evaluated as described above.

Example 8: Reciprocal Modulation of MDSCs/Tumor Cell Dissemination

Figure 8A:
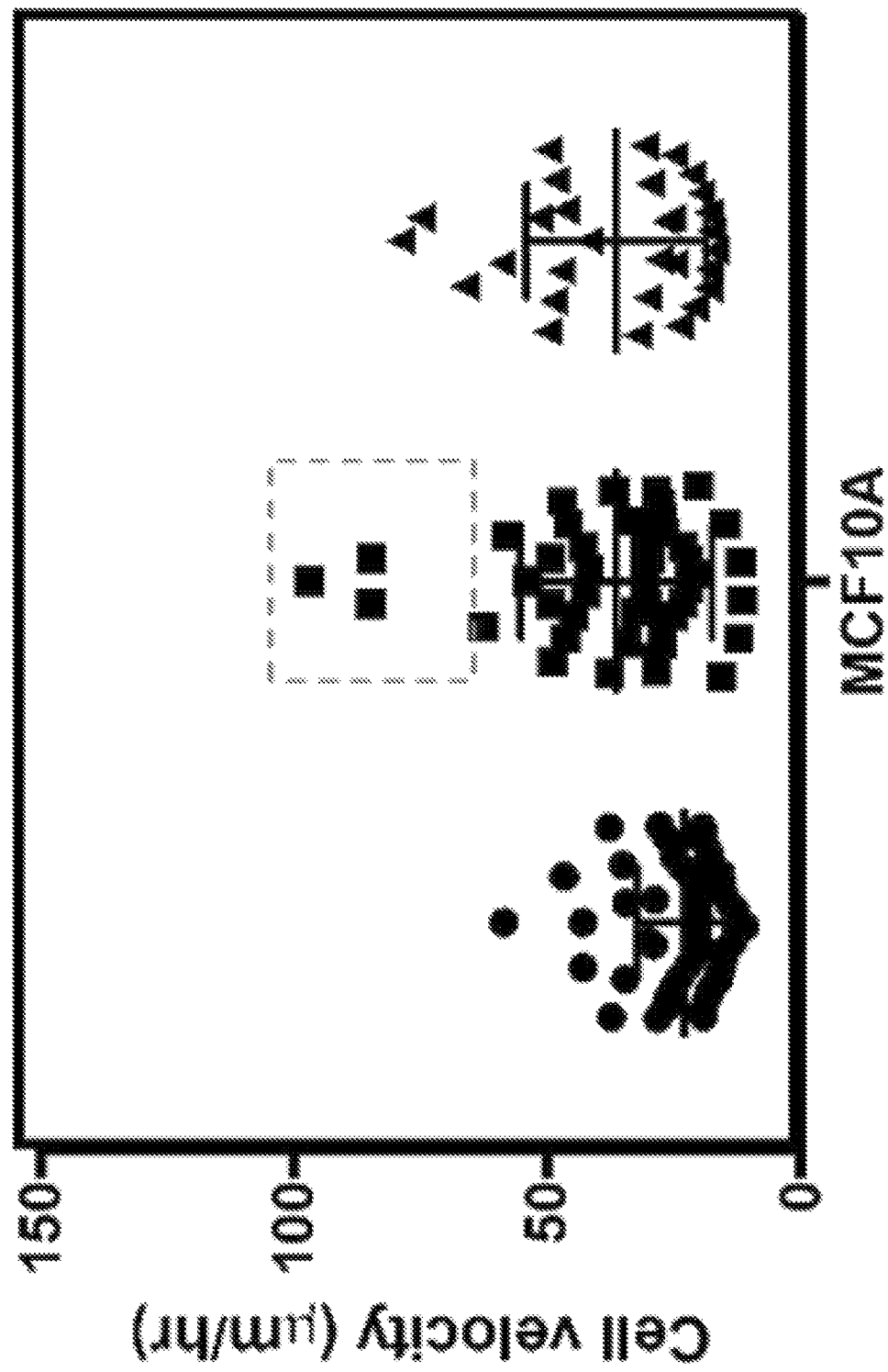
FIG. 8A shows co-culturing MDSCs and noncancerous MCF10As led to enhanced motility in a group of MCF10A clones.
Figure 8B:
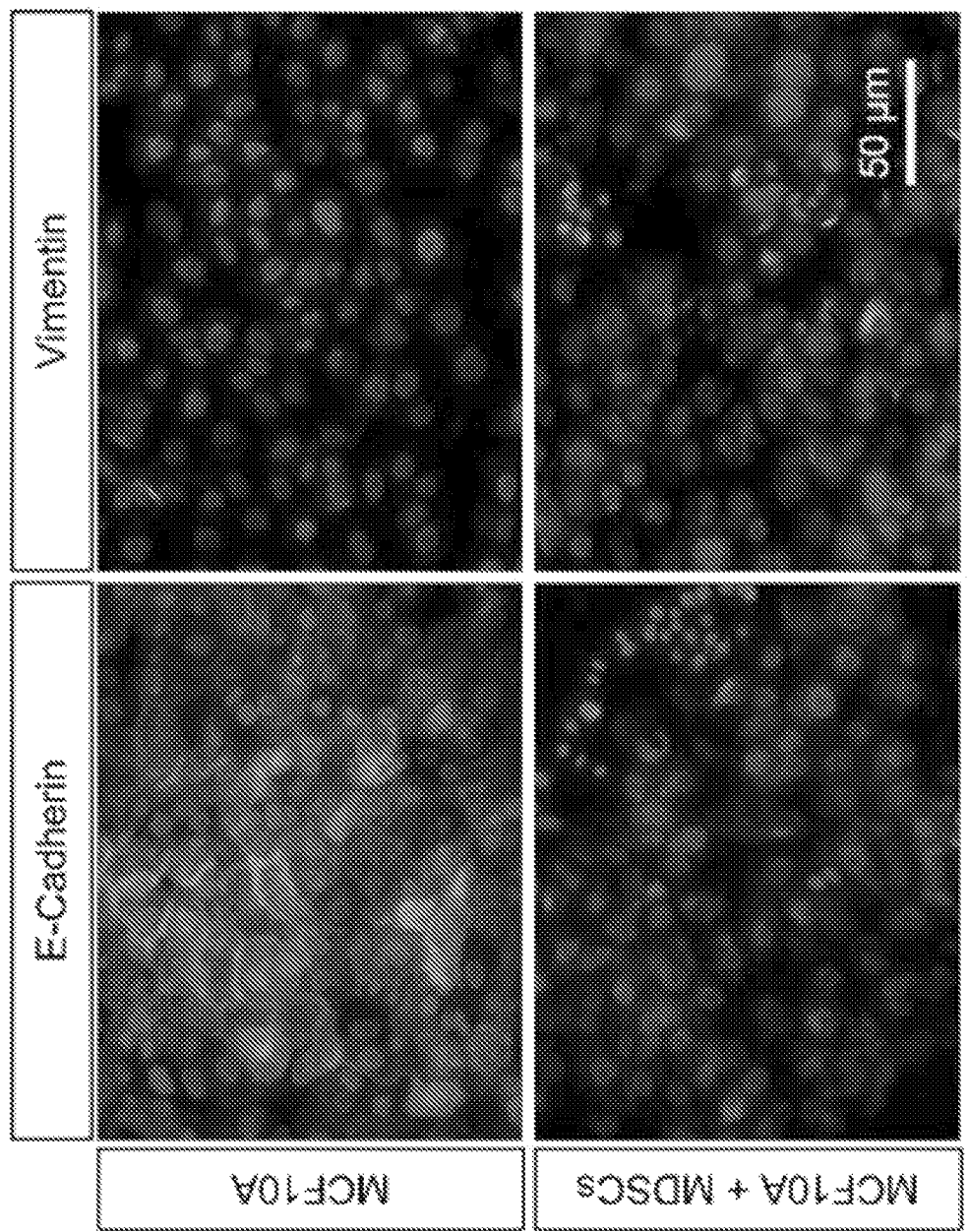
FIG. 8B shows immunofluorescence analysis indicates that coculture conditions triggered a decrease in the expression of epithelial markers such as ECadherin, and an increase in mesenchymal markers in certain clones (e.g., Vimentin).
Figure 8C:
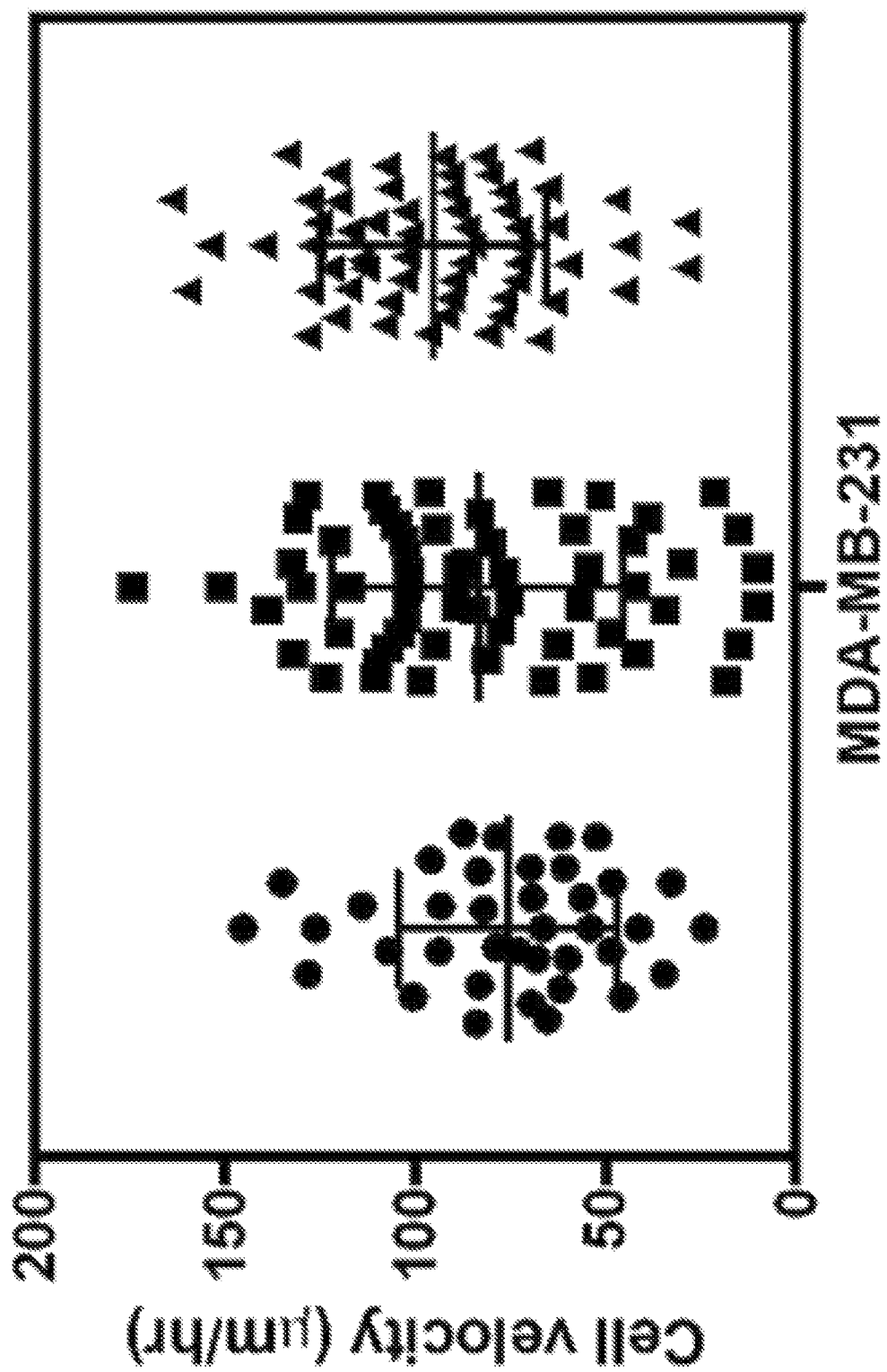
FIG. 8C shows coculturing MDSCs with already aggressive MDAMB-231 cells did not lead to major changes in motility in the MDA-MB-231 population. •: monoculture, ■: 50:50 co-culture ▲:90:10 coculture (MDSC:breast cancer/tissue cells).
Figure 9:
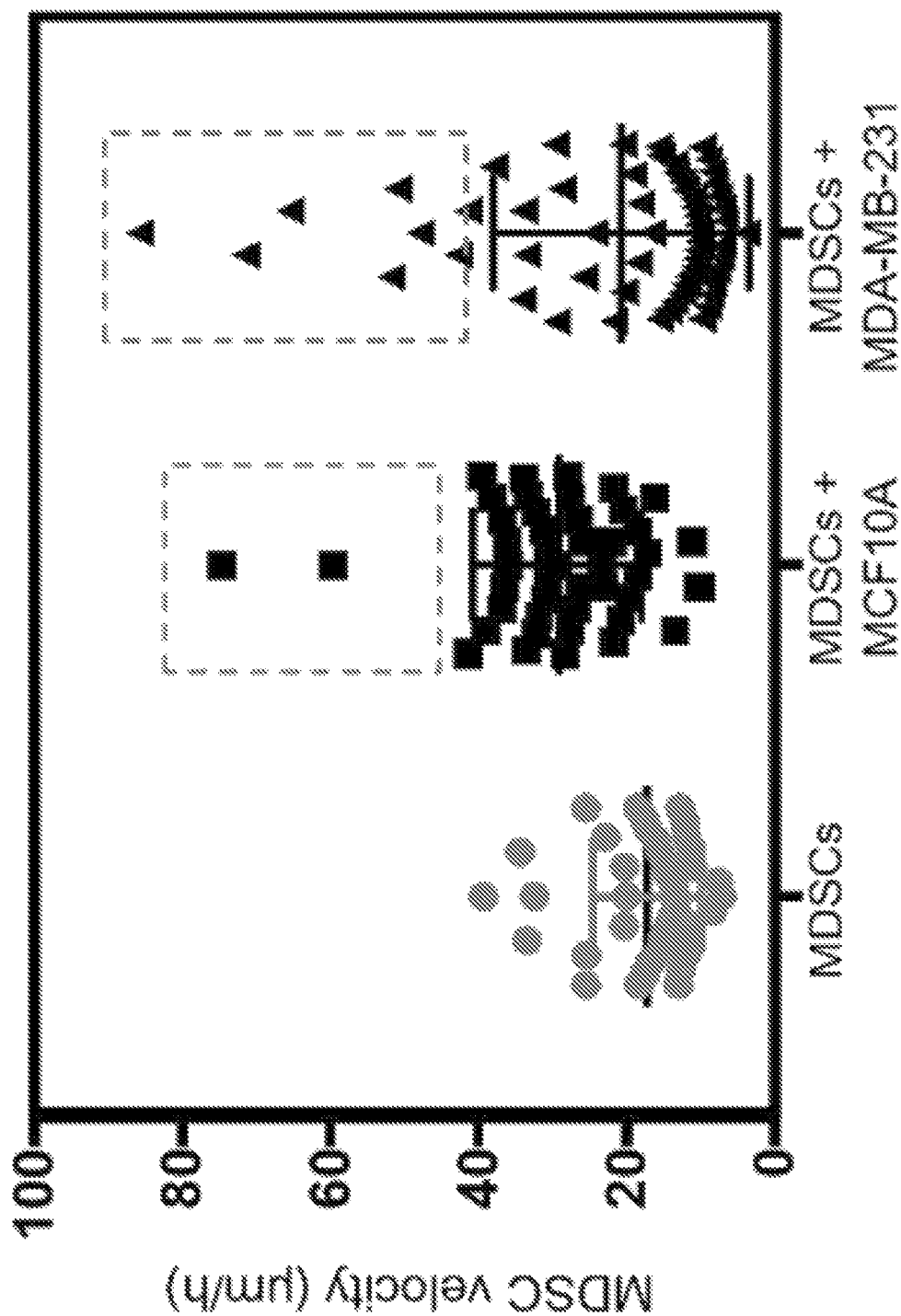
FIG. 9. Shows co-culturing MDSCs and breast tissue/cancer cells led to a marked increase in velocity for certain MDSC clones, especially when co-cultured with MDA-MB-231. These results potentially suggest that MDSC motility is positively regulated in the presence of metastatic cells, facilitating co-dissemination outside the tumor, and continued immunoprotection during the tumor cell dissemination process.

Preliminary studies indicate that MDSCs have specialized clonal subsets with improved mobility, which presumably are more prone to colonizing tumors/lymphoid tissue, or to co-disseminating along with highly invasive tumor cells to provide "protective" immunosuppression early during metastasis. Pilot studies on biomimetic surfaces (FIGS. 8-9) indicated that the presence of MDSCs triggered enhanced motility and epithelial to mesenchymal-like transitions in a clonal subset of non-cancerous breast tissue cells (FIG. 8A-8B), suggesting that MDSCs may have the ability to induce potentially cancerous transformations in healthy tissue. In contrast, MDSCs did not appear to induce significant changes in the overall motility pattern of highly aggressive breast cancer cells (FIG. 8C). Interestingly, the most aggressive tumor cells induced the strongest changes in single-clone motility in MDSCs (FIG. 9). MDSCs went from single-clone velocities that clustered around/below 40 µm/h, to velocities that could reach in some cases ~100 µm/h, likely due to enhanced cytokine/chemokine secretions from aggressive tumor cells.

Example 9: Guided Migration Studies at the Single-Clone Level Uncover Possible Targets of Therapeutic Interest in Tumor-Associated Myeloid-Derived Suppressor Cell Populations Methods Textured PDMS surfaces: microtextured PDMS surfaces were fabricated from photolithographically patterned silicon masters via a replica molding process. A parallel array of ridges and grooves (2 µm wide, 2 µm tall, spaced by 2 µm) was first patterned on a silicon master via standard UV photolithography using S1813 photoresist. A 10:1 mixture of PDMS with curing agent was then cast on the master and allowed de-gas and cure for several hours. The PDMS was then demolded from the master, sterilized and placed on multi-well plates for single-cell migration experiments. Scanning electron microscopy (SEM) was used to characterize the surface morphology.

MDSC cultures: the mouse MDSC cell line (MSC-2) was a kind donation from Gregoire Mignot. MSC-2 cells were cultured in RPMI 1640 media supplemented with 25 mM HEPES, 10% heat-inactivated fetal bovine serum (FBS), 1% antibiotic-antimycotic, and 1 mM sodium pyruvate. Patient-derived MDSCs were enriched from peripheral blood using the RosetteSep HLA-myeloid cell enrichment kit (Stemcell Technologies) followed by Ficoll-Paque centrifugation (GE healthcare). MDSC were isolated by subsequent negative selection of HLA-DRneg cells using anti-HLA-DR Micro-Beads (Miltenyi Biotec) for 15 minutes at 4° C. and isolated using a MS-MACS column. Samples were acquired with informed consent under IRB-approved protocols for human subject research.

Single-cell migration assays: Approximately $1.5 \times 10^5$ MSC-2 cells were seeded and allowed to adhere on the textured PDMS surfaces or TCP controls in regular culture media for several hours. Cells were imaged via time-lapse microscopy every 10 minutes for over 16 h using a cell culture chamber (Okolab) mounted on an inverted microscope. Images were analyzed using the manual tracker plugin in Fiji. Single-cell displacement data were then analyzed via MATLAB to determine velocities and net track traveled distances.

Flow cytometry-based analysis and sorting: the following antibodies were used for the MSC-2 cells: anti-CD11b-FITC, anti-Ly6-C-APC and anti-Ly6-G-PE, all purchased from Biolegend. For patient-derived MDSCs, we used anti-CD33-APC, anti-CD11b-AP, and anti-HLA-DR-PECy7, purchased from Beckman Coulter. Data were acquired using an LSRII flow cytometer (BD Biosciences). All colors were evaluated against their respective isotype controls and samples with no staining.

Gene expression analyses: Total RNA was extracted using the TRizol reagent (ThermoFisher). Reverse transcription reactions were performed using 500-1000 ng RNA in a 20 μl reaction with the superscript VILO cDNA synthesis kit (ThermoFisher). cDNA was used as a template to measure the expression levels of pro- and anti-inflammatory genes by quantitative real-time PCR using predesigned primers. Real-time PCR reactions were performed using the QuantStudio 3 Real-Time PCR System with TaqMan fast advance chemistry (Thermo Scientific) with the following conditions: 95° C. 10 min, 40 cycles of 95° C. 1 min, 60° C. 1 min, and 72° C. 1 min. Gene expression was normalized against the house keeping genes GAPDH and ATP-6.

Orthotopic tumor xenografts: immunodeficient nude mice (Jackson Laboratory), 6-8-week-old, were first injected with 1 million human breast cancer cells (MDA-MB-231) in the mammary fat pad to generate tumors. After 4 weeks of tumor development, sorted MDSC subpopulations were stained using PKH67 green fluorescent cell linker kit for general cell membrane labeling (Millipore Sigma) following the instructions suggested by the manufacturer. Tumor-bearing mice were then injected with approximately $2.5 \times 10^5$ MDSCs via the tail vein. The mice were then collected 1-day post-injection, and the tumors, lungs and spleens were characterized with an IVIS Imaging System (Xenogen Imaging Technologies). All animal studies were performed in accordance with protocols approved by the Laboratory Animal Care and Use Committee of The Ohio State University.

Statistical analysis: All statistical analyses were run in Sigma Plot 12 or GraphPad Prism 7. We used n=3-6 replicates per experiment. Specific information on the number replicates, statistical tests, and levels of significance can be found in the figure legends.

Results and Discussion

Figures 10A, 10B:
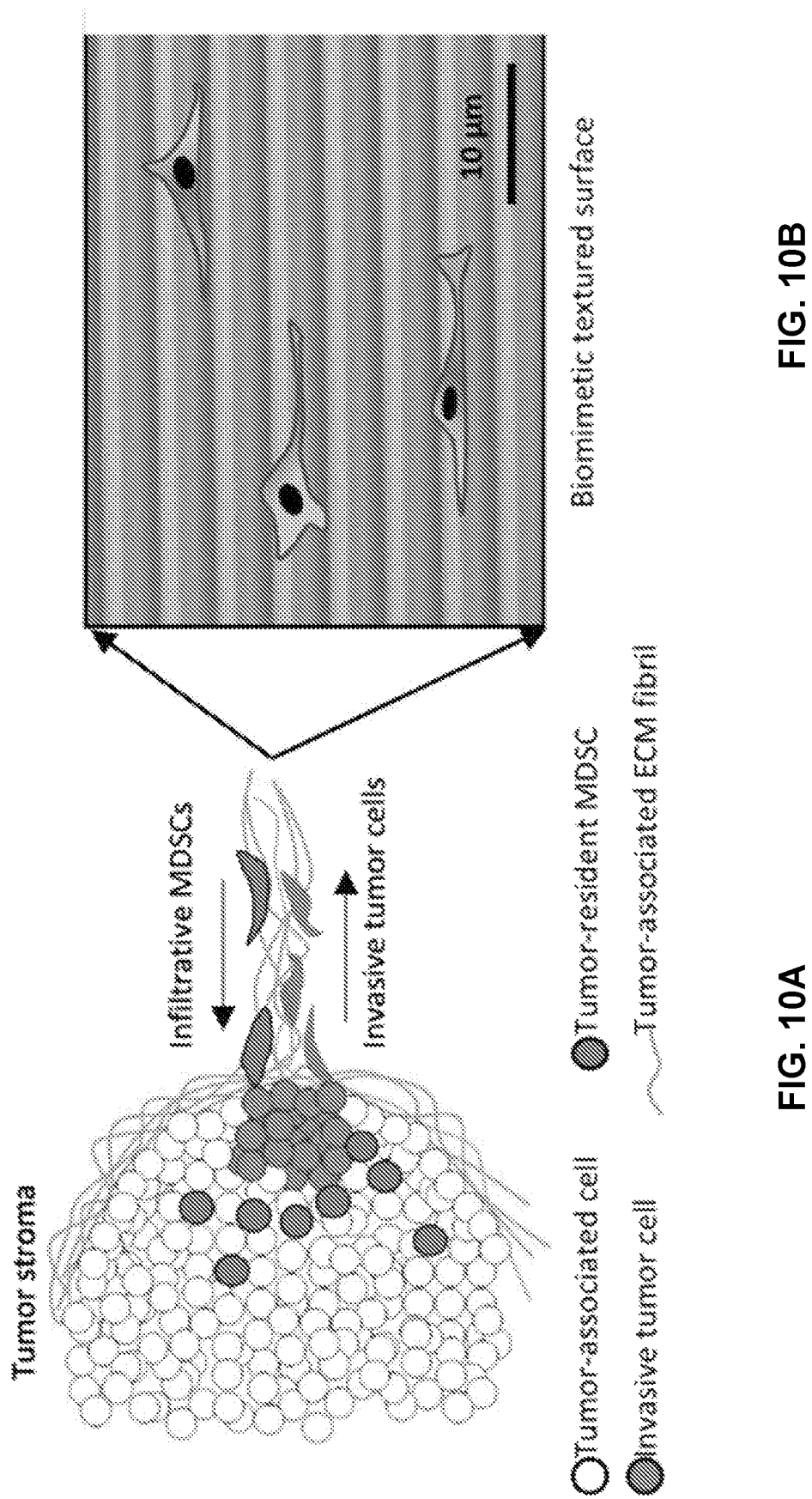
FIGS. 10A to 10E show MDSCs are responsive to aligned structural cues and exhibit guided dissemination patterns.
Figure 10C:
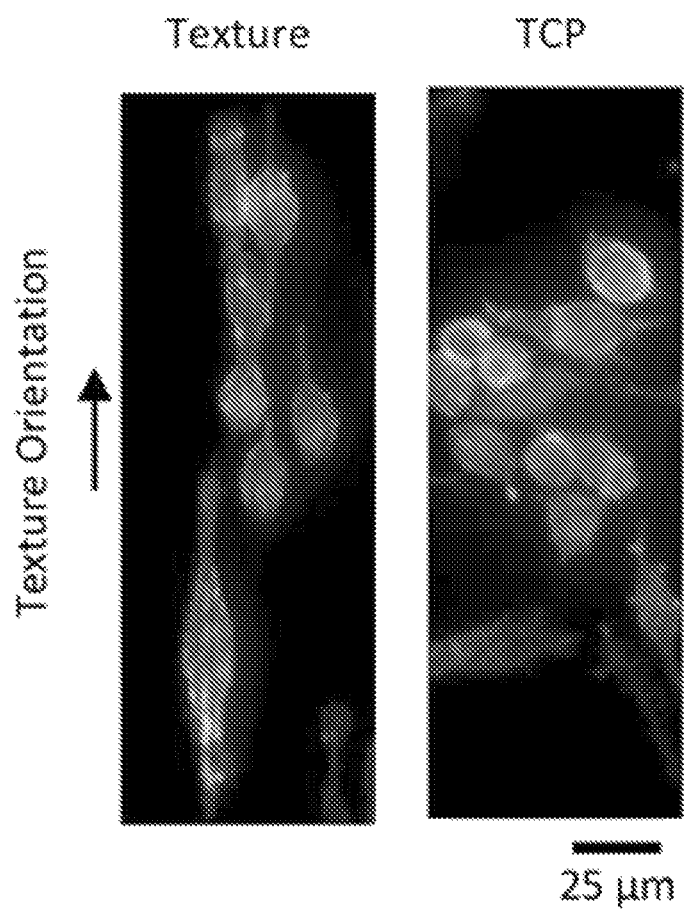
Figure 10D:
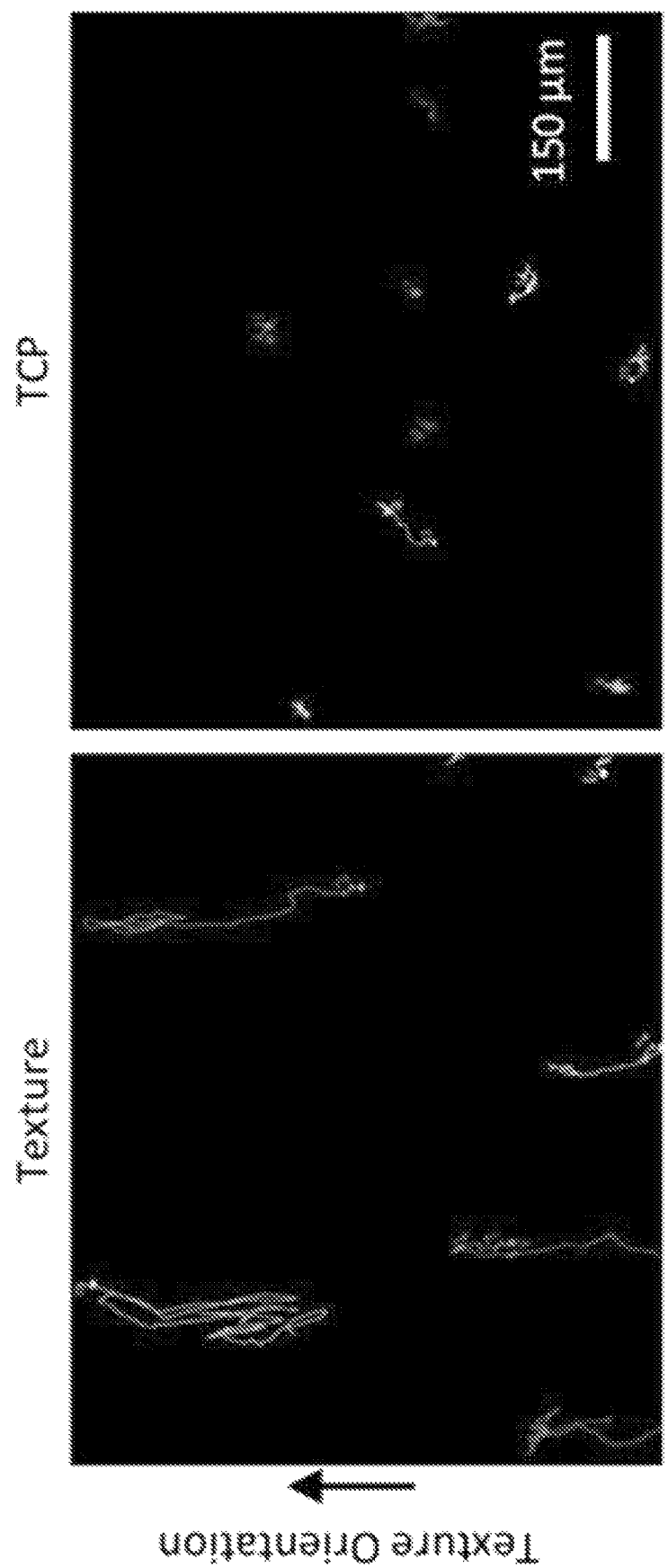
Figure 10E:
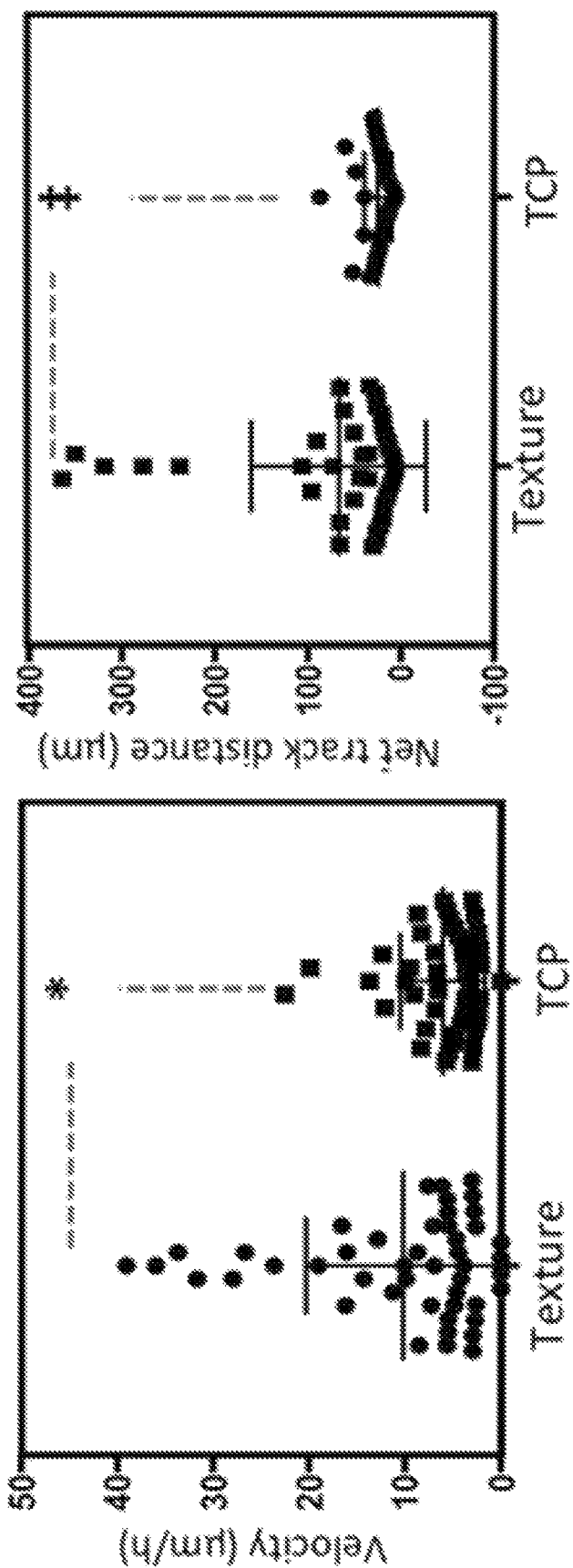
Figure 13A:
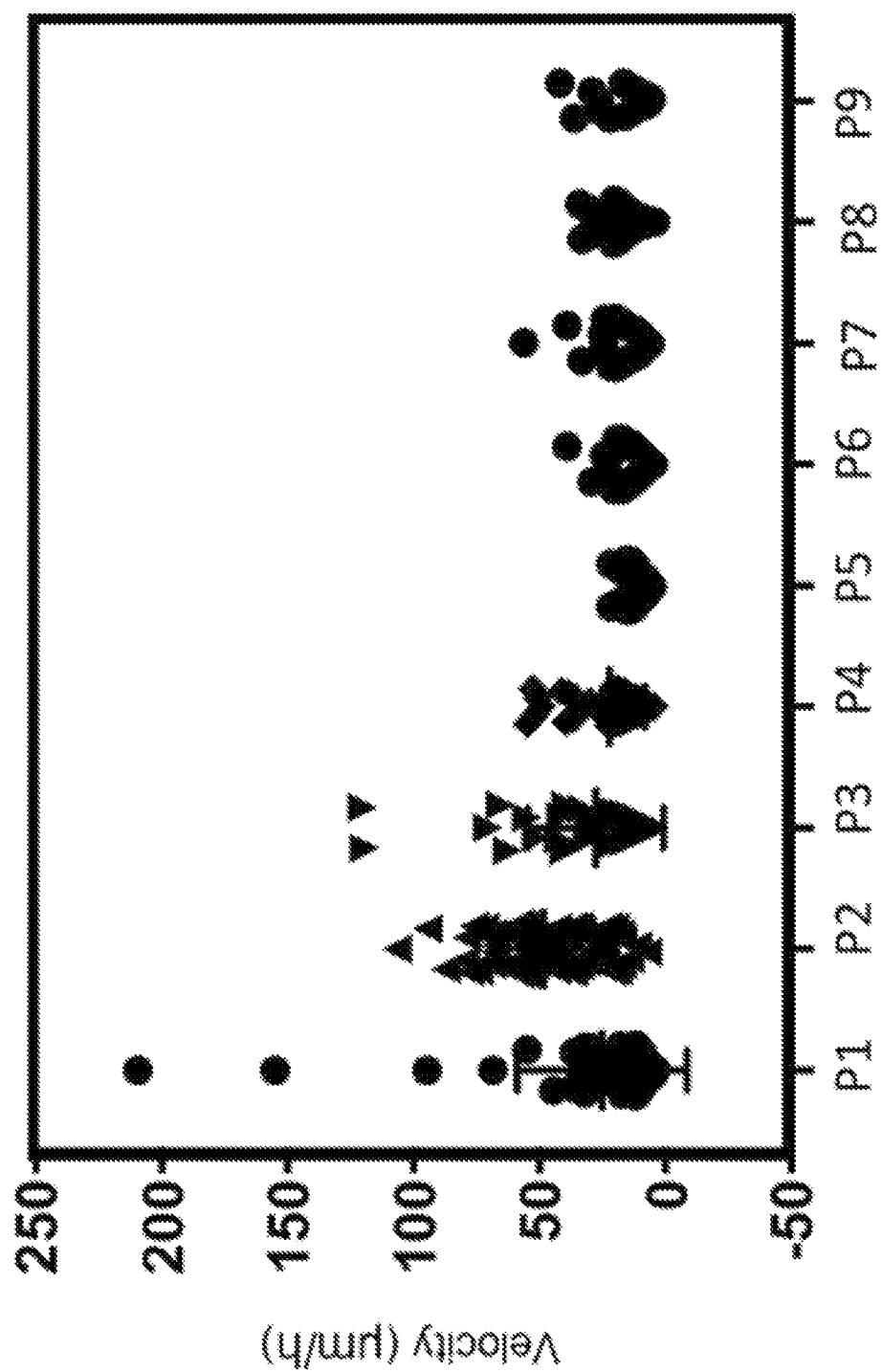
FIGS. 13A and 13B show circulating MDSCs derived from melanoma patients show different dissemination profiles at the single-clone level.
Figure 13B:
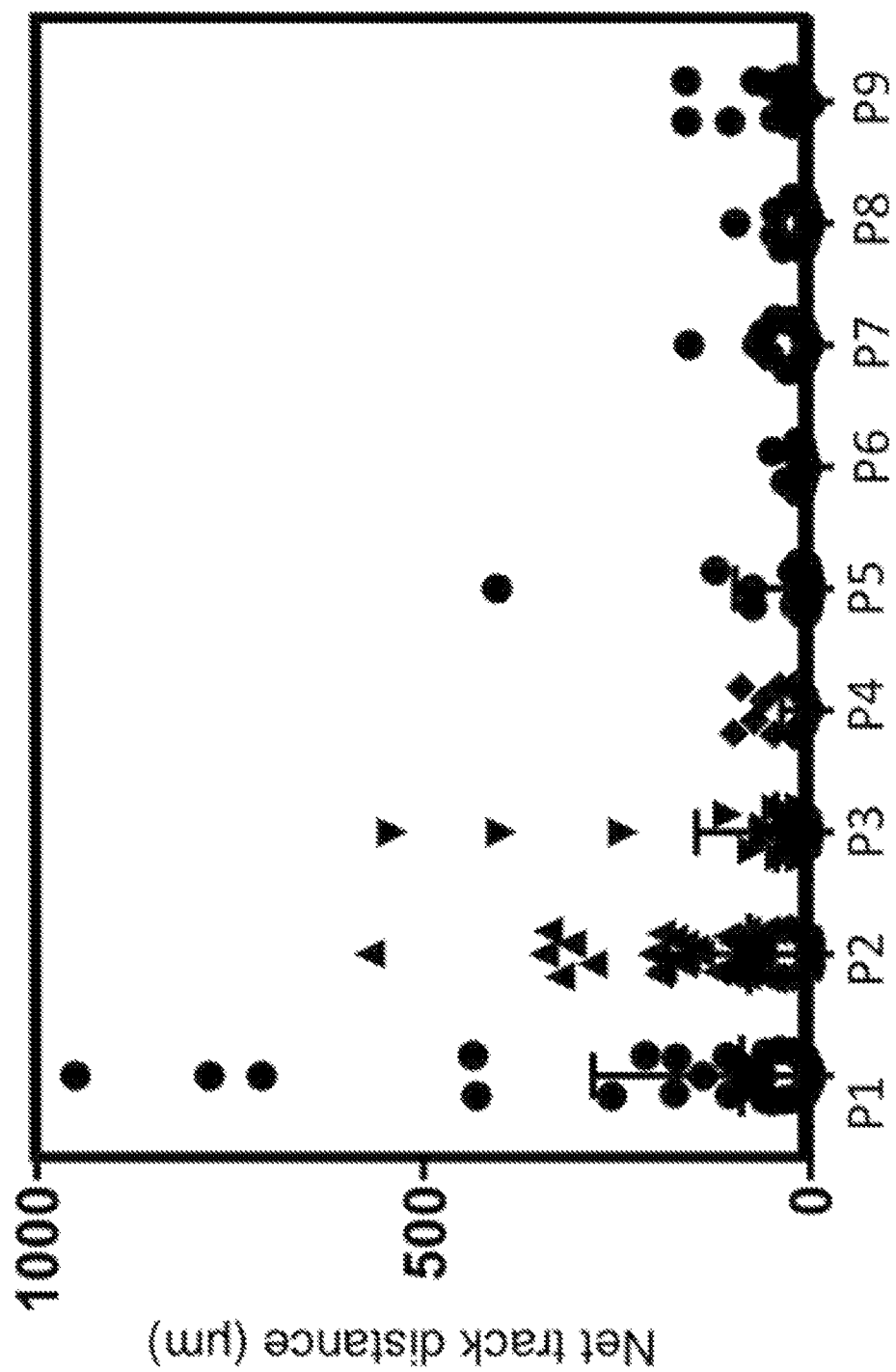
Figure 14A:
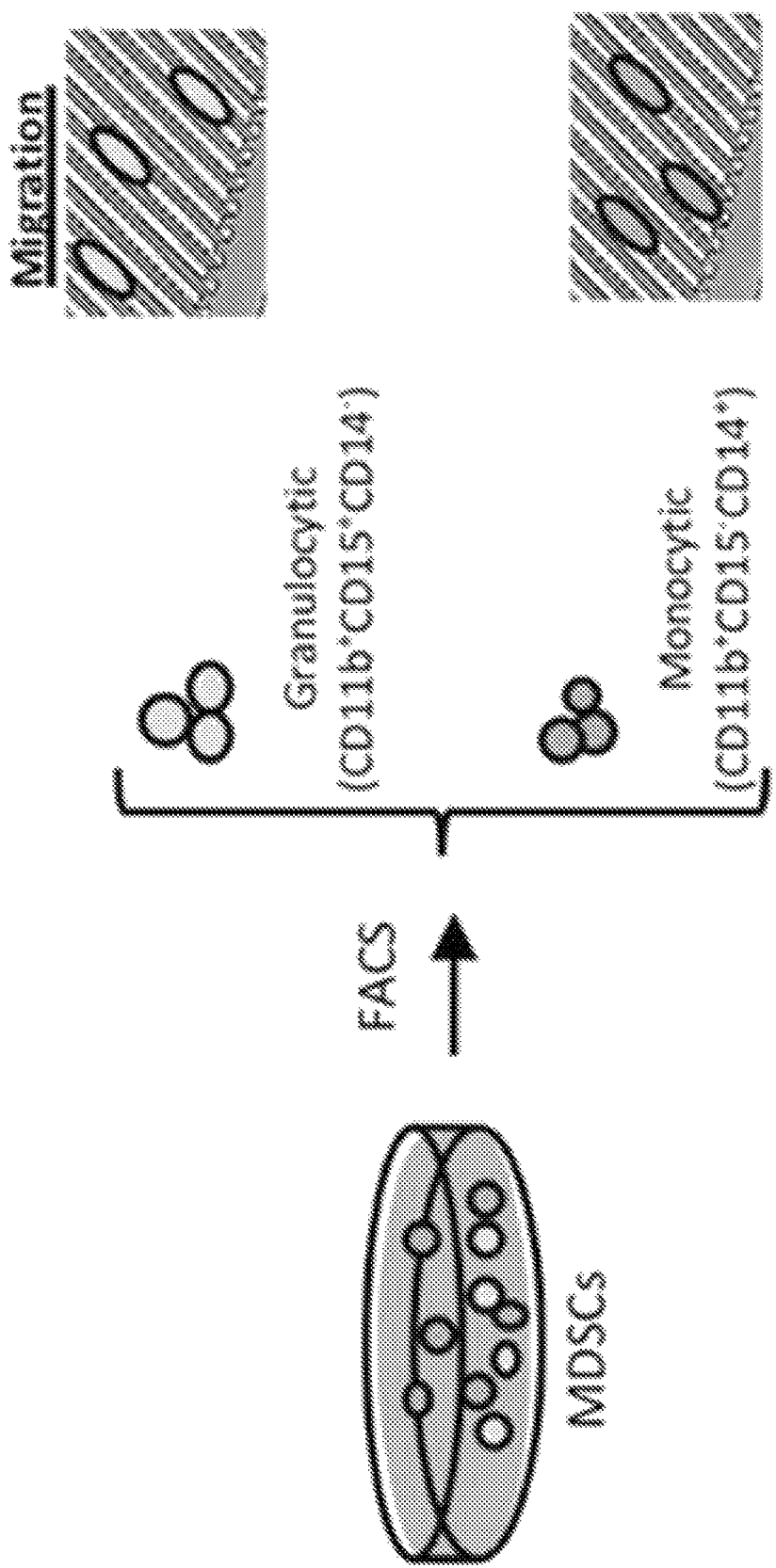
FIGS. 14A to 14F show distinct subpopulations of patient-derived MDSCs show different dissemination capabilities.
Figures 14B, 14C:
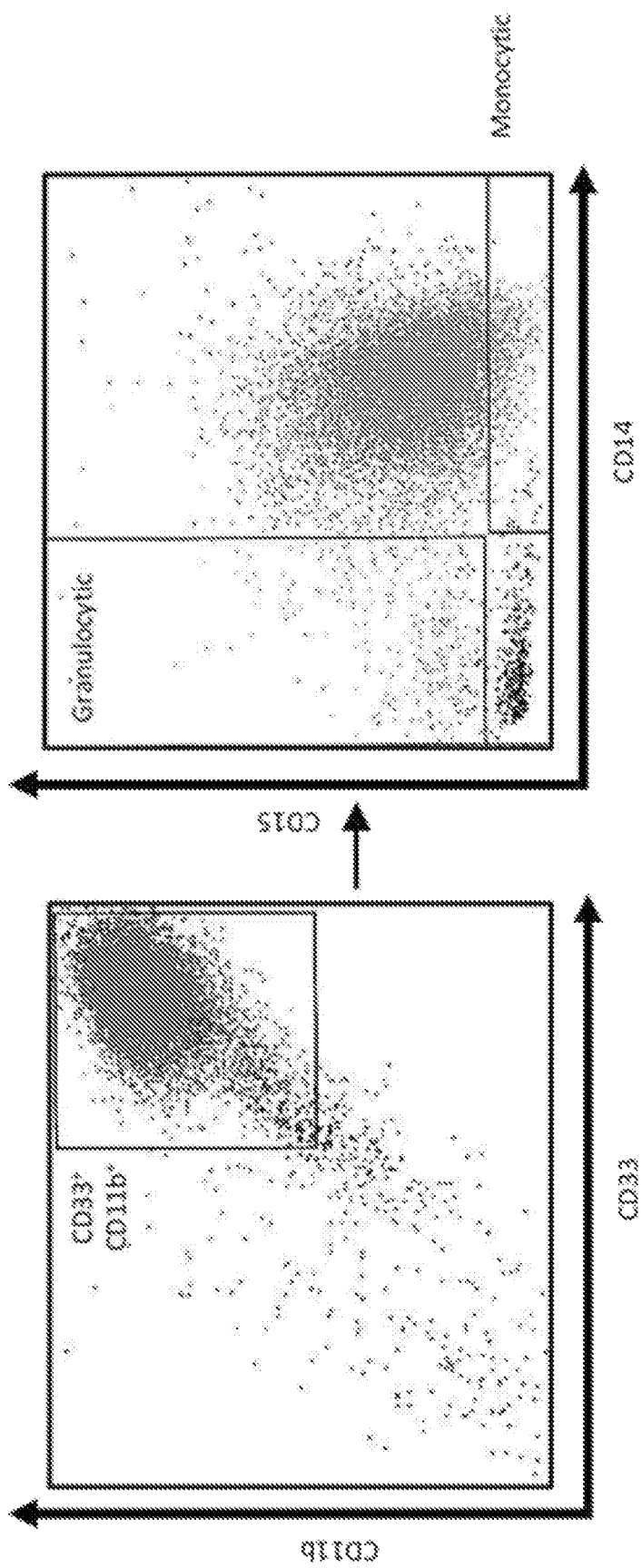
Figure 14D:
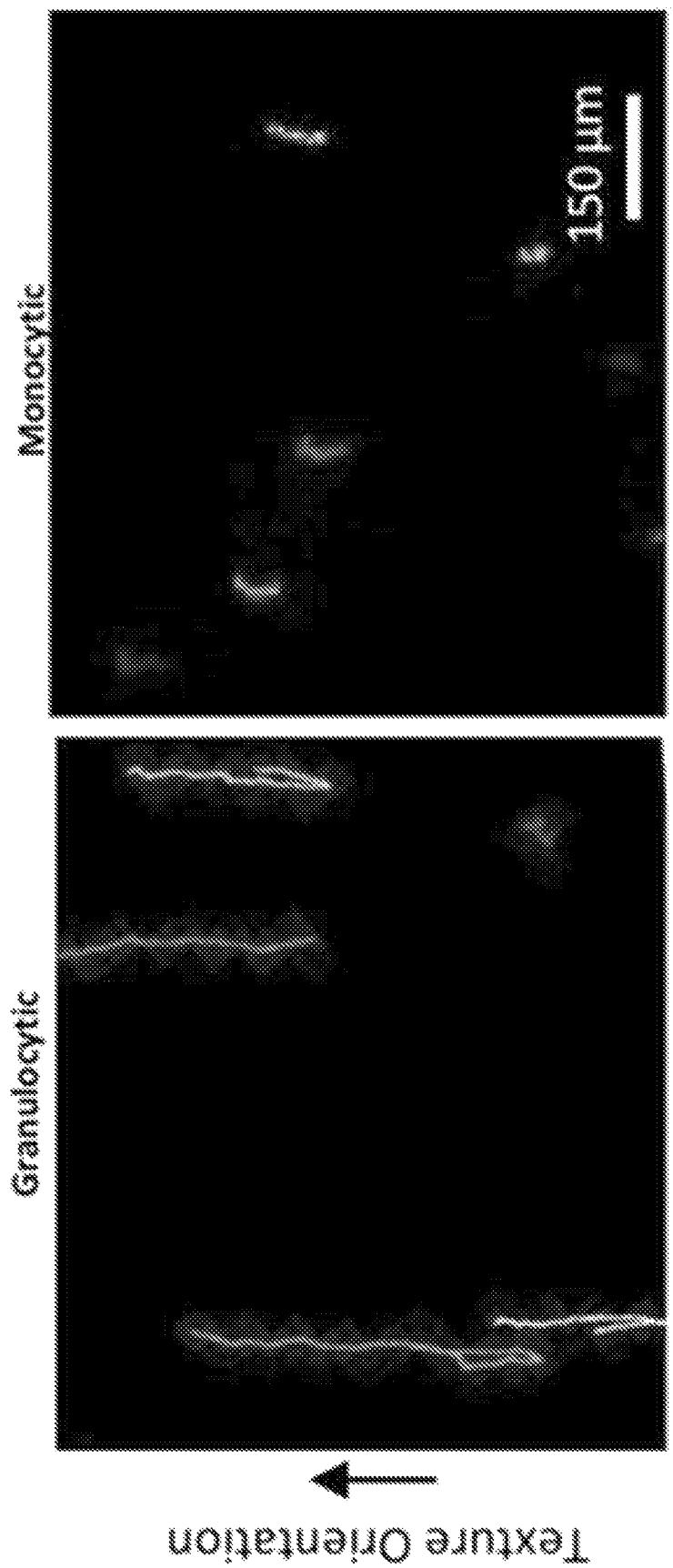
Figure 14F:
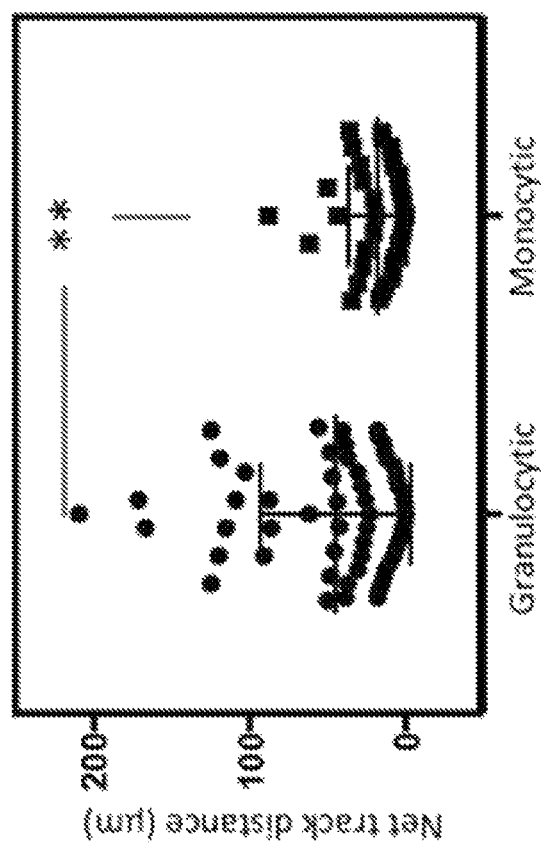
Figure 14E:
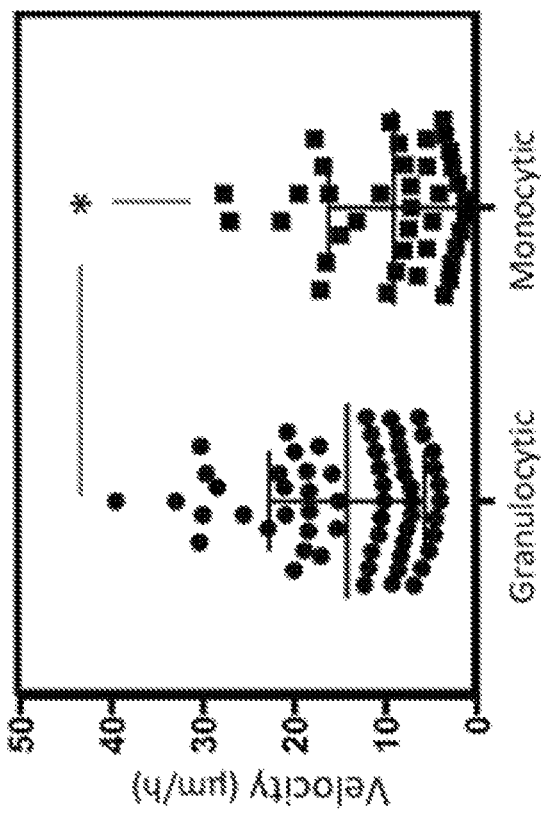

MDSCs respond to topographical cues and exhibit structurally guided dissemination patterns. Structurally guided cell dissemination has been known to play a role in the escape of cancerous cells from the primary tumor and the establishment of metastatic outgrowths in peripheral organs and tissues. Highly aggressive cancer cells tend to exhibit distinct spreading patterns, disseminating preferentially along pre-aligned anatomical microstructures within the tissues, including radially oriented fibrils from the extracellular matrix (ECM), white matter tracts, the basal lamina of blood vessels, and the subpial/subperitoneal spaces, among others (FIG. 10A) (Gallego-Perez D, et al. Lab Chip 2012, 12:4424-4432; Bellail A C, et al. Int J Biochem Cell Biol 2004, 36:1046-1069; Johnson J, et al. Tissue Eng Part C Methods 2009, 15:531-540). Micro- and nanoscale tools have been used to develop systems that can be utilized to probe cancer cell motility under these physiologically relevant conditions (Gallego-Perez D, et al. Lab Chip 2012, 12:4424-4432; Bellail A C, et al. Int J Biochem Cell Biol 2004, 36:1046-1069; Johnson J, et al. Tissue Eng Part C Methods 2009, 15:531-540; Irimia D, et al. Integr Biol (Camb) 2009, 1:506-512; Doyle A D, et al. J Cell Biol 2009, 184:481-490; Petrie R J, et al. Nat Rev Mol Cell Biol 2009, 10:538-549). While topographical or cell confinement cues have been used to mimic rapid and highly directional motility in a wide variety of cancerous cells (Gallego-Perez D, et al. Lab Chip 2012, 12:4424-4432; Johnson J, et al. Tissue Eng Part C Methods 2009, 15:531-540; Irimia D, et al. Integr Biol (Camb) 2009, 1:506-512; Sidani M, et al. J Mammary Gland Biol Neoplasia 2006, 11:151-163; Provenzano P P, et al. BMC Med 2006, 4:38; Wong I Y, et al. Nat Mater 2014, 13:1063-1071), no studies have looked into the influence of such cues on the dissemination/infiltration capabilities of tumor-associated MDSCs. Next tested was whether MDSCs respond to topographical cues by exhibiting structurally guided dissemination patterns similar to invasive cancerous cells. The murine MDSC cell line, MSC-2, was used as a model (Stiff A, et al. Cancer Res 2016, 76:2125-2136; Trikha P, et al. Oncoimmunology 2016, 5:e1214787). These cells were plated on microtextured polydimethylsiloxane (PDMS) surfaces (FIG. 10B), which were fabricated via replica molding from photolithographically fabricated silicon masters, and were designed as an array of parallel ridges and grooves with dimensions that have been previously tested in cancer cell dissemination studies (approximately 2 μm×2 μm with 2 μm spacing) (Gallego-Perez D, et al. Nano Lett 2016, 16:5326-5332; Gallego-Perez D, et al. Lab Chip 2012, 12:4424-4432; Kim S H, et al. Cancer Cell 2016, 29:201-213; Gu S Q, et al. Nucleic Acids Res 2016, 44:5811-5819). MDSC motility was monitored at the single-clone level in real time via time-lapse microscopy. Cells plated on a standard cell culture surface (i.e., tissue culture polystyrene or TCP) were used for comparison purposes. The results indicate that MDSCs show limited motility at the single-clone level on TCP (FIG. 10C-10E), with most cells exhibiting a rounded morphology (FIG. 10C). Textured surfaces, on the other hand, clearly induced cytoskeletal and morphological rearrangements (i.e., alignment) in some of the MDSCs (FIG. 10C), which were conducive to increased motility (FIG. 10D, 10E). Average single-clone velocities reached a maximum of approximately 40 μm $h^{-1}$ on textured surfaces compared to approximately 20 μm $h^{-1}$ on TCP. Net track distances, which are a measure of the effective displacement of a single clone, reached a maximum of approximately 400 μm over a period of 16 hours on textured surfaces compared to <100 μm on TCP. Notably, MDSCs migrating on textured surfaces exhibited significant inter-clonal variability in the dissemination potential, with cells spanning the whole spectrum from low to high motility. In contrast, MDSCs migrating on TCP showed markedly less inter-clonal variability. Studies with circulating MDSCs derived from cancer patients (FIG. 13) further confirmed the existence of highly motile MDSC populations exhibiting marked inter-clonal variability, with some clones showing average guided migration velocities of up to approximately 200 μm $h^{-1}$, and total net displacements that approached 1 mm over a period of 16 hours. However, certain populations of patient-derived circulating MDSCs exhibited limited overall motility, which could potentially be a direct reflection of the underlying malignancy (e.g., type, stage, mutations) and/or concurrent treatment modalities (Tables 1-3).

TABLE 1

Backaround information for MDSC samples obtained from cancer patients.

| Patient ID | Malignancy | Stage | Mutation | Therapy |
|---|---|---|---|---|
| P1 | Melanoma | IIIC | +BRAF V600 | Nivolumab Surgery |
| P2 | Melanoma | IV | −BRAF | Nivolumab |
| P3 | Melanoma | IV | +BRAF V600 | Radiation Pembrolizumab |

TABLE 1-continued

Backaround information for MDSC samples obtained from cancer patients.

| Patient ID | Malignancy | Stage | Mutation | Therapy |
|---|---|---|---|---|
| P4 | Melanoma | IV | −BRAF | Nivolumab Ipilimumab |
| P5 | Melanoma | IV | BRAF unknown | Pembrolizumab Ipilimumab Nivolumab |
| P6 | Melanoma | IV | +BRAF V600 | IFN-Alpha |
| P7 | Melanoma | IV | NA | Leukine Nivolumab |
| P8 | Melanoma | IIB | NA | Nivolumab |
| P9 | Melanoma | IIB | NA | Nivolumab |

TABLE 2

Single-clone velocity comparisons across patients (One-way ANOVA/Tukey).

| Patient comparison | Significantly different? | p value |
|---|---|---|
| P1 vs. P2 | Yes | <0.0001 |
| P1 vs. P3 | No | 0.9993 |
| P1 vs. P4 | No | 0.9967 |
| P1 vs. P5 | No | 0.0582 |
| P1 vs. P6 | Yes | 0.0423 |
| P1 vs. P7 | No | 0.2149 |
| P1 vs. P8 | No | 0.6429 |
| P1 vs. P9 | No | 0.7526 |
| P2 vs. P3 | Yes | <0.0001 |
| P2 vs. P4 | Yes | <0.0001 |
| P2 vs. P5 | Yes | <0.0001 |
| P2 vs. P6 | Yes | <0.0001 |
| P2 vs. P7 | Yes | <0.0001 |
| P2 vs. P8 | Yes | <0.0001 |
| P2 vs. P9 | Yes | <0.0001 |
| P3 vs. P4 | No | 0.9104 |
| P3 vs. P5 | Yes | 0.0181 |
| P3 vs. P6 | Yes | 0.0121 |
| P3 vs. P7 | No | 0.0748 |
| P3 vs. P8 | No | 0.3195 |
| P3 vs. P9 | No | 0.4792 |
| P4 vs. P5 | No | 0.3736 |
| P4 vs. P6 | No | 0.3870 |
| P4 vs. P7 | No | 0.7764 |
| P4 vs. P8 | No | 0.9859 |
| P4 vs. P9 | No | 0.9795 |
| P5 vs. P6 | No | >0.9999 |
| P5 vs. P7 | No | 0.9976 |
| P5 vs. P8 | No | 0.9122 |
| P5 vs. P9 | No | 0.9972 |
| P6 vs. P7 | No | 0.9998 |
| P6 vs. P8 | No | 0.9516 |
| P6 vs. P9 | No | 0.9996 |
| P7 vs. P8 | No | 0.9992 |
| P7 vs. P9 | No | >0.9999 |
| P8 vs. P9 | No | >0.9999 |

TABLE 3

Single-clone net track distance comparisons across patients (One-way ANOVA/Tukey).

| Patient comparison | Significantly different? | p value |
|---|---|---|
| P1 vs. P2 | No | 0.9996 |
| P1 vs. P3 | No | 0.2711 |
| P1 vs. P4 | Yes | 0.0017 |
| P1 vs. P5 | Yes | 0.0474 |
| P1 vs. P6 | Yes | 0.0005 |
| P1 vs. P7 | Yes | 0.0026 |
| P1 vs. P8 | Yes | 0.0005 |
| P1 vs. P9 | No | 0.5859 |
| P2 vs. P3 | No | 0.5493 |
| P2 vs. P4 | Yes | 0.0071 |
| P2 vs. P5 | No | 0.1324 |
| P2 vs. P6 | Yes | 0.0023 |
| P2 vs. P7 | Yes | 0.0104 |
| P2 vs. P8 | Yes | 0.0022 |
| P2 vs. P9 | No | 0.8158 |
| P3 vs. P4 | No | 0.8720 |
| P3 vs. P5 | No | 0.9957 |
| P3 vs. P6 | No | 0.7667 |
| P3 vs. P7 | No | 0.9140 |
| P3 vs. P8 | No | 0.7310 |
| P3 vs. P9 | No | >0.9999 |
| P4 vs. P5 | No | 0.9999 |
| P4 vs. P6 | No | >0.9999 |
| P4 vs. P7 | No | >0.9999 |
| P4 vs. P8 | No | >0.9999 |
| P4 vs. P9 | No | 0.97777 |
| P5 vs. P6 | No | 0.9991 |
| P5 vs. P7 | No | >0.9999 |
| P5 vs. P8 | No | 0.9981 |
| P5 vs. P9 | No | 0.9995 |
| P6 vs. P7 | No | >0.9999 |
| P6 vs. P8 | No | >0.9999 |
| P6 vs. P9 | No | 0.9518 |
| P7 vs. P8 | No | >0.9999 |
| P7 vs. P9 | No | 0.9870 |
| P8 vs. P9 | No | 0.9379 |

Figures 11A, 11B:
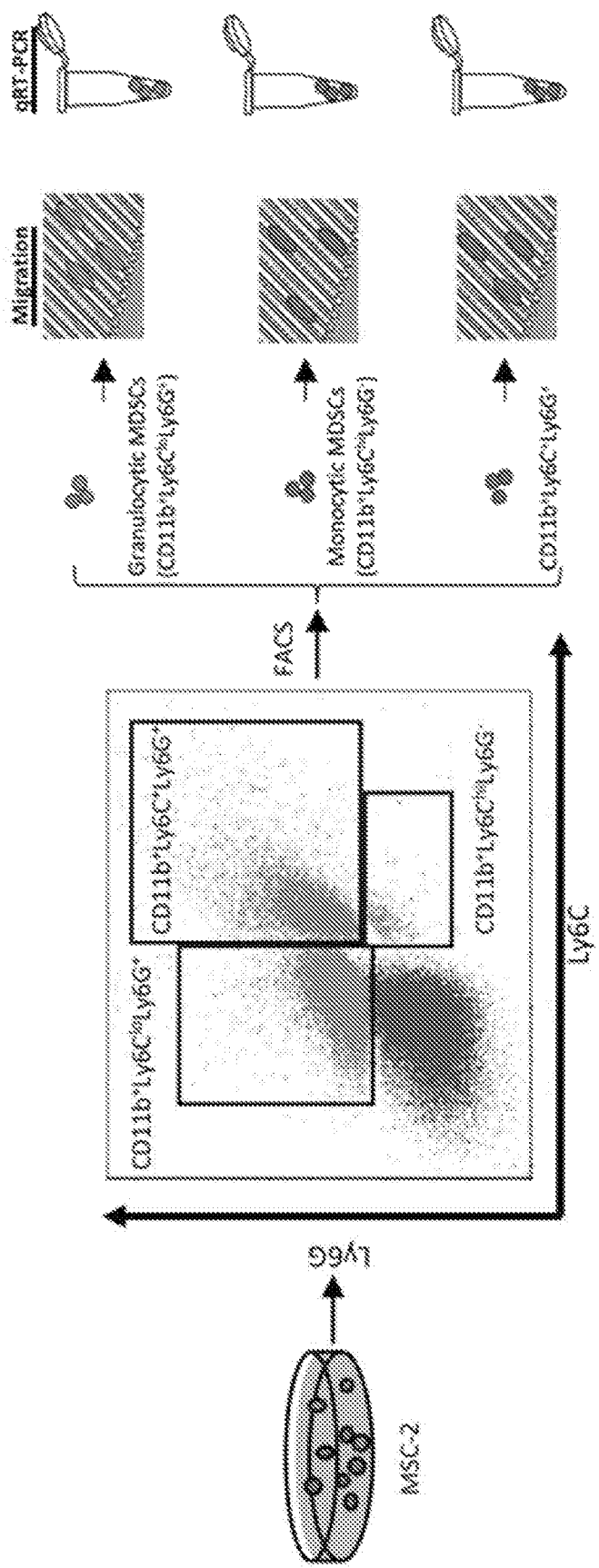
FIGS. 11A to 11I show MDSCs subpopulations exhibit distinct dissemination and gene expression patterns.
Figure 11C:
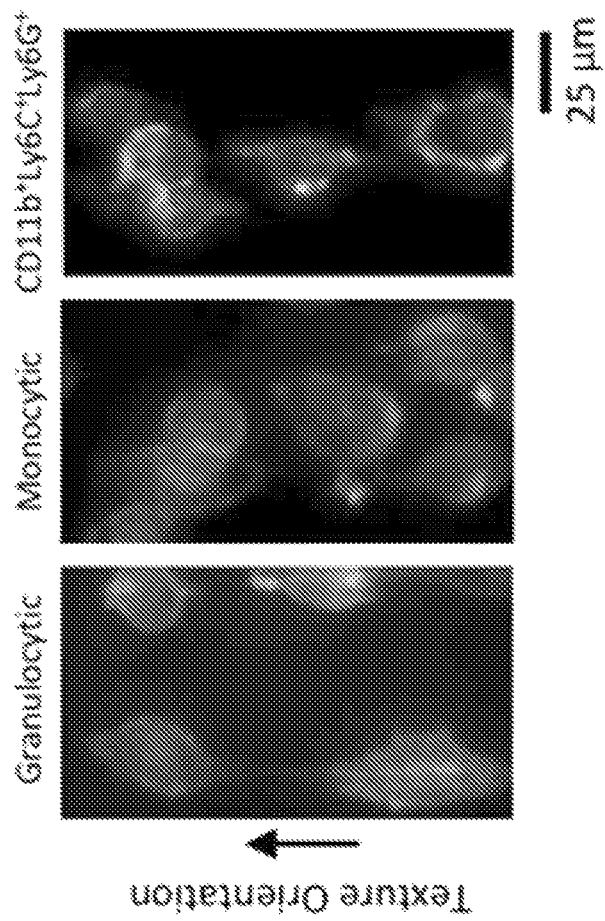
Figure 11D:
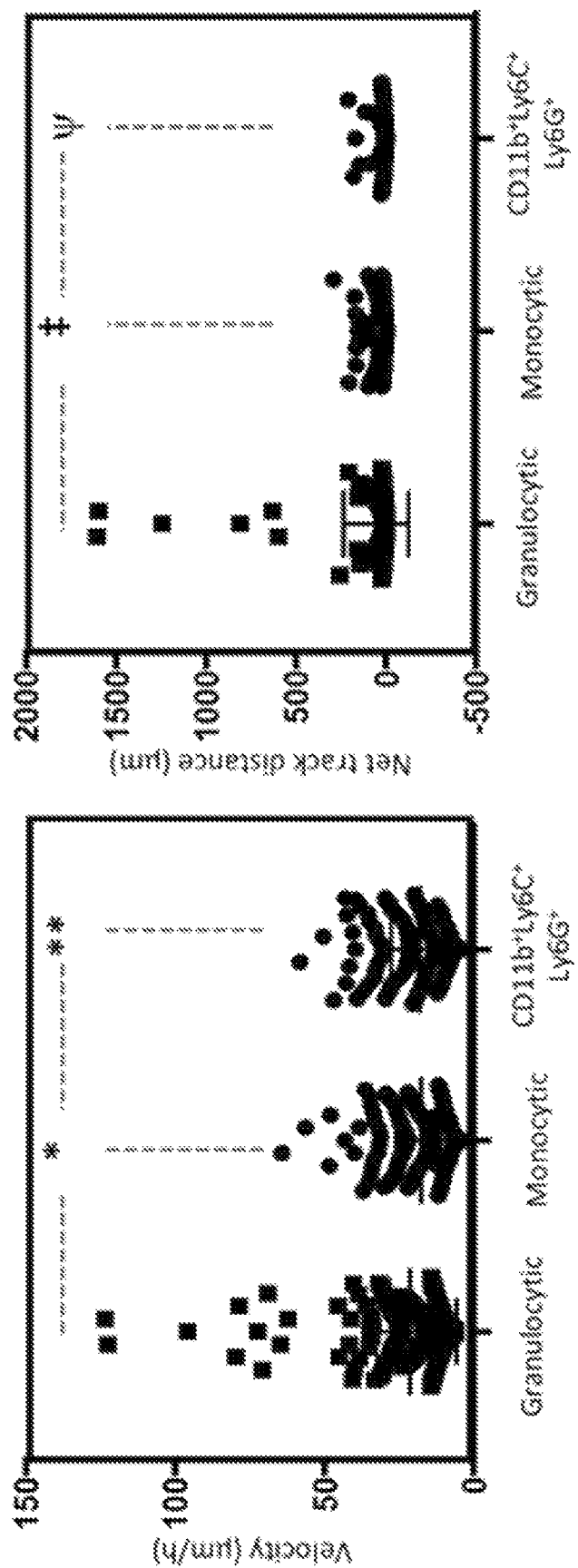
Figure 11E:
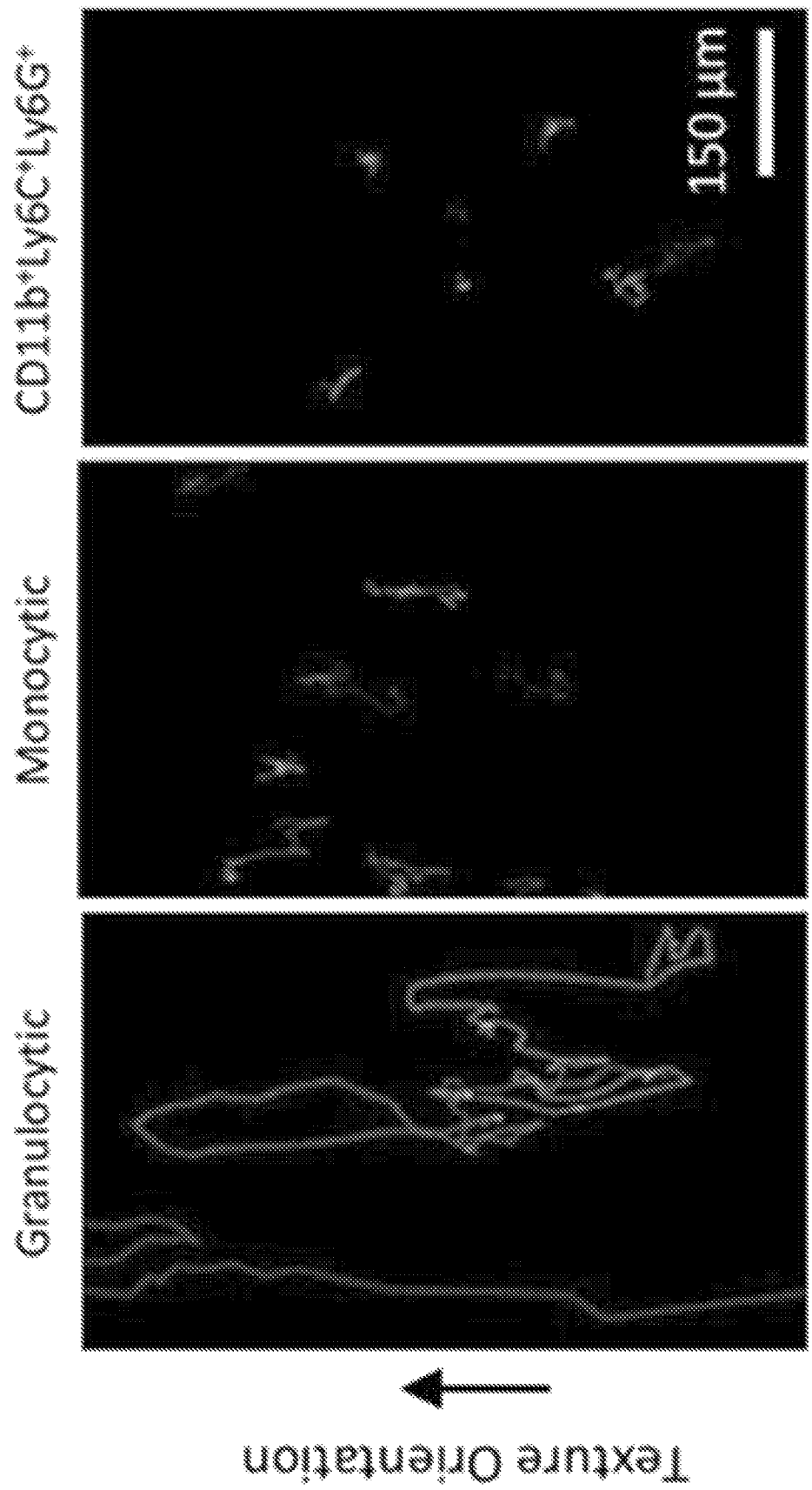
Figure 11F:
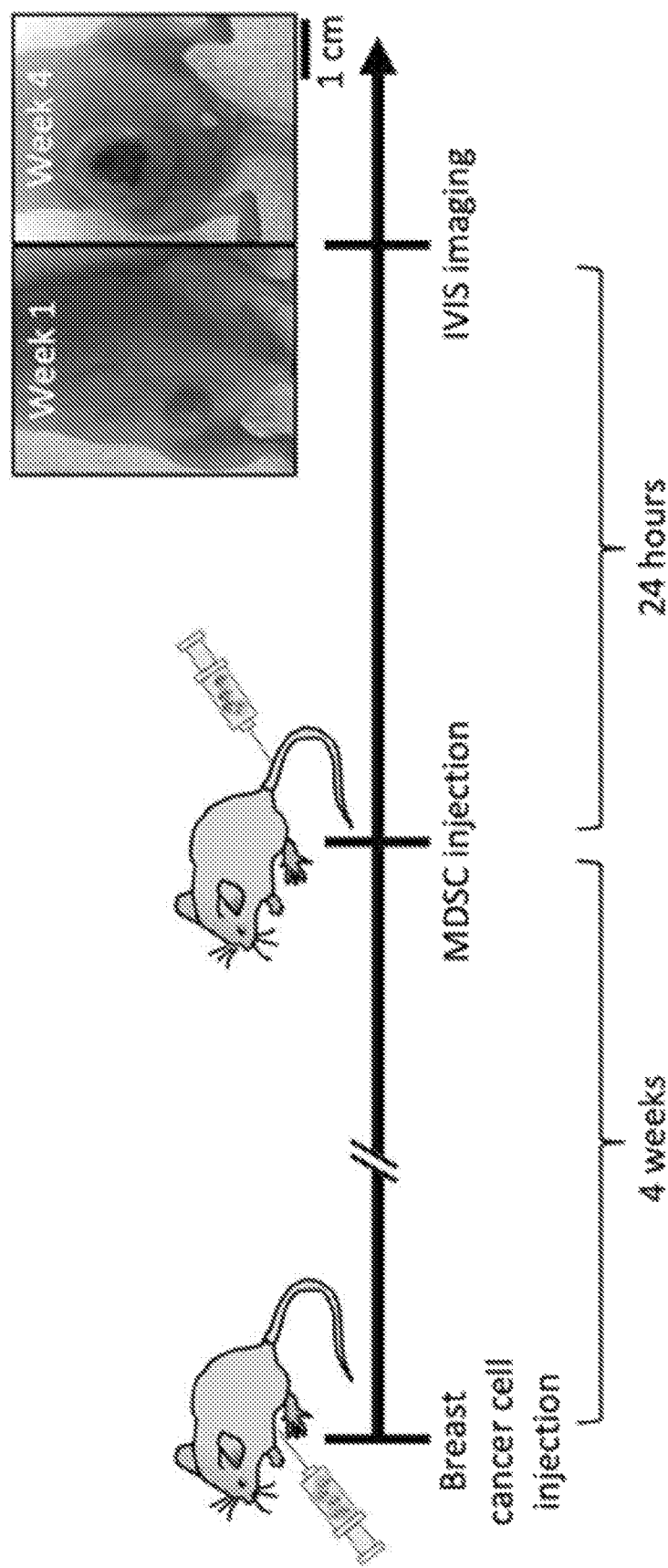
Figure 11G:
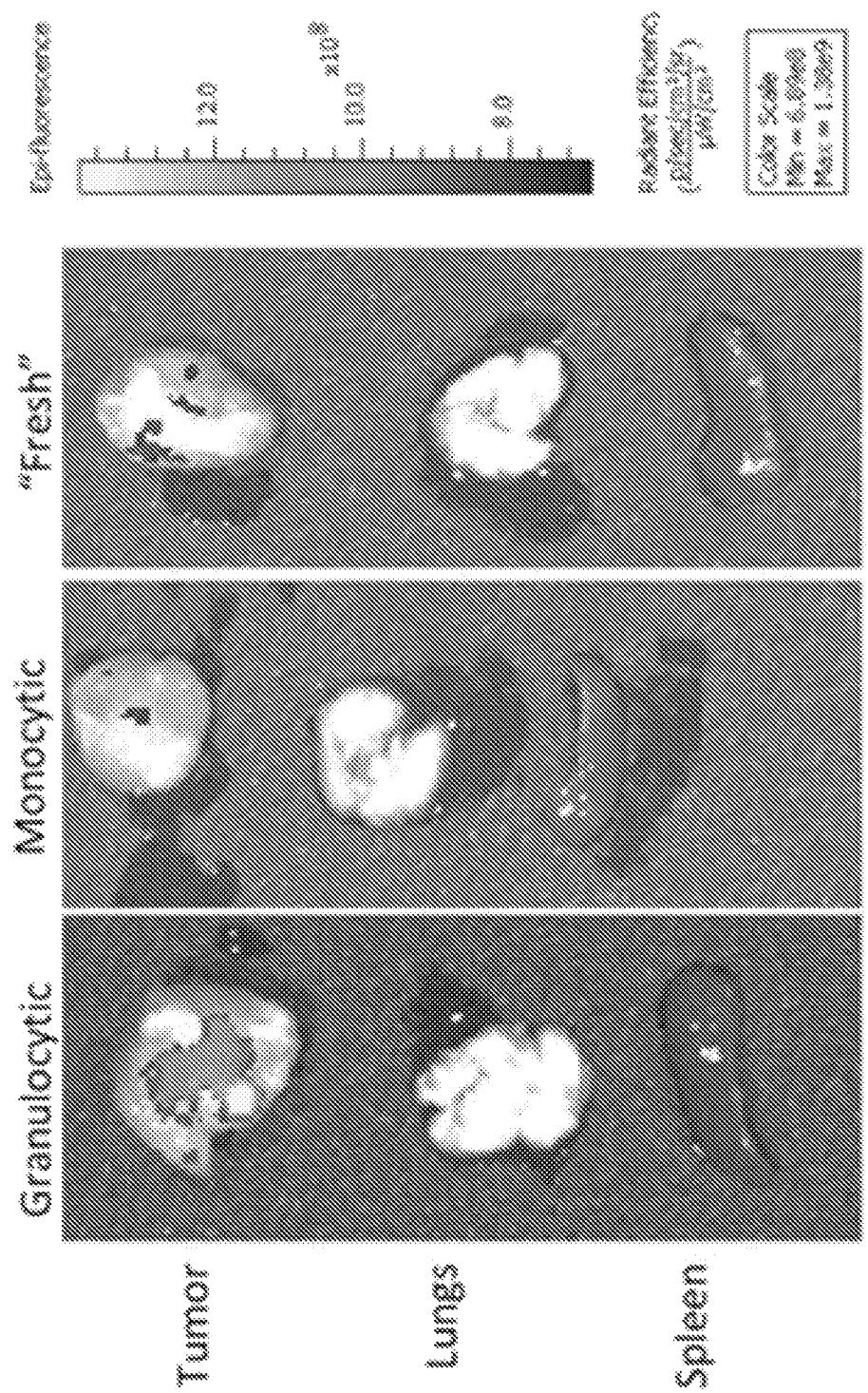
Figure 11H:
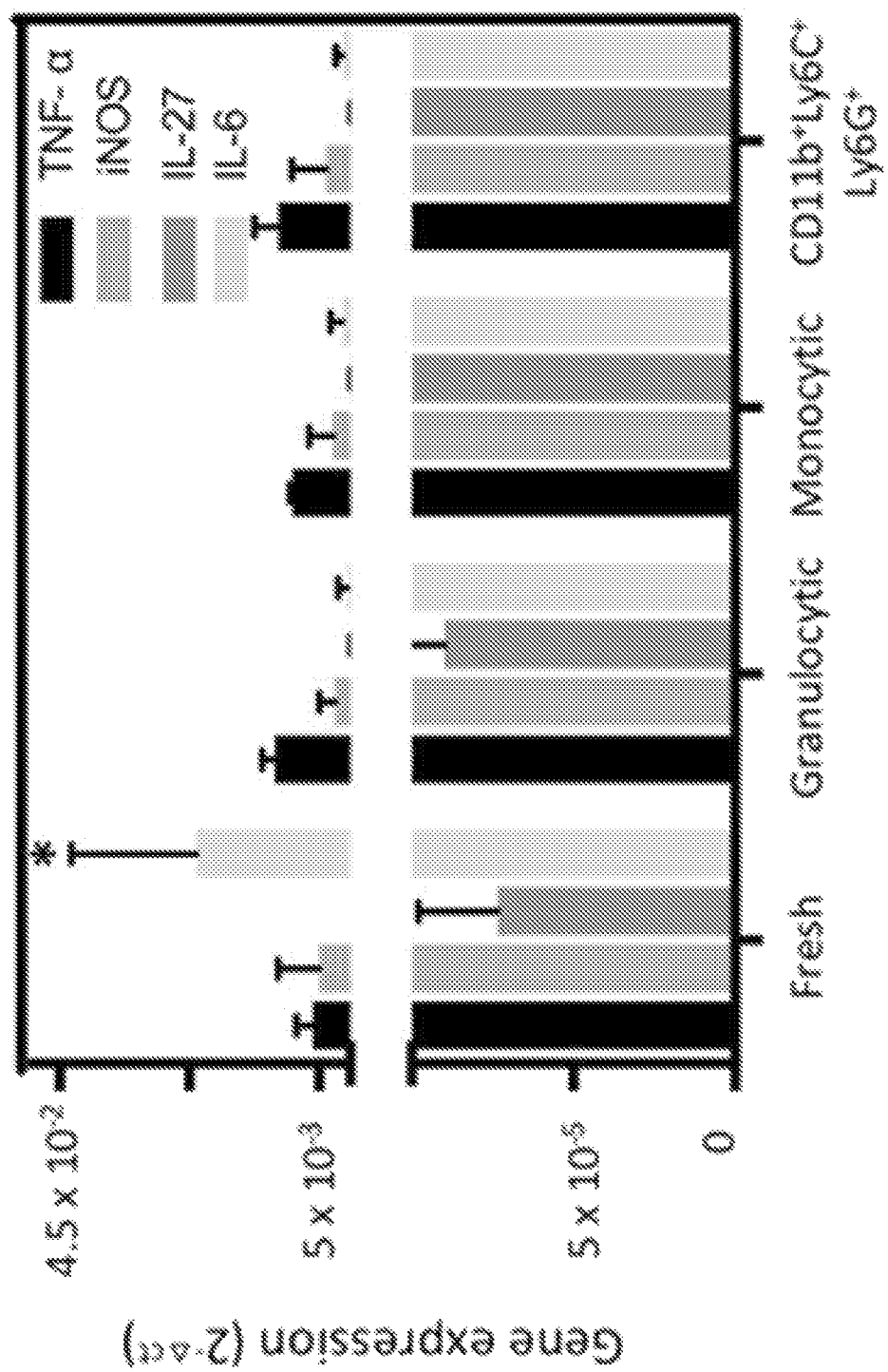
Figure 11I:
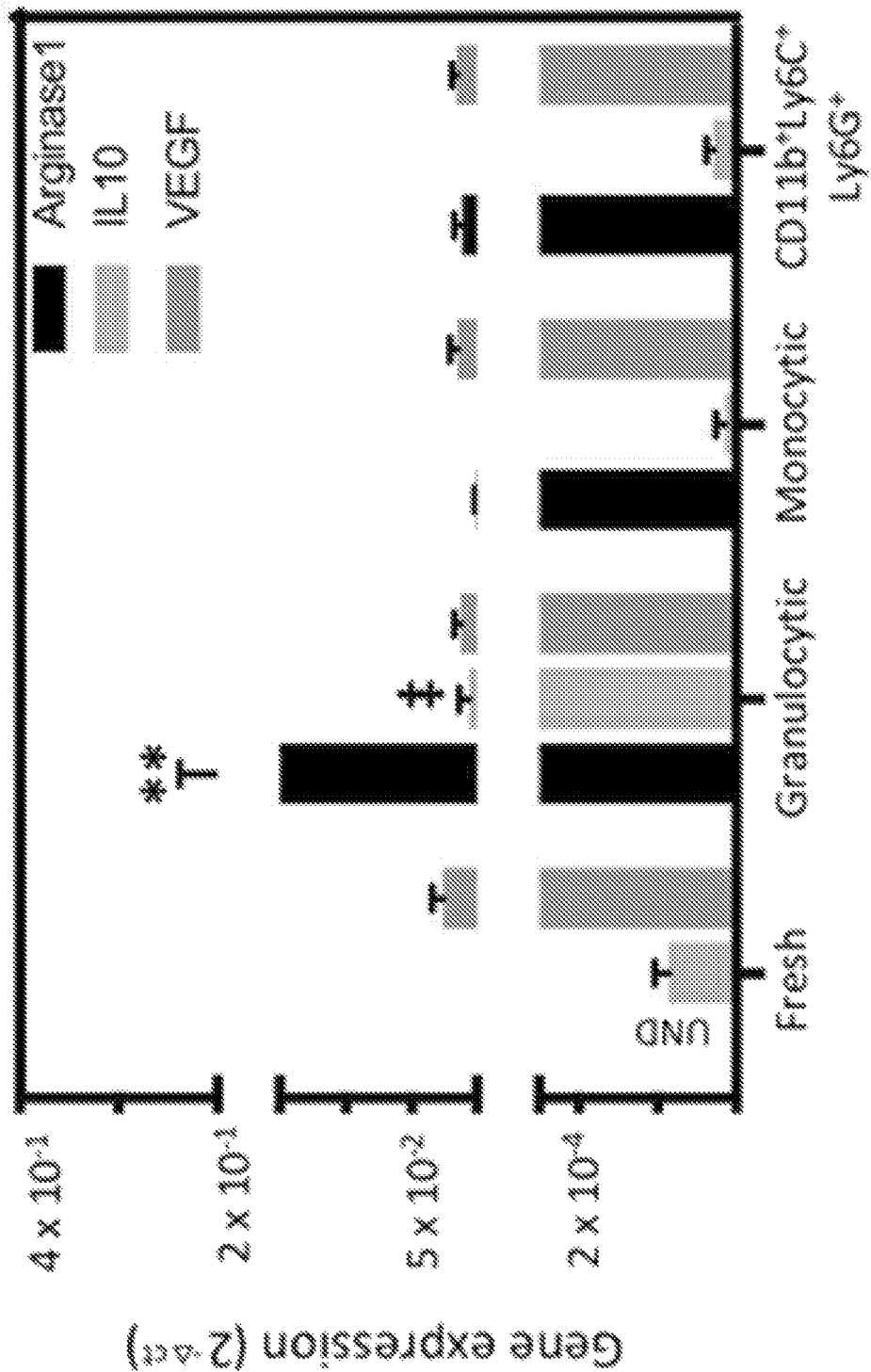

MDSC subpopulations exhibit different dissemination capabilities. Based on the clear inter-clonal variability in motility, we proceeded to further stratify and probe the MDSC population via flow cytometry-based sorting into granulocytic (CD11b$^+$Ly6C$^{lo}$Ly6G$^+$) and monocytic (CD11b$^+$Ly6C$^{hi}$Ly6G$^-$) subpopulations (FIG. 11A-11C) based on standard MDSC nomenclature (Bronte V, et al. Nat Commun 2016, 7:12150). A subpopulation of CD11b$^+$Ly6C$^+$Ly6G$^+$ cells was also identified from the flow cytometry data and included in our analyses. Flow-sorted subpopulations were then subjected to structurally guided motility studies on textured surfaces, as described above, in addition to qRT-PCR analyses of pro- and anti-inflammatory markers. Single-clone dissemination studies indicate that when probed in isolation, granulocytic MDSCs have superior dissemination capabilities compared to monocytic MDSCs and the CD11b$^+$Ly6C$^+$Ly6G$^+$ subpopulation (FIG. 11D), with single clones reaching in some cases average velocities and net displacements of >100 μm h$^{-1}$ and approximately 1.5 mm over a period of 16 hours. And while some clones within the monocytic MDSC and CD11b$^+$Ly6C$^+$Ly6G$^+$ subpopulations showed relatively high average migration velocities, approximately 50 μm h$^{-1}$, net displacements were considerably limited, thus suggesting that these cells tend to show very short range and/or disorganized motility patterns compared to granulocytic MDSCs (FIG. 11E). These observations were further confirmed via in vivo studies (FIG. 11F, 11G), where tumor-bearing mice were systemically injected with fluorescently labeled suspensions of sorted vs. "fresh"/unsorted MDSCs, and IVIS was used to document MDSC accumulation within the tumor niche vs. peripheral organs/tissues. The mice that were injected with granulocytic MDSCs showed more pronounced fluorescence signal accumulation within the tumor (FIG. 11G). Parallel single-clone motility studies with circulating MDSCs derived from cancer patients (FIG. 14) also suggest that the granulocytic subpopulation (CD11b$^+$CD15$^+$ CD14⁻) exhibits enhanced motility compared to the monocytic one (CD11b$^+$CD15$^-$CD14$^+$). MSC-2 cell gene expression analysis of pro-inflammatory markers indicate no statistically significant differences in the expression of TNF-α, iNOS, and IL-27 between the "fresh" (i.e., unsorted) MDSC population and the purified granulocytic, monocytic, and CD11b$^+$Ly6C$^+$Ly6G$^+$ subpopulations. However, IL-6 was significantly overexpressed in the fresh population vs. the flow-sorted subpopulations. Gene expression analyses of anti-inflammatory markers, on the other hand, suggest that the flow-sorted granulocytic subpopulation has a tendency to overexpress arginase and IL-10 compared to the fresh and flow-sorted monocytic MDSC and CD11b$^+$Ly6C$^+$Ly6G$^+$ subpopulations. Altogether, these results suggest that the granulocytic MDSC subpopulation appears to be not only more prone to disseminating and colonizing cancerous tissue, but also to overexpress anti-inflammatory/suppressive markers compared to the monocytic MDSC and the CD11b$^+$Ly6C$^+$Ly6G$^+$ subpopulations.

Figure 12A:
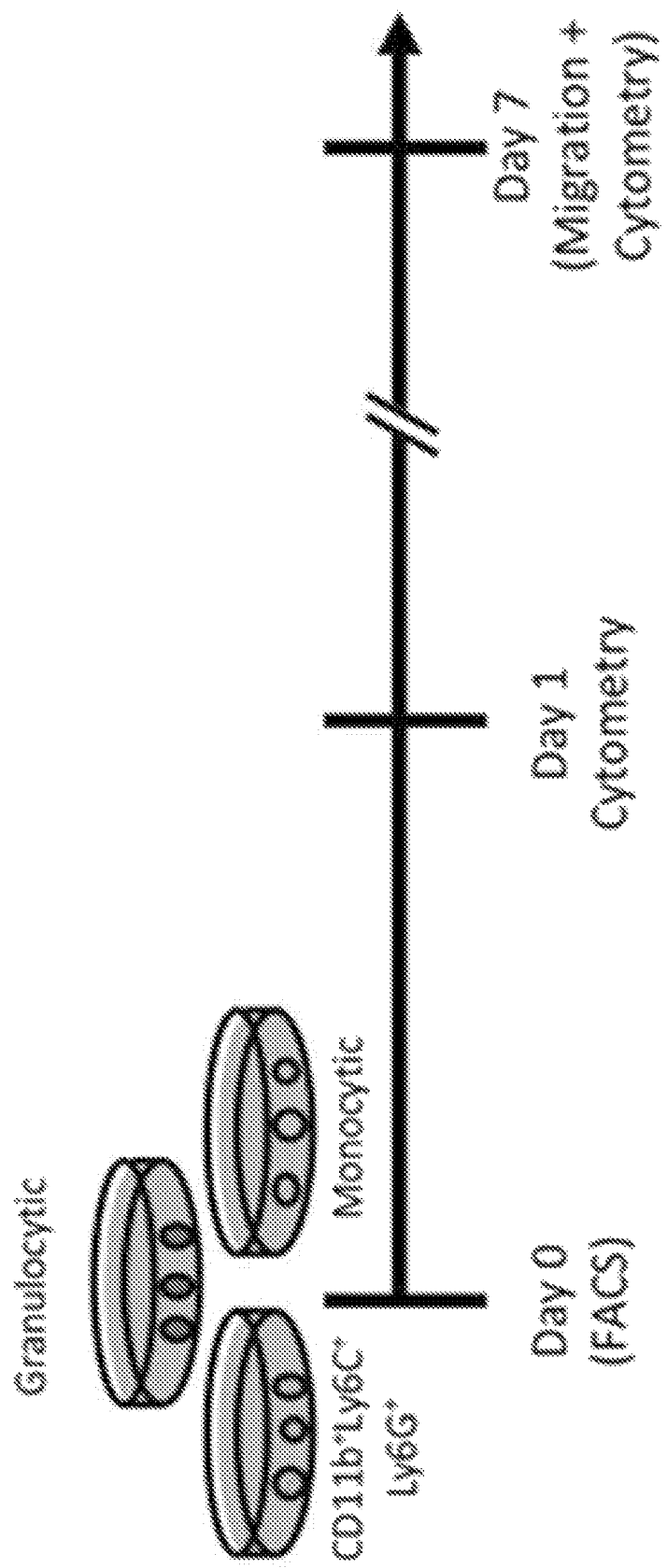
FIGS. 12A to 12G show single MDSC subpopulations appear to show phenotypic plasticity that can drive the replenishment the entire phenotypic spectrum.
Figure 12B:
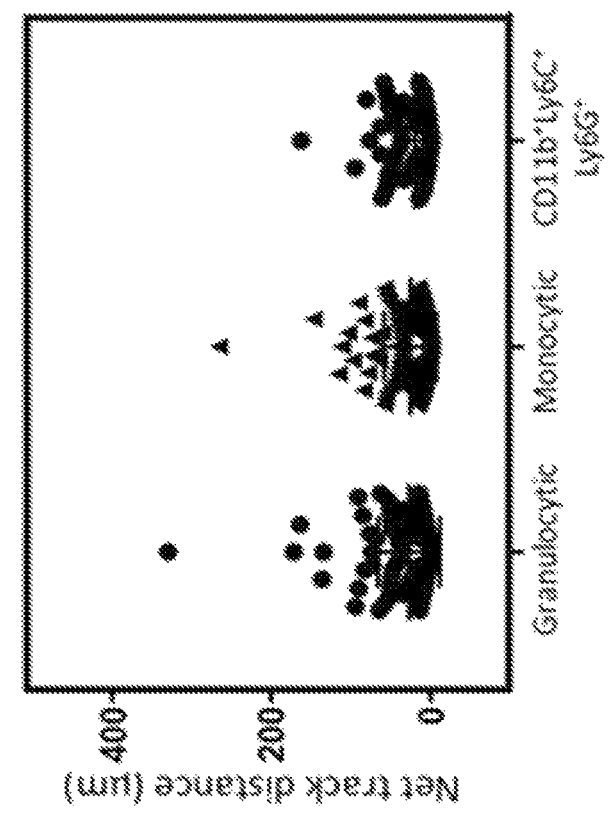
Figure 12B:
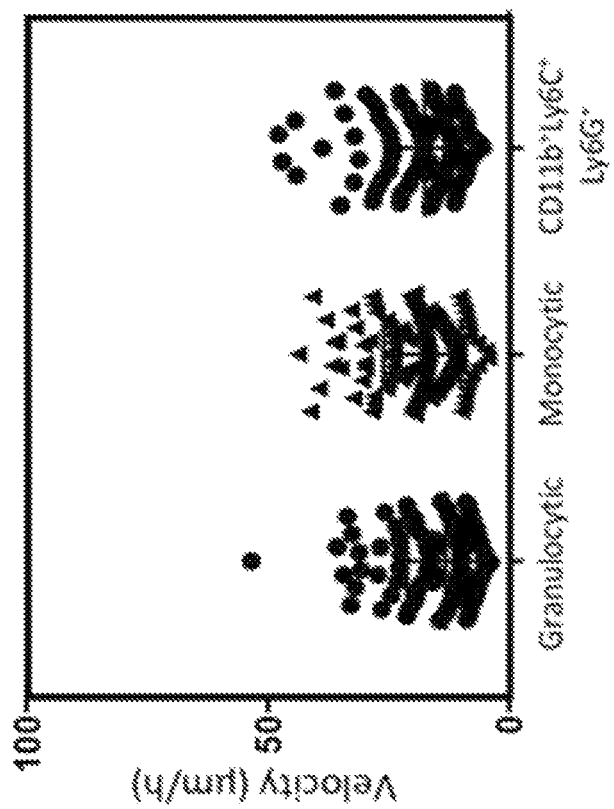
Figure 12C:
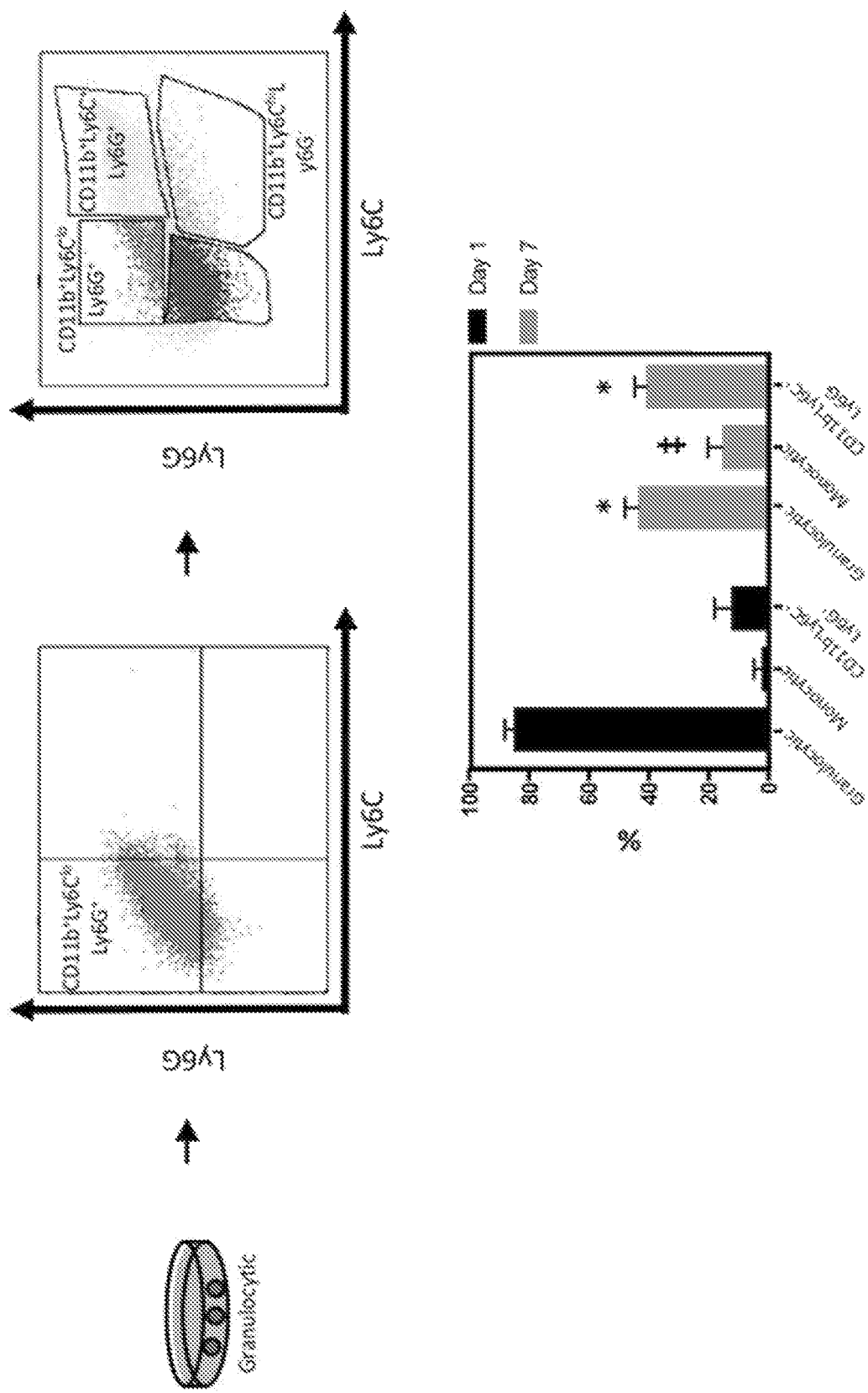
Figure 12D:
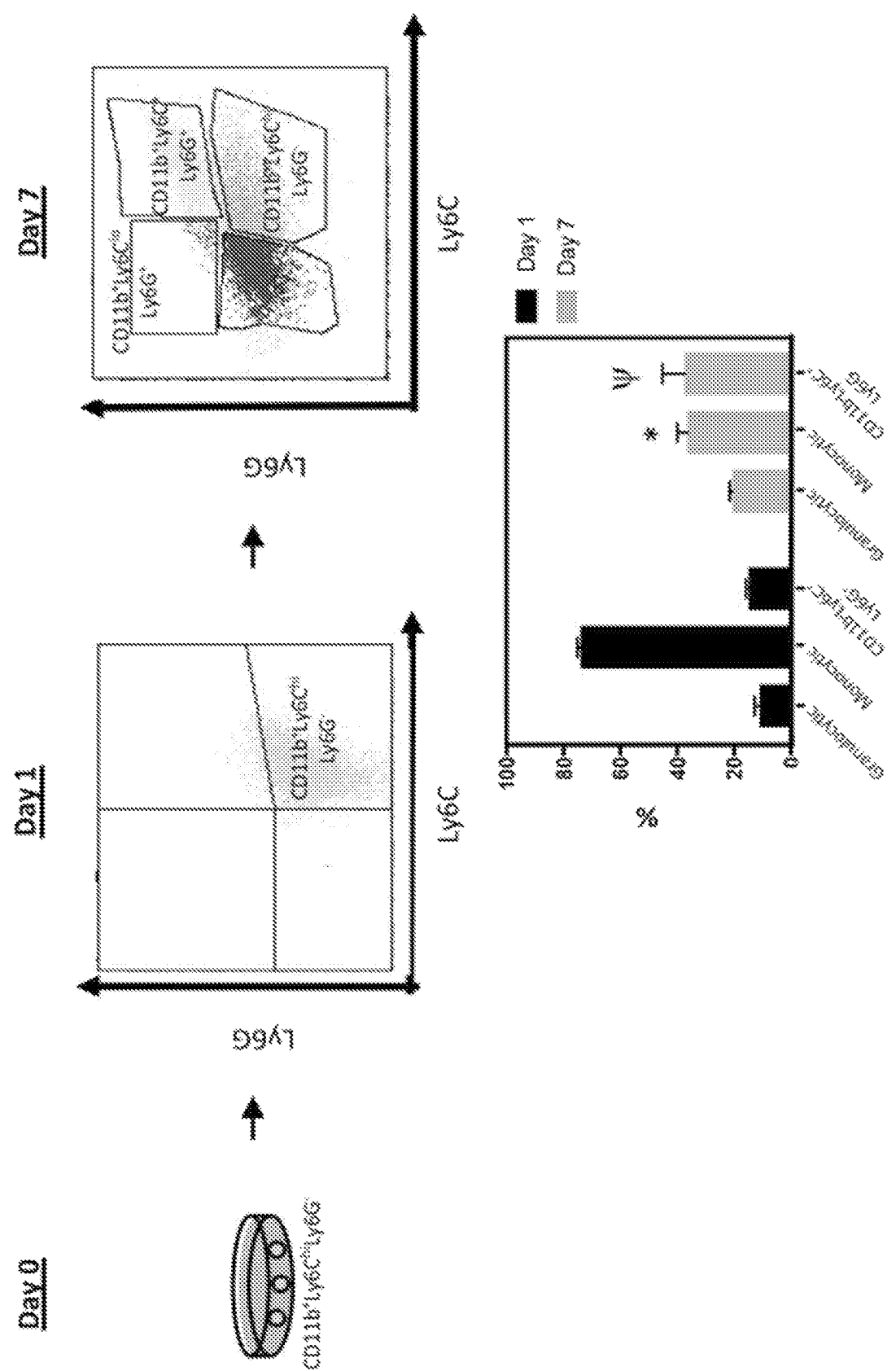
Figure 12E:
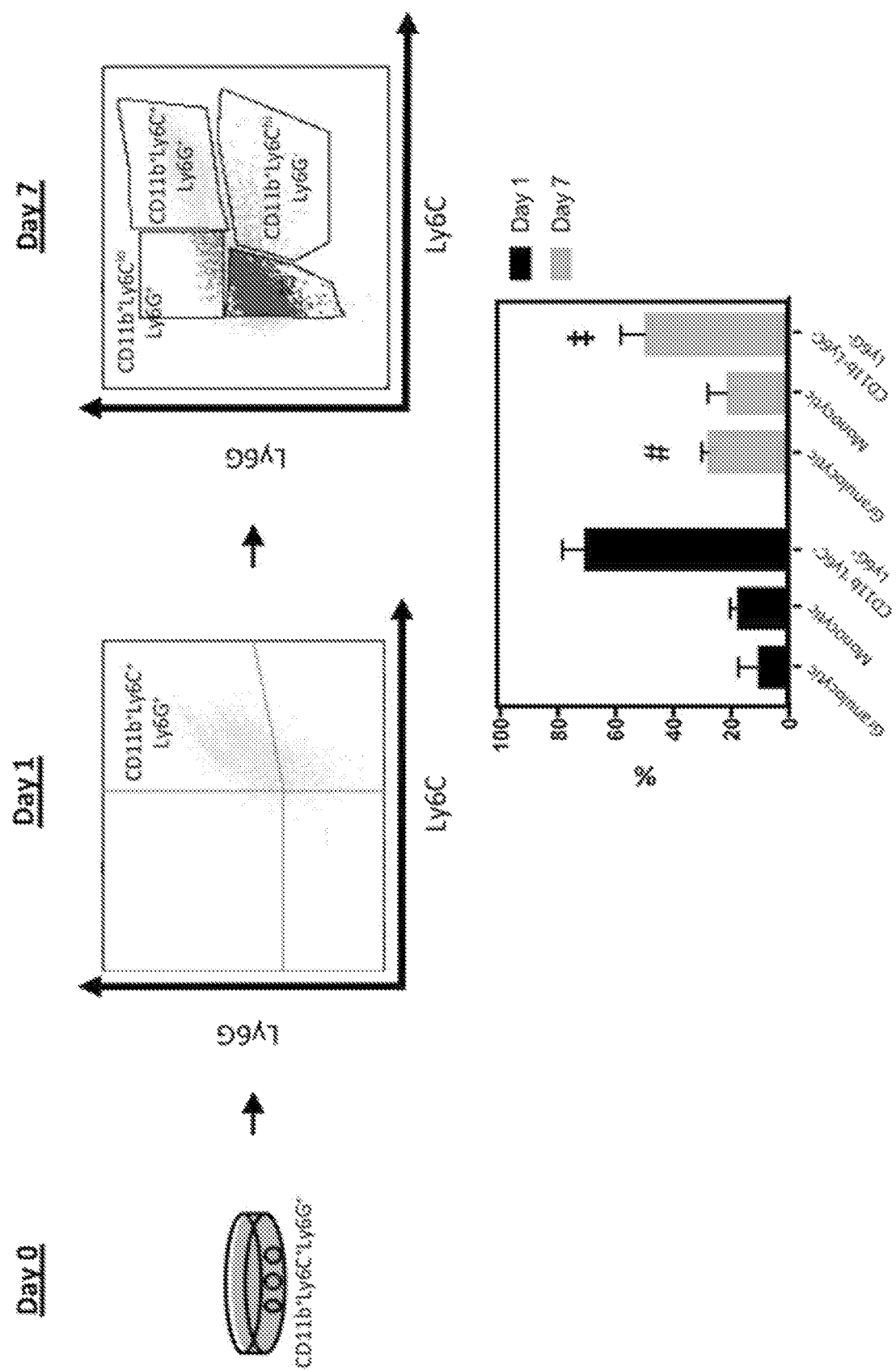
Figure 12F:
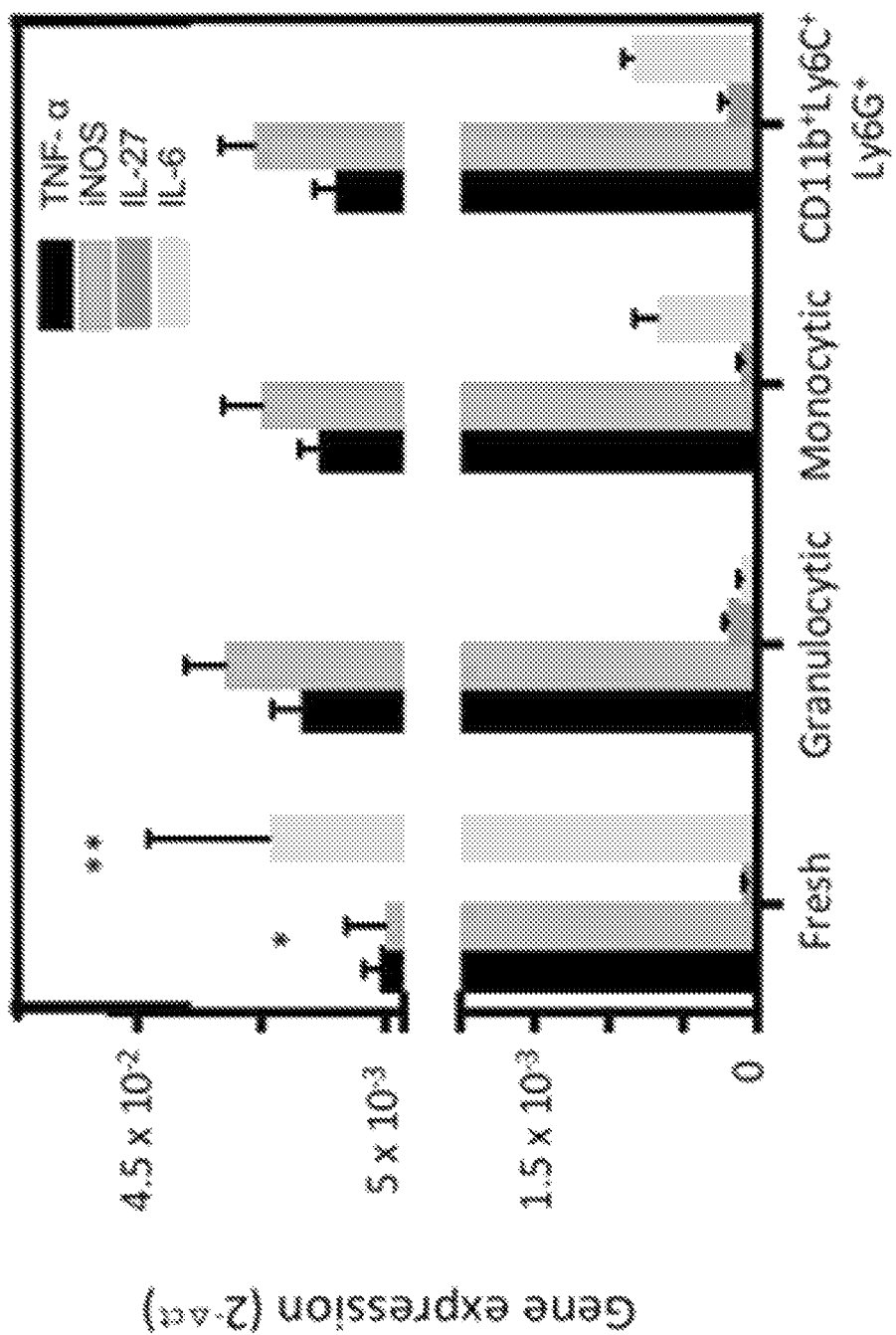
Figure 12G:
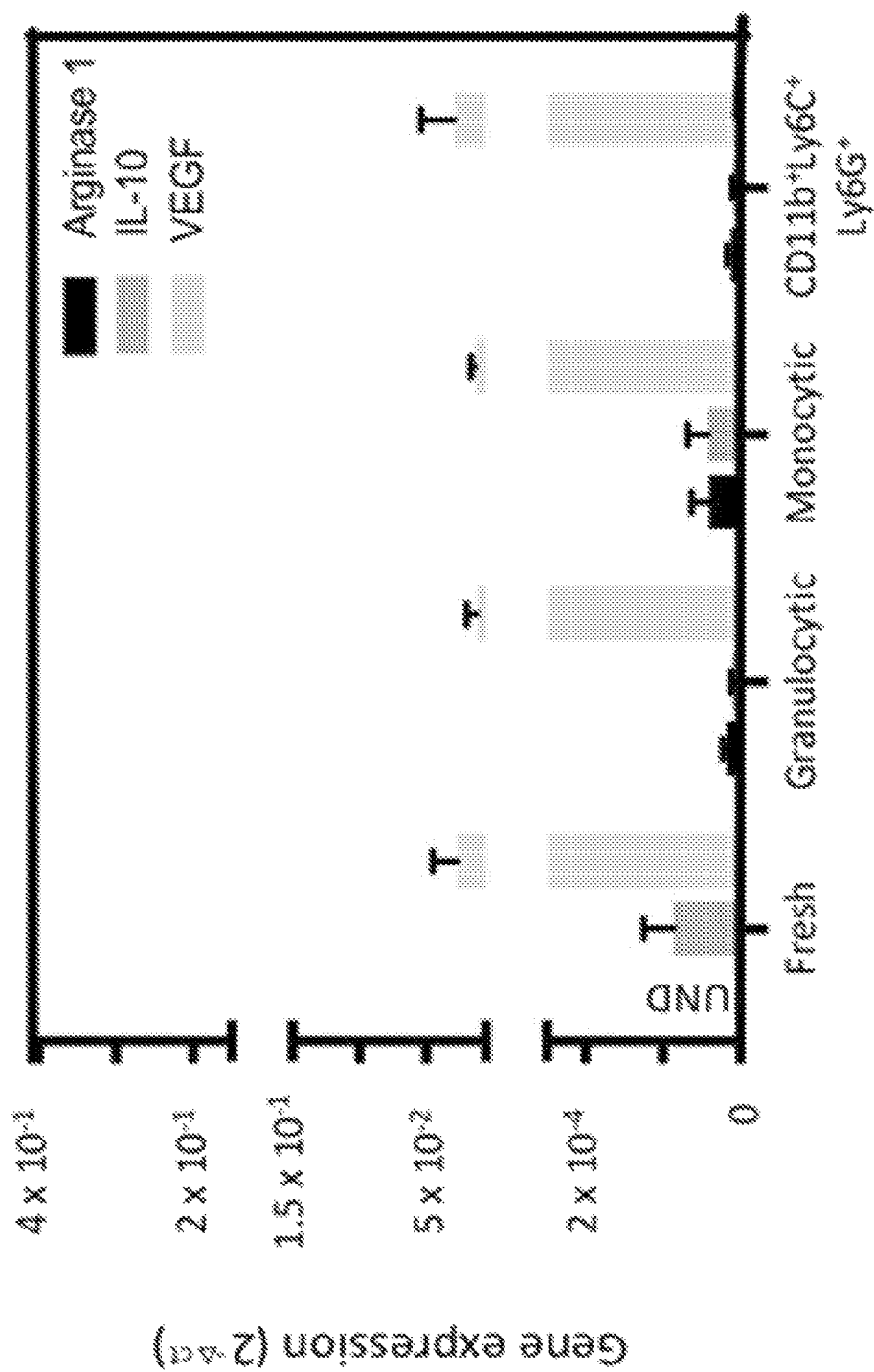
Figure 15A:
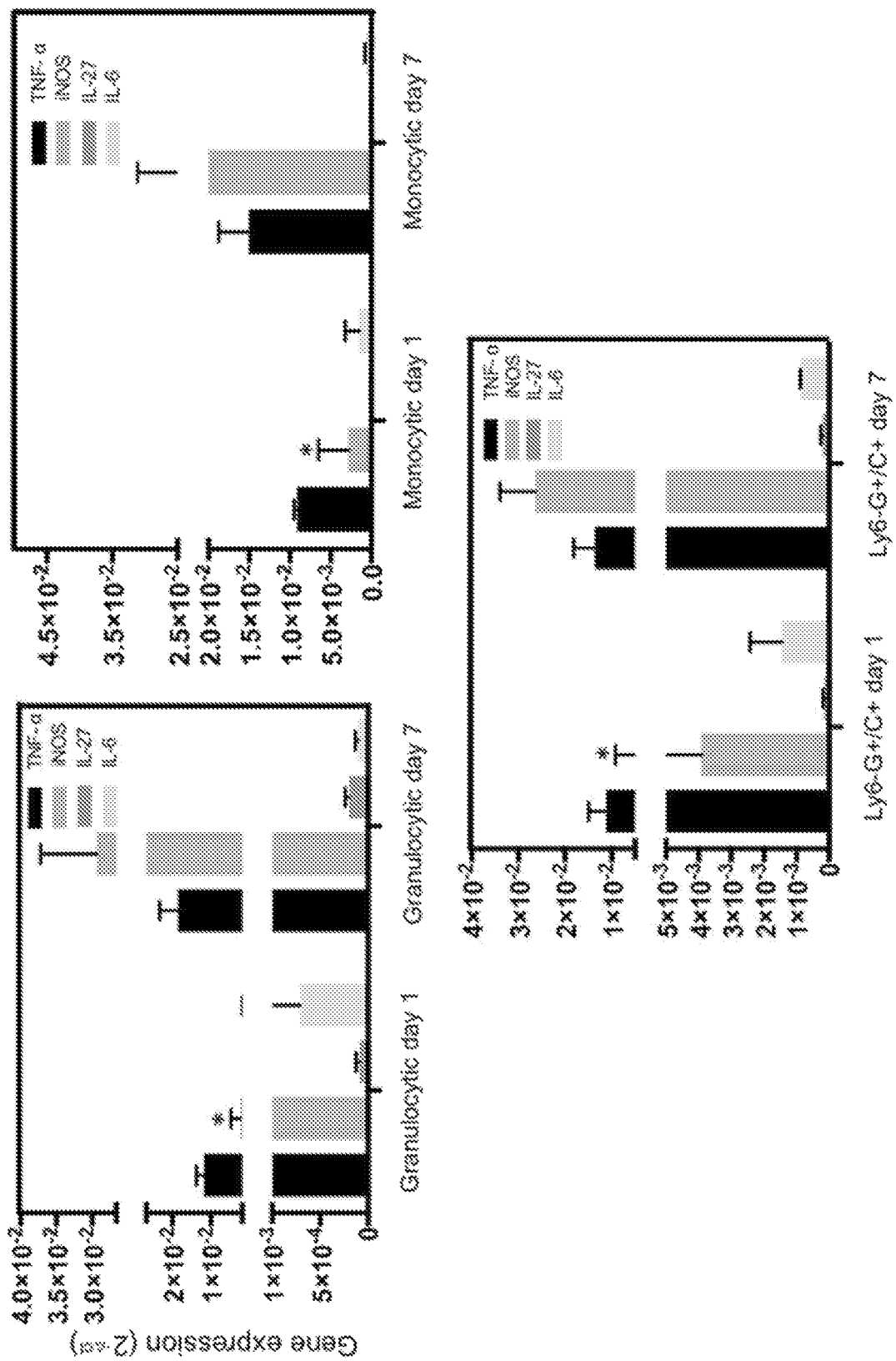
FIGS. 15A and 15B show differences in gene expression of pro-inflammatory (FIG. 15A) and anti-inflammatory (FIG. 15B) markers as a function of time for flow cytometry-sorted subpopulations. *p<0.0001, ‡p=0.06 (2-way ANOVA/Sidak's multiple comparisons, n=3-6).
Figure 15B:
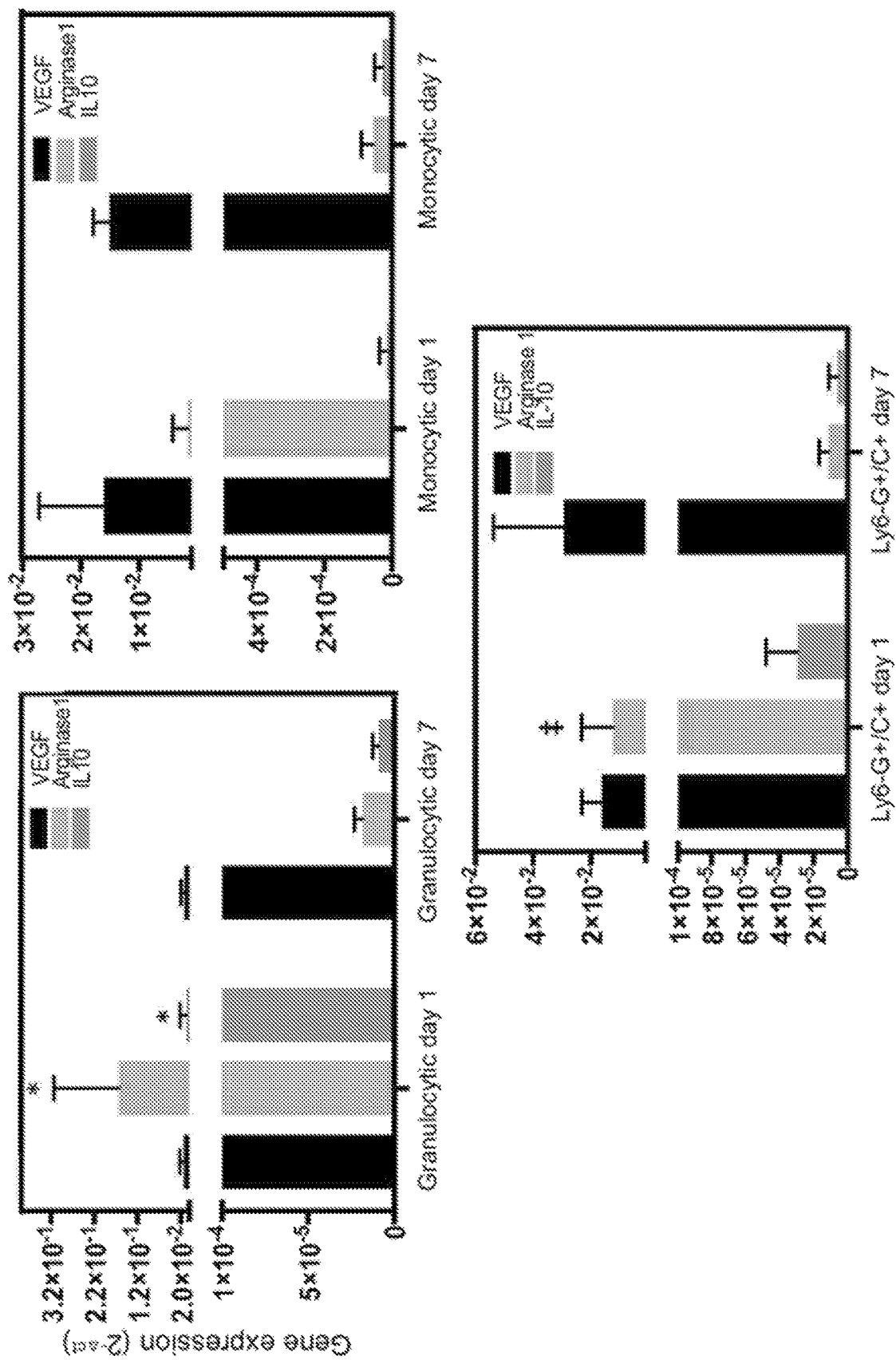

MDSC subpopulations show phenotypic plasticity that drives populational homeostasis under prolonged culture conditions. Following flow-based purification of the MSC-2 cells into distinct subpopulations of granulocytic and monocytic MDSCs, as well as CD11b$^+$Ly6C$^+$Ly6G$^+$ cells, the cells were maintained in culture for 1-7 days. Phenotypic plasticity was evaluated via flow cytometry at days 1 and 7. Single-clone motility assays and gene expression analyses were run at day 7 (FIG. 12A). Surprisingly, and in contrast to what we found immediately after flow-based sorting; no significant differences were detected in the dissemination characteristics across all three populations by day 7 (FIG. 12B). Average single-clone velocities stayed within approximately 50 μm h$^{-1}$ for all populations, while the overall net track distance stayed below approximately 200 μm. Flow cytometry analyses indicated that 1 day post-sorting the purified populations still comprised the majority (approximately 80%) of the culture, however, by day 7 the whole hierarchy of populations had been reestablished (FIG. 12C-12E), possibly suggesting a role for cellular plasticity in the maintenance of populational homeostasis/heterogeneity in MDSC populations. Cell cultures derived from the purified granulocytic subpopulation (FIG. 12C), for example, gave rise to monocytic MDSCs and CD11b$^+$Ly6C$^+$Ly6G$^+$ cells, with the monocytic subpopulation showing the sharpest increase from day 1 to 7 (approximately 7-fold change), and the CD11b$^+$Ly6C$^+$Ly6G$^+$ population showing an approximately 3-fold increase by day 7. Cultures derived from purified monocytic MDSCs, on the other hand, were more prone to giving rise to the CD11b$^+$Ly6C$^+$Ly6G$^+$ population by day 7 (approximately 2.5-fold increase) compared to the granulocytic population. Finally, cultures derived from the purified CD11b$^+$Ly6C$^+$Ly6G$^+$ population were more prone to giving rise to granulocytic MDSCs by day 7 (approximately 3-fold increase) compared to the monocytic MDSCs, which did not show a significant increase between days 1 and 7. Gene expression profiles of pro- (FIG. 12F) and anti-inflammatory (FIG. 12G) markers at day 7 showed more subtle differences across populations, with decreased and increased iNOS and IL-6 expression, respectively, in the "fresh" MDSC population relative to the sorted/purified subpopulations. However, when comparing the expression profiles between day 0 (i.e., day of sorting/purification) and day 7, a more pronounced difference was noted, with an overall increase in the expression of pro-inflammatory iNOS for all three populations, and a significant decrease in arginase1 and 11-10 for the granulocytic subpopulation only (FIG. 15).

Micro- and nanoscale technologies have been used extensively to probe and/or modulate various aspects of cell biology for medical applications (Gallego-Perez D, et al. Nano Lett 2016, 16:5326-5332; Gallego-Perez D, et al. Lab Chip 2012, 12:4424-4432; Kim S H, et al. Cancer Cell 2016, 29:201-213; Gu S Q, et al. Nucleic Acids Res 2016, 44:5811-5819; Minata M, et al. Cell reports 2019, 26:1893-1905; Shukla V C, et al. Trends in biotechnology 2018, 36:549-561; Benavente-Babace A, et al. Biosens Bioelectron 2014, 61:298-305; Fei Z, et al. Analytical chemistry 2013, 85:1401-1407; Chang L, et al. Small 2016, 12:5971-5980; Chang L, et al. Lab Chip 2015, 15:3147-3153; Gallego-Perez D, et al. Biomed Microdevices 2012, 14:779-789; Gallego-Perez D, et al. Nanomedicine 2016, 12:399-409; Gallego-Perez D, et al. Nature nanotechnology 2017, 12:974; Wu Y, et al. Small 2013, 9:2358-2367; Zhao X, et al. Advanced Science 2015, 2; Zhao X, et al. Anal Chem 2015, 87:3208-3215). Microscale engineering tools were used to demonstrate that tumor-associated MDSCs exhibit structurally guided migration patterns, similar to invasive cancerous cells. Single-clone motility analyses unmasked clear heterogeneities within and across (i.e., for patient-derived MDSCs) MDSC populations, confirming the presence of clonal subsets with enhanced dissemination capabilities in both murine and patient-derived MDSCs. Follow-up motility studies coupled with flow cytometry-based sorting, gene expression analyses, and orthotopic tumor xenograft experiments in nude mice, suggest that the granulocytic subpopulation is more prone to exhibiting increased dissemination and tumor-infiltrative ability, as well as enhanced anti-inflammatory activity, which could make this population an attractive therapeutic target in cancer. Subsequent studies, however, highlight the remarkably dynamic and plastic nature of such clonal subsets, with purified MDSC subpopulations quickly reaching populational homeostasis by giving rise to the full spectrum of MDSC phenotypes. While there have been conflicting reports regarding the dominant phenotype of tumor-resident MDSCs (i.e., granulocytic vs. monocytic) (Kumar V, et al. Trends in immunology 2016, 37:208-220; Hossain F, et al. Cancer immunology research 2015, 3:1236-1247; Haverkamp J M, et al. European journal of immunology 2011, 41:749-759; Mairhofer D G, et al. Journal of Investigative Dermatology 2015, 135:2785-2793; Bozkus C C, et al. The Journal of Immunology 2015, 195:5237-5250), our single-clone dissemination and phenotypic plasticity results point towards a potential mechanism by which granulocytic MDSCs are presumably better equipped to infiltrate the tumor niche, where they could then remain as granulocytic and/or give raise to monocytic MDSCs depending on multiple factors, including the tumor type. Interestingly, single-clone dissemination studies with circulating MDSCs derived from cancer patients suggest that MDSC motility could potentially be impacted by the patient's background (e.g., type/stage of cancer, treatment modalities, etc.), and as such, additional studies are needed to determine whether the dissemination patterns of circulating MDSCs, ex vivo, could be used to monitor disease and/or treatment progression.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing a therapeutic stealth cell, comprising (a) sorting myeloid-derived suppressor cells (MDSCs) from a sample from a subject for a subpopulation of the granulocytic CD11b+Ly6C$^{lo}$Ly6G+ MDSCs; and (b) reprogramming the subpopulation of MDSCs to deliver anti-cancer agents.

2. The method of claim 1, wherein the subpopulation is sorted in a migration assay using a chemoattractant gradient.

3. The method of claim 1, wherein the subpopulation is sorted in a migration assay using a nanotextured and/or biomimetic surface.

4. The method of claim 1, wherein the subpopulation is sorted in a transwell migration assay or Boyden chamber assay.

5. The method of claim 1, wherein the subpopulation is reprogrammed to heterologously express a transgene encoding an anti-tumor protein, oligonucleotide, or combination thereof.

6. The method of claim 5, wherein the transgene encodes tissue inhibitor of metalloproteinase-3 (TIMP-3).

7. The method of claim 1, wherein the subpopulation is further reprogrammed with a kill switch system.

8. The method of claim 1, wherein the subpopulation is sorted by flow cytometry.

9. A composition, comprising a plurality of therapeutic stealth cell produced by the method of claim 1.

10. The composition of claim 9, further comprising a pharmaceutically acceptable excipient.

* * * * *